US012630510B2

(12) United States Patent
Watanabe et al.

(10) Patent No.: US 12,630,510 B2
(45) Date of Patent: May 19, 2026

(54) EP2 ANTAGONIST

(71) Applicant: ONO PHARMACEUTICAL CO., LTD., Osaka (JP)

(72) Inventors: Akio Watanabe, Osaka (JP); Atsushi Yoshida, Osaka (JP); Yasuo Hirooka, Osaka (JP); Michael G. Yang, Narberth, PA (US); Ning Li, Lexington, MA (US)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 1140 days.

(21) Appl. No.: 17/621,137

(22) PCT Filed: Jun. 26, 2020

(86) PCT No.: PCT/JP2020/025187

§ 371 (c)(1),
(2) Date: Dec. 20, 2021

(87) PCT Pub. No.: WO2020/262603

PCT Pub. Date: Dec. 30, 2020

(65) Prior Publication Data

US 2022/0388955 A1 Dec. 8, 2022

(30) Foreign Application Priority Data

Jun. 28, 2019 (JP) ................................. 2019-122077

(51) Int. Cl.

| | |
|---|---|
| ***C07D 207/34*** | (2006.01) |
| ***A61K 31/145*** | (2006.01) |
| ***A61K 31/167*** | (2006.01) |
| ***A61K 31/192*** | (2006.01) |
| ***A61K 31/40*** | (2006.01) |
| ***A61K 31/415*** | (2006.01) |
| ***A61K 31/4174*** | (2006.01) |
| ***A61K 31/44*** | (2006.01) |
| ***A61K 31/4439*** | (2006.01) |
| ***A61K 31/4965*** | (2006.01) |
| ***A61K 31/519*** | (2006.01) |
| ***A61P 35/00*** | (2006.01) |
| ***C07C 233/76*** | (2006.01) |
| ***C07C 323/29*** | (2006.01) |
| ***C07D 213/56*** | (2006.01) |
| ***C07D 213/75*** | (2006.01) |

(Continued)

(52) U.S. Cl.

CPC .......... *C07D 207/34* (2013.01); *A61K 31/145* (2013.01); *A61K 31/167* (2013.01); *A61K 31/192* (2013.01); *A61K 31/40* (2013.01); *A61K 31/415* (2013.01); *A61K 31/4174* (2013.01); *A61K 31/44* (2013.01); *A61K 31/4439* (2013.01); *A61K 31/4965* (2013.01); *A61K 31/519* (2013.01); *A61P 35/00* (2018.01); *C07C 233/76* (2013.01); *C07C 323/29* (2013.01); *C07D 213/56* (2013.01); *C07D 213/75* (2013.01); *C07D 231/12* (2013.01); *C07D 233/70* (2013.01); *C07D 241/18* (2013.01); *C07D 401/12* (2013.01); *C07D 487/04* (2013.01); *C07C 2601/16* (2017.05)

(58) Field of Classification Search

CPC ..... A61P 35/00; C07D 207/34; C07D 233/70; C07D 241/18; A61K 31/145; A61K 31/167; A61K 31/40; A61K 31/415; A61K 31/4174; A61K 31/44; A61K 31/4439; A61K 31/4965; A61K 31/519; C07C 233/76; C07C 323/29

See application file for complete search history.

(56) References Cited

U.S. PATENT DOCUMENTS

| | | | | |
|---|---|---|---|---|
| 6,693,208 B2 * | 2/2004 | Gscheidner | C07C 235/64 564/171 | |
| 7,601,712 B2 * | 10/2009 | Naganawa | A61P 37/06 514/452 | |

(Continued)

FOREIGN PATENT DOCUMENTS

| | | |
|---|---|---|
| JP | 2002-522413 A | 7/2002 |
| WO | 00/27823 A1 | 5/2000 |

(Continued)

OTHER PUBLICATIONS

Ganesh et al. "Prostanoid Receptor EP2 as a Therapeutic Target" J. Med. Chem. 2014, 57, 4454â4465 (Year: 2014).*

(Continued)

*Primary Examiner* — Kortney L. Klinkel
(74) *Attorney, Agent, or Firm* — Sughrue Mion, PLLC

(57) ABSTRACT

A drug containing, as an active ingredient, a compound having an antagonistic activity against an $EP_2$ receptor in the prevention and/or treatment of a disease associated with the activation of an $EP_2$ receptor, of formula (I-A):

(I-A)

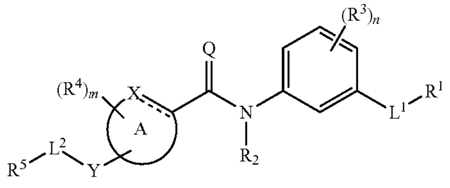

wherein all symbols have the same meanings as those described in the specification, or a pharmaceutically acceptable salt thereof.

14 Claims, 1 Drawing Sheet

(51) Int. Cl.

| | |
|---|---|
| ***C07D 231/12*** | (2006.01) |
| ***C07D 233/70*** | (2006.01) |
| ***C07D 241/18*** | (2006.01) |
| ***C07D 401/12*** | (2006.01) |
| ***C07D 487/04*** | (2006.01) |

(56) References Cited

U.S. PATENT DOCUMENTS 8,318,729 B2 * 11/2012 Naganawa ................ A61P 3/06 514/230.5
8,476,266 B2 * 7/2013 Naganawa ................ A61P 1/16 514/230.5
8,809,524 B2 * 8/2014 Naganawa .............. A61P 35/02 544/105

FOREIGN PATENT DOCUMENTS

WO WO-2005080367 A1 * 9/2005 ........... C07C 233/75
WO 00/07979 A2 2/2020

OTHER PUBLICATIONS

Mokhtari et al. "Combination therapy in combating cancer" Oncotarget. 2017, 8, 23, 38022-38043 (Year: 2017).*

Sun et al. "Prostaglandin EP2 receptor: Novel therapeutic target for human cancers (Review" Int. J. Mol. Med 2018 42 1204-1214 (Year: 2018).*

Supporting information for Pure enantiomers of benzoylamino-tranylcypromine: LSD1 inhibition, gene modulation in human leukemia cells and effects on clonogenic potential of murine promyelocytic blasts (Year: 2015).*

Valente et al. "Pure enantiomers of benzoylamino-tranylcypromine: LSD1 inhibition, gene modulation in human leukemia cells and effects on clonogenic potential of murine promyelocytic blasts" Eur. J. Med. Chem. 2015 94 164-174 (Year: 2015).*

"RN 1909449-55-3", May 13, 2016, Registry [online], American Chemical Society, [retrieved on Sep. 16, 2020]. (1 page total).

RN 1909449-49-5, May 13, 2016, Registry [online], American Chemical Society, [retrieved on Sep. 16, 2020]. (1 page total).

RN 1908172-49-5, May 11, 2016, Registry [online], American Chemical Society, [retrieved on Sep. 16, 2020]. (1 page total).

Bojarska-Dahlig, H. N., "Iodo Derivatives of 5-Methyl-1-Phenyl-1,2,3-Triazolecarboxylic Acid", Recueil des Travaux Chemiques des Pays-Bas, 1961, vol. 80, No. 12, pp. 1348-1356.

RN 1910075-55-6, May 13, 2016, Registry [online], American Chemical Society, [retrieved on Sep. 16, 2020]. (1 page total).

RN 1909449-40-6, May 13, 2016, Registry [online], American Chemical Society, [retrieved on Sep. 16, 2020]. (1 page total).

International Search Report (PCT/ISA/210) issued Sep. 29, 2020 by the International Searching Authority in counterpart International Patent Application No. PCT/JP2020/025187.

Written Opinion (PCT/ISA/237) issued Sep. 29, 2020 by the International Searching Authority in counterpart International Patent Application No. PCT/JP2020/025187.

* cited by examiner

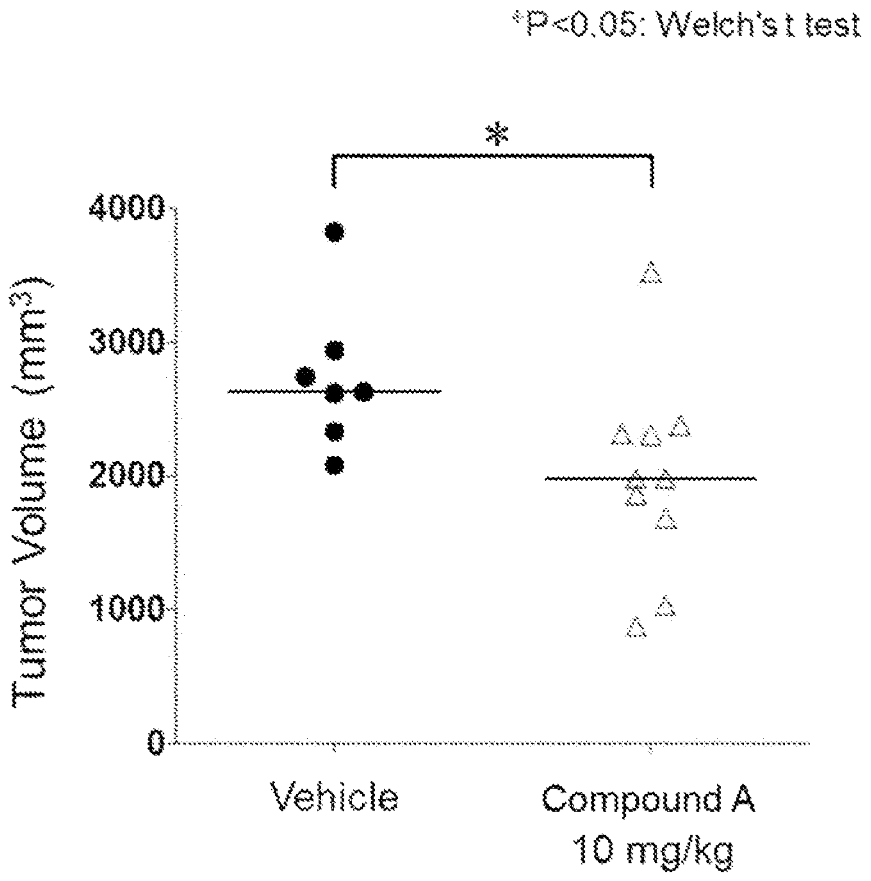
*P<0.05: Welch's t test
*
Tumor Volume (mm3)
4000
3000
2000
1000
0
Vehicle
Compound A
10 mg/kg

EP2 ANTAGONIST

This is a U.S. National Stage of International Application No. PCT/JP2020/025187 filed Jun. 26, 2020, claiming priority from Japanese Patent Application No. 2019-122077 filed Jun. 28, 2019, the entire disclosures of which are incorporated by reference herein.

TECHNICAL FIELD

The present invention relates to: a compound having an antagonistic activity against an $EP_2$ receptor, or a pharmaceutically acceptable salt thereof; and a medicament comprising the compound or a pharmaceutically acceptable salt thereof as an active ingredient. More specifically, the present invention relates to: a compound represented by general formula (I-A):

(I-A)

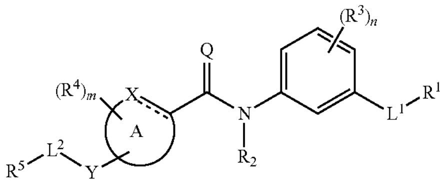

(wherein all symbols have the same meanings as described below) or a pharmaceutically acceptable salt thereof (wherein the compound or the salt thereof is also referred to as "the compound of the present invention", hereinafter); and a medicament comprising the compound or a pharmaceutically acceptable salt thereof as an active ingredient.

BACKGROUND ART

Prostaglandin $E_2$ ($PGE_2$) is known as a metabolic product in an arachidonic acid cascade, and is known to have a cell protection effect, a uterine contraction effect, an effect to reduce a pain threshold, an effect to promote the peristaltic motions of digestive tracts, a promotion effect of wakefulness, a gastric secretion inhibiting effect, a hypotensive effect, a diuretic effect and the like.

A $PGE_2$ receptor is divided into subtypes having different roles from each other, and the subtypes are called "an $EP_1$ receptor", "an $EP_2$ receptor", "an $EP_3$ receptor", and "an $EP_4$ receptor" (Non-Patent Document 1).

Among these subtypes, an $EP_2$ receptor is involved in the signaling of cAMP, and therefore it is known that an $EP_2$ receptor is involved in the relaxation of a circular muscle in the trachea or the ileum or the dilation of various blood vessels. It is also known that an $EP_2$ receptor is involved in the expression of PI3K, Akt or GSK-3β or IL-1β, IL-6, IL-12, IL-23 and IL-27. Furthermore, it is believed that an $EP_2$ receptor is also involved in the inhibition of the production of MCP-1 from a macrophage, the inhibition of the production of TNF-α, IL-2 and IFN-γ from a lymphocyte, anti-inflammation due to the enhancement of production of IL-10, vasodilation, neovascularization, the inhibition of the formation of elastic fibers, and the regulation of the expression of MMP-9. In addition, it is believed that an $EP_2$ receptor is also involved in the immune-mediated suppression of cancer via myeloid-derived suppressor cells, regulatory T cells and natural killer cells.

Therefore, it is known that an $EP_2$ receptor is associated with an anti-inflammatory effect, a nerve protective effect and an anti-tumor effect. Therefore, it is considered that a compound which can bind strongly to an $EP_2$ receptor and has an antagonistic activity against an $EP_2$ receptor is useful for the prevention and/or treatment of a disease associated with the activation of an $EP_2$ receptor, such as endometriosis, uterine fibroids, hypermenorrhea, adenomyosis, dysmenorrhea, chronic pelvic pain syndrome, cancer, inflammatory pain, neuropathic pain, headache, migraine, postoperative pain, interstitial cystitis, leiomyoma, irritable colon syndrome, Alzheimer's disease, Parkinson's disease, amyotrophic lateral sclerosis, multiple sclerosis, rheumatism, osteoarthritis, gout, an allergic disease, hypertension, brain dysfunction, ischemia, stroke, a kidney disease, transplant rejection, atherosclerosis, an ischemic heart disease, acne vulgaris, asthma, prostatitis, glomerulonephritis, sarcoidosis, vasculitis and an autoimmune disease (Non-Patent Documents 2 to 4).

On the other hand, it is described that a compound represented by general formula (A) disclosed in Patent Document 1 can be used for the treatment of a disease associated with SRS-A, such as an allergic disease, an ischemic heart disease and an inflammation.

General formula (A) is as follows:

(A)

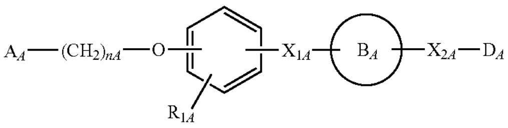

(wherein:

$A_A$ represents a hydrogen atom, a phenyl group or a phenoxy group;

$n_A$ represents an integer of 3 to 10;

$R_{1A}$ represents a hydrogen atom or a lower alkoxy group;

$X_{1A}$ represents —CO—$Y_{2A}$— (wherein $Y_{2A}$ represents —NH— or the like) or the like;

the symbol

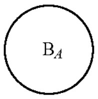

represents

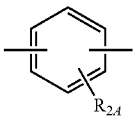

or the like;

$R_{2A}$ represents a hydrogen atom, halogen, a lower haloalkyl group or the like;

$X_{2A}$ represents —$Y_{3A}$—$Y_{4A}$—, wherein $Y_{3A}$ represents a single bond or the like and $Y_{4A}$ represents an alkylene group having 1 to 6 carbon atoms, or the like; and $D_A$ represents a carboxy group, a lower alkoxycarbonyl group or the like (a part is extracted from the definitions of groups)).

As examples of the $EP_2$ antagonist, a compound represented by general formula (B) shown below which is disclosed in Patent Document 2 and a compound represented by general formula (C) shown below which is disclosed in Patent Document 3 are known.

General formula (B) is as follows:

(B)

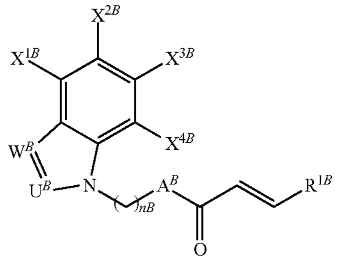

(wherein:

$A^B$ represents $NR^{5B}$ or the like;

$U^B$ represents $CX^{5B}$ or N;

$W^B$ represents $CX^{6B}$ or N;

$n^B$ represents 1, 2, 3 or 4;

$R^{1B}$ represents a carbocyclic ring, aryl, a heterocyclic ring or the like;

$X^{1B}$, $X^{2B}$, $X^{3B}$ and $X^{4B}$ may be the same as or different from one another, and independently represent a hydrogen atom, an alkyl group, halogen or the like;

$R^{5B}$ represents a hydrogen atom, an alkyl group or the like; and $X^{5B}$ and $X^{6B}$ may be the same as or different from each other, and independently represent a hydrogen atom, an alkyl group or the like (a part is extracted from the definitions of groups).

General formula (C) is as follows:

(C)

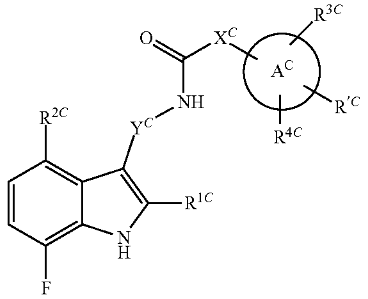

(wherein:

$A^c$ represents a C5-12 heteroaryl group which may be substituted;

$R'^c$ represents a —$S(O)_p$—(C1-C6 alkyl) group or the like, wherein p represents 0 to 2;

$R^{1c}$ represents a hydrogen atom, a C1-C6 alkyl group or the like;

$R^{2c}$, $R^{3c}$ and $R^4$, independently represent a hydrogen atom, halogen or the like;

$X^c$ represents —C≡C— or the like; and $Y_c$ represents —$(CH_2)_n$—, wherein n represents 2 or 3 (a part is extracted from the definitions of groups)).

Patent Document 4 discloses methyl 3-[5-({[1-tert-butyl-5-(4-fluorophenyl-1H-pyrazol-4-yl]carbonyl}amino-2-chlorophenyl]propanoate and 3-[5-({[1-tert-butyl-5-(4-fluorophenyl-1H-pyrazol-4-yl]carbonyl}amino-2-chlorophenyl] propanoic acid.

However, in either one of these prior art documents, there is found no statement or suggestion about the compound of the present invention.

CITATIONS LIST

Patent Documents

Patent Document 1: International Publication No. 1986/005779 pamphlet

Patent Document 2: International Publication No. 2012/177618 pamphlet

Patent Document 3: International Publication No. 2008/152097 pamphlet

Patent Document 4: International Publication No. 2007/052843 pamphlet

Non-Patent Documents

Non-Patent Document 1: Journal of Lipid Mediators and Cell Signalling, vol. 12, pp. 379-391, 1995

Non-Patent Document 2: Journal of the Medicinal Chemistry, vol. 57, pp. 4454-4465, 2014

Non-Patent Document 3: Trends in Pharmacological Science, vol. 34, pp. 413-423, 2013

Non-Patent Document 4: International Journal of molecular medicine, vol. 42, pp. 1203-1214, 2018

SUMMARY OF INVENTION

Technical Problems

An object of the present invention is to discover a compound that has a potent antagonistic activity against an $EP_2$ receptor and therefore is useful as a prophylactic and/or therapeutic agent for a disease associated with the activation of an $EP_2$ receptor.

Solutions to Problems

The present inventors have made intensive and extensive studies in order to achieve the object. As a result, the present inventors have found that the object can be achieved by: a compound represented by general formula (I-A) mentioned below, and completed the present invention.

The present invention relates to the following items:

[1] a compound represented by general formula (I-A):

(I-A)

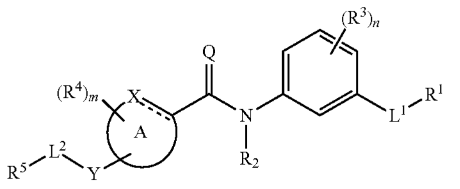

(wherein:

$L^1$ represents —$(CR^{38}R^{39})$—$(CR^{40}R^{41})$—;

$R^{38}$, $R^{39}$, $R^{40}$ and $R^{41}$ each independently represent (1) a hydrogen atom, (2) a halogen atom, or (3) a C1-4 alkyl group;

the C1-4 alkyl group in each of $R^{38}$, $R^{39}$, $R^{40}$ and $R^{41}$ may be independently substituted by a halogen atom;

when each of two substituents selected from $R^{38}$, $R^{39}$, $R^{40}$ and $R^{41}$ is a C1-4 alkyl group, the two substituents may form a C3-6 saturated carbocyclic ring in conjunction with a carbon atom to which the substituents bind;

$L^2$ represents (1) a bond, (2) a C1-8 alkylene group, (3) a C2-8 alkenylene group, or (4) a C2-8 alkynylene group, wherein one or two carbon atoms in the C1-8 alkylene group, the C2-8 alkenylene group and the C2-8 alkynylene group may be independently replaced by an oxygen atom or a sulfur atom that may be oxidized, and each of the C1-8 alkylene group, the C2-8 alkenylene group and the C2-8 alkynylene group may be substituted by 1 to 8 halogen atoms;

Y represents (1) a bond, (2) an oxygen atom, or (3) a sulfur atom that may be oxidized;

$R^1$ represents (1) $COOR^{10}$, (2) $SO_3H$, (3) $SO_2NHR^{11}$, (4) $CONHSO_2R^{12}$, (5) $SO_2NHCOR^{13}$, (6) $CONR^{14}R^{15}$, (7) a tetrazolyl group, or (8) a hydroxamic acid (CONHOH);

$R^{10}$, $R^{11}$, $R^{12}$, $R^{13}$, $R^{14}$ and $R^{15}$ each independently represent (1) a hydrogen atom or (2) a C1-4 alkyl group;

$R^2$ represents (1) a hydrogen atom or (2) a C1-4 alkyl group;

$R^3$ represents (1) a halogen atom, (2) a C1-6 alkyl group, (3) a C2-6 alkenyl group, (4) a C2-6 alkynyl group, (5) a C1-6 alkoxy group, (6) a 3- to 6-membered cyclic group, (7) a (3- to 6-membered cyclic group)-O—, or (8) a (3- to 6-membered cyclic group)-(C1-4 alkylene)-;

each of the groups (2) to (8) in $R^3$ may be substituted by 1 to 9 $R^{16}$s;

when there are a plurality of $R^3$s, the plurality of $R^3$s may be the same as or different from each other;

$R^{16}$ represents (1) a halogen atom, (2) a C1-4 alkyl group, (3) a C1-4 alkoxy group, (4) a C2-6 acyl group, (5) a C3-6 cycloalkyl group, (6) a hydroxyl group, or (7) —$NR^{17}R^{18}$;

when there are a plurality of $R^{16}$s, the plurality of $R^{16}$s may be the same as or different from each other;

$R^{17}$ and $R^{18}$ each independently represent (1) a hydrogen atom or (2) a C1-4 alkyl group;

$R^4$ represents (1) a halogen atom, (2) a C1-6 alkyl group, (3) a C2-6 alkenyl group, (4) a C2-6 alkynyl group, (5) a C1-6 alkoxy group, (6) a 3- to 6-membered cyclic group, (7) (3- to 6-membered cyclic group)-O—, or (8) (3- to 6-membered cyclic group)-(C1-4 alkylene)-;

each of the groups (2) to (8) in $R^4$ may be substituted by 1 to 9 $R^{19}$s;

when there are a plurality of $R^4$s, the plurality of $R^4$s may be the same as or different from each other;

$R^{19}$ represents (1) a halogen atom, (2) a C1-4 alkyl group, (3) a C1-4 alkoxy group, (4) a C2-6 acyl group, (5) a C3-6 cycloalkyl group, (6) a hydroxyl group, or (7) —$NR^{20}R^{21}$;

$R^{20}$ and $R^{21}$ each independently represent (1) a hydrogen atom or (2) a C1-4 alkyl group;

when there are a plurality of $R^{19}$s, the plurality of $R^{19}$s may be the same as or different from each other;

$R^5$ represents (1) a hydrogen atom, (2) a C3-10 carbocyclic ring, or (3) a 3- to 10-membered heterocyclic ring, wherein each of the C3-10 carbocyclic ring and the 3- to 10-membered heterocyclic ring may be substituted by 1 to 5 $R^{22}$s;

when $L^2$ represents a bond, $R^5$ is not a hydrogen atom;

$R^{22}$ represents (1) a C1-6 alkyl group, (2) a C2-6 alkenyl group, (3) a C2-6 alkynyl group, (4) a C3-6 cycloalkyl group, (5) a C1-6 alkoxy group, (6) a C3-6 cycloalkyloxy group, (7) a C2-6 acyl group, (8) a C2-6 acyloxy group, (9) a C1-6 alkylthio group, (10) a C3-6 cycloalkylthio group, (11) a C1-6 alkylsulfinyl group, (12) a C3-6 cycloalkylsulfinyl group, (13) a C1-6 alkylsulfonyl group, (14) a C3-6 cycloalkylsulfonyl group, (15) a C1-6 alkoxycarbonyl group, (16) a 5- to 6-membered cyclic group, (17) (5- to 6-membered cyclic group)-(C1-4 alkylene)-, (18) a (5- to 6-membered cyclic group)-(C1-4 alkylene)-O— group, (19) a (5- to 6-membered cyclic group)-C1-4 acyl group, (20) a halogen atom, (21) a hydroxyl group, (22) a nitro group, (23) a cyano group, (24) —$NR^{23}R^{24}$, (25) —$CONR^{25}R^{26}$ or (26) —$SO_2NR^{27}R^{28}$;

$R^{23}$, $R^{24}$, $R^{25}$, $R^{26}$, $R^{27}$ and $R^{28}$ each independently represent (1) a hydrogen atom, (2) a C1-6 alkyl group, (3) a C2-6 acyl group or (4) a C1-6 alkylsulfonyl group;

each of the groups (1) to (19) in $R^{22}$ may be substituted by 1 to 9 $R^{29}$s;

when there are a plurality of $R^{22}$s, the plurality of $R^{22}$s may be the same as or different from each other;

$R^{29}$ represents (1) a C1-4 alkyl group, (2) a C1-4 alkoxy group, (3) a C2-6 acyl group, (4) a C3-6 cycloalkyl group, (5) a hydroxyl group, (6) —$NR^{30}R^{31}$ or (7) a halogen atom;

$R^{30}$ and $R^{31}$ each independently represent (1) a hydrogen atom or (2) a C1-4 alkyl group;

when there are a plurality of $R^{29}$s, the plurality of $R^{29}$s may be the same as or different from each other;

Q represents (1) an oxygen atom or (2) a sulfur atom;

X represents (1) $CR^6$ or (2) $NR^7$;

$R^6$ represents (1) a halogen atom, (2) a C1-6 alkyl group, (3) a C2-6 alkenyl group, (4) a C2-6 alkynyl group, (5) a C1-6 alkoxy group, (6) a 3- to 6-membered cyclic group, (7) (3- to 6-membered cyclic group)-O—, or (8) (3- to 6-membered cyclic group)-(C1-4 alkylene)-;

each of the groups (2) to (8) in $R^6$ may be substituted by 1 to 9 $R^{32}$s;

$R^{32}$ represents (1) a halogen atom, (2) a C1-4 alkyl group, (3) a C1-4 alkoxy group, (4) a C2-6 acyl group, (5) a C3-6 cycloalkyl group, (6) a hydroxyl group, or (7) —$NR^{33}R^{34}$;

$R^{33}$ and $R^{34}$ each independently represent (1) a hydrogen atom or (2) a C1-4 alkyl group;

when there are a plurality of $R^{32}$s, the plurality of $R^{32}$s may be the same as or different from each other;

$R^7$ represents (1) a C1-6 alkyl group, (2) a C2-6 alkenyl group, (3) a C2-6 alkynyl group, (4) a 3- to 6-membered cyclic group, or (5) (3- to 6-membered cyclic group)-(C1-4 alkylene)-;

$R^7$ may be substituted by 1 to 9 $R^{35}$s;

$R^{35}$ represents (1) a halogen atom, (2) a C1-4 alkyl group, (3) a C1-4 alkoxy group, (4) a C2-6 acyl group, (5) a C3-6 cycloalkyl group, (6) a hydroxyl group, or (7) —$NR^{36}R^{37}$;

$R^{36}$ and $R^{37}$ each independently represent (1) a hydrogen atom or (2) a C1-4 alkyl group;

when there are a plurality of $R^{35}$s, the plurality of $R^{35}$s may be the same as or different from each other;

the ring A represents (1) a benzene ring, or (2) a 5- to 6-membered nitrogen-containing aromatic heterocyclic ring;

the symbol

in the ring A represents a single bond or a double bond;

n represents an integer of 1 to 4; and m represents an integer of 0 to 3, provided that 3-[3-[(2,6-dimethoxybenzoyl)amino]-4-propoxyphenyl]propanoic acid, methyl 3-[5-({[1-tert-butyl-5-(4-fluorophenyl-1H-pyrazol-4-yl]carbonyl}amino-2-chlorophenyl]propanoate, 3-[5-({[1-tert-butyl-5-(4-fluorophenyl-1H-pyrazol-4-yl]carbonyl}amino-2-chlorophenyl]propanoic acid, α-ethyl-3-[N-(1'-phenyl-5'-methyl-1',2',3'-triazolecarbonyl)]amino-2,4,6-triiodohydrocinnamic acid, and α-ethyl-3-{N-(1'-(4''-iodophenyl)-5'-methyl-1,2,3-triazolecarbonyl)}amino-2,4,6-triiodohydrocinnamic acid are excluded), or a pharmaceutically acceptable salt thereof,

[2] the compound according to item [1], or a pharmaceutically acceptable salt thereof, wherein the compound is a compound represented by general formula (I):

(I)

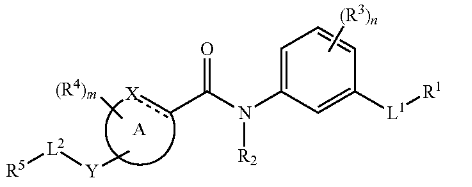

(wherein all symbols have the same meanings as those recited in item [1]);

[3] the compound according to item [1], or a pharmaceutically acceptable salt thereof, wherein the compound is a compound represented by general formula (I-B):

(I-B)

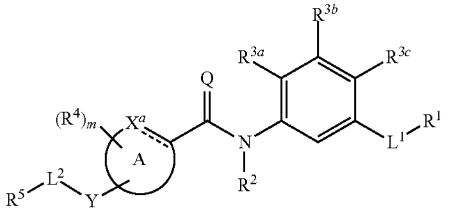

(wherein:

$X^a$ represents $CR^{6a}$ or $NR^{7a}$;

$R^{6a}$ represents (1) a halogen atom, (2) a C1-6 alkyl group, (3) a C2-6 alkenyl group, (4) a C2-6 alkynyl group, (5) a C1-6 alkoxy group, (6) (3- to 6-membered cyclic group)-O—, or (7) (3- to 6-membered cyclic group)-(C1-4 alkylene)-;

each of the groups (2) to (7) in $R^{6a}$ may be substituted by 1 to 9 $R^{32}$s;

$R^{7a}$ represents (1) a C1-6 alkyl group, (2) a C2-6 alkenyl group, (3) a C2-6 alkynyl group, (4) a 3- to 6-membered cyclic group, or (5) (3- to 6-membered cyclic group)-(C1-4 alkylene)-;

$R^{7a}$ may be substituted by 1 to 9 $R^{35}$s;

$R^{3a}$, $R^{3b}$ and $R^{3c}$ each independently represent (1) a hydrogen atom, (2) a halogen atom, (3) a C1-6 alkyl group, (4) a C2-6 alkenyl group, (5) a C2-6 alkynyl group, (6) a C1-6 alkoxy group, (7) a 3- to 6-membered cyclic group, (8) (3- to 6-membered cyclic group)-O—, or (9) (3- to 6-membered cyclic group)-(C1-4 alkylene)-;

each of the groups (3) to (9) in $R^{3a}$, $R^{3b}$ and $R^{3c}$ may be substituted by 1 to 9 $R^{16}$s;

wherein at least one of $R^{3a}$, $R^{3b}$ and $R^{3c}$ represents a substituent other than a hydrogen atom; and wherein the same symbols as those recited in item [1] have the same meanings as those recited in item [1];

provided that 3-[3-[(2,6-dimethoxybenzoyl)amino]-4-propoxyphenyl]propanoic acid is excluded);

[4] the compound according to item [1] or [2], or a pharmaceutically acceptable salt thereof, wherein the compound is a compound represented by general formula (I-1):

(I-1)

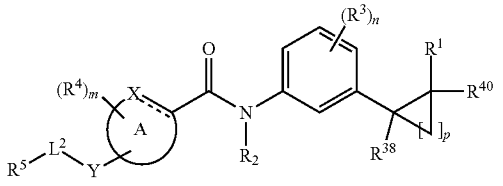

(wherein p represents an integer of 1 to 4; and other symbols have the same meanings as those recited in item [1]);

[5] the compound according to any one of items [1] to [4], or a pharmaceutically acceptable salt thereof, wherein the compound is a compound represented by general formula (I-C):

(I-C)

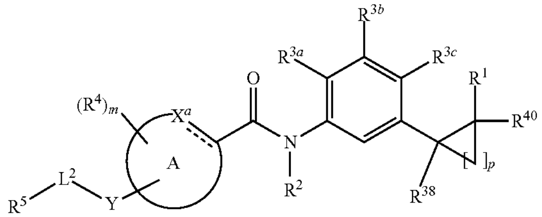

(wherein:

$X^a$ represents $CR^{6a}$ or $NR^{7a}$;

$R^{6a}$ represents (1) a halogen atom, (2) a C1-6 alkyl group, (3) a C2-6 alkenyl group, (4) a C2-6 alkynyl group, (5) a C1-6 alkoxy group, (6) (3- to 6-membered cyclic group)-O—, or (7) (3- to 6-membered cyclic group)-(C1-4 alkylene)-;

each of the groups (2) to (7) in $R^{6a}$ may be substituted by 1 to 9 $R^{32}$s;

$R^{7a}$ represents (1) a C1-6 alkyl group, (2) a C2-6 alkenyl group, (3) a C2-6 alkynyl group, (4) a 3- to 6-membered cyclic group, or (5) (3- to 6-membered cyclic group)-(C1-4 alkylene)-;

$R^{7a}$ may be substituted by 1 to 9 $R^{35}$s;

$R^{3a}$, $R^{3b}$ and $R^{3c}$ each independently represent (1) a hydrogen atom, (2) a halogen atom, (3) a C1-6 alkyl group, (4) a C2-6 alkenyl group, (5) a C2-6 alkynyl group, (6) a C1-6 alkoxy group, (7) a 3- to 6-membered cyclic group, (8) (3- to 6-membered cyclic group)-O—, or (9) (3- to 6-membered cyclic group)-(C1-4 alkylene)-;

each of the groups (3) to (9) in $R^{3a}$, $R^{3b}$ and $R^{3c}$ may be substituted by 1 to 9 $R^{16}$s;

wherein at least one of $R^{3a}$, $R^{3b}$ and $R^{3c}$ represents a substituent other than a hydrogen atom;

p represents an integer of 1 to 4; and the same symbols as those recited in item [1] have the same meanings as those recited in item [1]);

[6] the compound according to any one of items [1] to [5], or a pharmaceutically acceptable salt thereof, wherein the ring A is a benzene ring or a 5-membered nitrogen-containing aromatic heterocyclic ring;

[7] the compound according to any one of items [1] to [6], or a pharmaceutically acceptable salt thereof, wherein $L^2$ represents a C1-8 alkylene group, a C2-8 alkenylene group, or a C2-8 alkynylene group, wherein one or two carbon atoms in the C1-8 alkylene group, the C2-8 alkenylene group and the C2-8 alkynylene group may be independently replaced by an oxygen atom, and each of the C1-8 alkylene group, the C2-8 alkenylene group and the C2-8 alkynylene group may be substituted by 1 to 8 halogen atoms;

[8] the compound according to any one of items [1] to [7], or a pharmaceutically acceptable salt thereof, wherein $R^5$ represents a C3-6 carbocyclic ring or a 3- to 6-membered heterocyclic ring, wherein each of the C3-6 carbocyclic ring and the 3- to 6-membered heterocyclic ring may be substituted by 1 to 5 $R^{22}$s;

[9] the compound according to any one of items [1] to [8], or a pharmaceutically acceptable salt thereof, wherein the ring A is a benzene ring or a pyrrole ring;

[10] the compound according to any one of items [1] to [9], or a pharmaceutically acceptable salt thereof, wherein the ring A is a pyrrole ring and Y is a bond;

[11] the compound according to any one of items [1] to [9], or a pharmaceutically acceptable salt thereof, wherein the ring A is a benzene ring and Y is an oxygen atom;

[12] the compound according to item [1], or a pharmaceutically acceptable salt thereof, wherein the compound is selected from:

(1) rel-(1R,2S)-2-[3-({[1-sec-butyl-5-(3-phenylpropyl)-1H-pyrrole-2-carbonyl]amino)-4-(trifluoromethyl)phenyl]cyclopropanecarboxylic acid;

(2) rel-(1R,2S)-2-{3-[({1-[(2S)-2-butanyl]-5-(3-phenylpropyl)-1H-pyrrol-2-yl}carbonyl)amino]-4-(trifluoromethyl)phenyl}cyclopropanecarboxylic acid;

(3) rel-(1R,2S)-2-{3-[({1-[(2S)-2-butanyl]-5-(3-phenylpropyl)-1H-pyrrol-2-yl}carbonyl)amino]-5-methylphenyl}cyclopropanecarboxylic acid;

(4) rel-(1R,2R)-2-{3-[({1-[(2S)-2-butanyl]-5-(3-phenylpropyl)-1H-pyrrol-2-yl}carbonyl)amino]-5-methylphenyl}cyclopropanecarboxylic acid;

(5) rel-(1R,2S)-2-{5-[({1-[(2S)-2-butanyl]-5-(3-phenylpropyl)-1H-pyrrol-2-yl}carbonyl)amino]-2-(trifluoromethyl)phenyl}cyclopropanecarboxylic acid;

(6) rel-(1R,2R)-2-{5-[({1-[(2S)-2-butanyl]-5-(3-phenylpropyl)-1H-pyrrol-2-yl}carbonyl)amino]-2-(trifluoromethyl)phenyl}cyclopropanecarboxylic acid;

(7) (1S,2R)-2-[3-({[1-isopropyl-5-(3-phenylpropyl)-1H-pyrrol-2-yl]carbonyl}amino)-4-(trifluoromethyl)phenyl]cyclopropanecarboxylic acid;

(8) (1R,2R)-2-[3-({[1-isopropyl-5-(3-phenylpropyl)-1H-pyrrol-2-yl]carbonyl}amino)-4-(trifluoromethyl)phenyl]cyclopropanecarboxylic acid;

(9) (1R,2S)-2-{3-[({1-[(2S)-2-butanyl]-5-(3-phenylpropyl)-1H-pyrrol-2-yl}carbonyl)amino]-4-methoxyphenyl}cyclopropanecarboxylic acid;

(10) (1S,2R)-2-{3-[({1-[(2S)-2-butanyl]-5-(3-phenylpropyl)-1H-pyrrol-2-yl}carbonyl)amino]-4-(trifluoromethyl)phenyl}cyclopropanecarboxylic acid;

(11) (1R,2S)-2-{3-[({1-[(2S)-2-butanyl]-5-(3-phenylpropyl)-1H-pyrrol-2-yl}carbonyl)amino]-4-(trifluoromethyl)phenyl}cyclopropanecarboxylic acid;

(12) (1R,2S)-2-{3-[({1-[(2S)-2-butanyl]-5-(3-phenylpropyl)-1H-pyrrol-2-yl}carbonyl)amino]-4-chlorophenyl}cyclopropanecarboxylic acid;

(13) (1R,2S)-2-{3-[({5-[2-(benzyloxy)ethyl]-1-[(2S)-2-butanyl]-1H-pyrrol-2-yl}carbonyl)amino]-4-(trifluoromethyl)phenyl}cyclopropanecarboxylic acid;

(14) rel-(1R,2S)-2-[3-{[(1-[(2S)-2-butanyl]-5-{2-[(2-fluoro-4-pyridinyl)oxy]ethyl}-1H-pyrrol-2-yl)carbonyl]amino}-4-(trifluoromethyl)phenyl]cyclopropanecarboxylic acid;

(15) (1R,2S)-2-[3-{[(1-[(2S)-2-butanyl]-5-{2-[(2-chloro-6-fluoro-4-pyridinyl)oxy]ethyl}-1H-pyrrol-2-yl)carbonyl]amino}-4-(trifluoromethyl)phenyl]cyclopropanecarboxylic acid;

(16) (1R,2S)-2-{3-[({1-[(2S)-2-butanyl]-5-[2-(2-chloro-3,5-difluorophenoxy)ethyl]-1H-pyrrol-2-yl}carbonyl)amino]-4-(trifluoromethyl)phenyl}cyclopropanecarboxylic acid;

(17) (1R,2S)-2-{3-[({1-[(2S)-2-butanyl]-5-[2-(2,4-difluorophenoxy)ethyl]-1H-pyrrol-2-yl}carbonyl)amino]-4-(trifluoromethyl)phenyl}cyclopropanecarboxylic acid;

(18) (1R,2S)-2-[3-{[(1-[(2S)-2-butanyl]-5-{2-[(1-methyl-1H-pyrazol-4-yl)oxy]ethyl}-1H-pyrrol-2-yl)carbonyl]amino}-4-(trifluoromethyl)phenyl]cyclopropanecarboxylic acid;

(19) rel-(1R,2S)-2-[3-{[2,6-dimethyl-4-(2-phenylethoxy)benzoyl]amino}-4-(trifluoromethyl)phenyl]cyclopropanecarboxylic acid;

(20) (1R,2S)-2-[3-{[2,6-dimethyl-4-(3-phenylpropyl)benzoyl]amino}-4-(trifluoromethyl)phenyl]cyclopropanecarboxylic acid;

(21) (1R,2S)-2-[3-({4-[2-(2,4-difluorophenyl)ethoxy]-2,6-dimethylbenzoyl}amino)-4-(trifluoromethyl)phenyl]cyclopropanecarboxylic acid;

(22) rel-(1R,2S)-2-(2,3-dichloro-5-{[2,6-dimethyl-4-(2-phenylethoxy)benzoyl]amino}-4-fluorophenyl)cyclopropanecarboxylic acid;

(23) rel-(1R,2R)-2-(2,3-dichloro-5-{[2,6-dimethyl-4-(2-phenylethoxy)benzoyl]amino}-4-fluorophenyl)cyclopropanecarboxylic acid;

(24) (1R,2S)-2-[2-chloro-5-{[2,6-dimethyl-4-(2-phenylethoxy)benzoyl]amino}-4-(trifluoromethyl)phenyl]cyclopropanecarboxylic acid;

(25) (1R,2S)-2-(4-chloro-3-{[2,6-dimethyl-4-(2-phenylethoxy)benzoyl]amino}phenyl)cyclopropanecarboxylic acid;

(26) rel-(1R,2S)-2-(2,3-dichloro-5-{[2,6-dimethyl-4-(2-phenylethoxy)benzoyl]amino}phenyl)cyclopropanecarboxylic acid;

(27) rel-(1R,2R)-2-(2,3-dichloro-5-{[2,6-dimethyl-4-(2-phenylethoxy)benzoyl]amino}phenyl)cyclopropanecarboxylic acid;

(28) (1R,2S)-2-[3-{[2,6-dimethyl-4-(2-phenylethoxy)benzoyl]amino}-4-(trifluoromethyl)phenyl]cyclopropanecarboxylic acid;

(29) (1S,2R)-2-[3-{[2,6-dimethyl-4-(2-phenylethoxy)benzoyl]amino}-4-(trifluoromethyl)phenyl]cyclopropanecarboxylic acid;

(30) (1R,2S)-2-[3-({2,6-dimethyl-4-[2-(1-methyl-1H-pyrazol-4-yl)ethoxy]benzoyl}amino)-4-(trifluoromethyl)phenyl]cyclopropanecarboxylic acid;
(31) (1R,2S)-2-[3-{[4-(2-cyclopropylethoxy)-2,6-dimethylbenzoyl]amino}-4-(trifluoromethyl)phenyl]cyclopropanecarboxylic acid;
(32) (1R,2S)-2-{3-[(2,6-dimethyl-4-propoxybenzoyl)amino]-4-(trifluoromethyl)phenyl}cyclopropanecarboxylic acid;
(33) (1R,2S)-2-[3-{[4-(hexyloxy)-2,6-dimethylbenzoyl]amino}-4-(trifluoromethyl)phenyl]cyclopropanecarboxylic acid;
(34) (1R,2S)-2-[3-{[4-(benzyloxy)-2,6-dimethylbenzoyl]amino}-4-(trifluoromethyl)phenyl]cyclopropanecarboxylic acid;
(35) (1R,2S)-2-[3-{[4-(2-methoxyethoxy)-2,6-dimethylbenzoyl]amino}-4-(trifluoromethyl)phenyl]cyclopropanecarboxylic acid;
(36) (1R,2S)-2-[3-({2,6-dimethyl-4-[2-(tetrahydro-2H-pyran-2-yl)ethoxy]benzoyl}amino)-4-(trifluoromethyl)phenyl]cyclopropanecarboxylic acid;
(37) (1R,2S)-2-[3-({4-[2-(2-furyl)ethoxy]-2,6-dimethylbenzoyl}amino)-4-(trifluoromethyl)phenyl]cyclopropanecarboxylic acid;
(38) (1R,2S)-2-[3-({4-[2-(2-chlorophenyl)ethoxy]-2,6-dimethylbenzoyl}amino)-4-(trifluoromethyl)phenyl]cyclopropanecarboxylic acid;
(39) (1R,2S)-2-[3-({4-[2-(3-chlorophenyl)ethoxy]-2,6-dimethylbenzoyl}amino)-4-(trifluoromethyl)phenyl]cyclopropanecarboxylic acid;
(40) (1R,2S)-2-[3-({4-[2-(1H-imidazol-1-yl)ethoxy]-2,6-dimethylbenzoyl}amino)-4-(trifluoromethyl)phenyl]cyclopropanecarboxylic acid;
(41) (1R,2S)-2-[3-({4-[2-(2,6-difluorophenyl)ethoxy]-2,6-dimethylbenzoyl}amino)-4-(trifluoromethyl)phenyl]cyclopropanecarboxylic acid;
(42) (1R,2S)-2-[3-({4-[2-(3,5-difluorophenyl)ethoxy]-2,6-dimethylbenzoyl}amino)-4-(trifluoromethyl)phenyl]cyclopropanecarboxylic acid;
(43) (1R,2S)-2-[3-({4-[(6-chloro-2-pyrazinyl)oxy]-2,6-dimethylbenzoyl}amino)-4-(trifluoromethyl)phenyl]cyclopropanecarboxylic acid;
(44) (1R,2S)-2-[3-{[4-(6-fluoro-3-pyridinyl)-2,6-dimethylbenzoyl]amino}-4-(trifluoromethyl)phenyl]cyclopropanecarboxylic acid;
(45) (1R,2S)-2-[3-({4-[2-(4-hydroxyphenyl)ethoxy]-2,6-dimethylbenzoyl}amino)-4-(trifluoromethyl)phenyl]cyclopropanecarboxylic acid;
(46) 3-[3-{[2,6-dimethyl-4-(2-phenylethoxy)benzoyl]amino}-4-(trifluoromethyl)phenyl]propanoic acid;
(47) 3-[3-{[2,6-dimethyl-4-(2-phenylethoxy)benzoyl]amino}-4-(trifluoromethyl)phenyl]butanoic acid;
(48) 3-[3-{[2,6-dimethyl-4-(2-phenylethoxy)benzoyl]amino}-4-(trifluoromethyl)phenyl]-2-methylpropanoic acid;
(49) (1R,2S)-2-[3-{[2,6-dimethyl-4-(2-phenylethoxy)benzoyl]amino}-4-(trifluoromethyl)phenyl]cyclobutanecarboxylic acid; or
(50) (1R,2R)-2-[3-{[2,6-dimethyl-4-(2-phenylethoxy)benzoyl]amino}-4-(trifluoromethyl)phenyl]-1-methylcyclopropanecarboxylic acid;

[13] the compound according to item [1], or a pharmaceutically acceptable salt thereof, wherein the compound is selected from:
(1) (1R,2S)-2-[3-{[2-methyl-4-(2-phenylethoxy)benzoyl]amino}-4-(trifluoromethyl)phenyl]cyclopropanecarboxylic acid;
(2) (1R,2S)-2-[3-{[2-chloro-4-(2-phenylethoxy)benzoyl]amino}-4-(trifluoromethyl)phenyl]cyclopropanecarboxylic acid;
(3) (1R,2S)-2-[3-{[4-(2-phenylethoxy)-2-(trifluoromethyl)benzoyl]amino}-4-(trifluoromethyl)phenyl]cyclopropanecarboxylic acid;
(4) (1R,2S)-2-[3-{[4-(1H-indazol-5-ylmethoxy)-2,6-dimethylbenzoyl]amino}-4-(trifluoromethyl)phenyl]cyclopropanecarboxylic acid;
(5) (1R,2S)-2-[3-{[2,6-dimethyl-4-(1,2,3,4-tetrahydro-1-naphthalenylmethoxy)benzoyl]amino}-4-(trifluoromethyl)phenyl]cyclopropanecarboxylic acid;
(6) (1R,2S)-2-[3-({2,6-dimethyl-4-[2-(3-pyridinyl)ethoxy]benzoyl}amino)-4-(trifluoromethyl)phenyl]cyclopropanecarboxylic acid;
(7) (1R,2S)-2-[3-({2,6-dimethyl-4-[2-(4-pyridinyl)ethoxy]benzoyl}amino)-4-(trifluoromethyl)phenyl]cyclopropanecarboxylic acid;
(8) (1R,2S)-2-[3-({2,6-dimethyl-4-[2-(2-pyridinyl)ethoxy]benzoyl}amino)-4-(trifluoromethyl)phenyl]cyclopropanecarboxylic acid;
(9) (1R,2S)-2-[3-({4-[2-(2-chloro-1H-imidazol-1-yl)ethoxy]-2,6-dimethylbenzoyl}amino)-4-(trifluoromethyl)phenyl]cyclopropanecarboxylic acid;
(10) (1R,2S)-2-[3-({4-[2-(2-fluorophenyl)ethoxy]-2,6-dimethylbenzoyl}amino)-4-(trifluoromethyl)phenyl]cyclopropanecarboxylic acid;
(11) (1R,2S)-2-[3-({4-[2-(3-fluorophenyl)ethoxy]-2,6-dimethylbenzoyl}amino)-4-(trifluoromethyl)phenyl]cyclopropanecarboxylic acid;
(12) (1R,2S)-2-[3-({4-[2-(4-fluorophenyl)ethoxy]-2,6-dimethylbenzoyl}amino)-4-(trifluoromethyl)phenyl]cyclopropanecarboxylic acid;
(13) (1R,2S)-2-[3-{[2,6-dimethyl-4-(3,3,3-trifluoropropoxy)benzoyl]amino}-4-(trifluoromethyl)phenyl]cyclopropanecarboxylic acid;
(14) (1R,2S)-2-[3-{[2,6-dimethyl-4-(3,3,3-trifluoro-2-methylpropoxy)benzoyl]amino}-4-(trifluoromethyl)phenyl]cyclopropanecarboxylic acid;
(15) (1R,2S)-2-{3-[(2,6-dimethyl-4-{[6-(trifluoromethyl)-2-pyridinyl]oxy}benzoyl)amino]-4-(trifluoromethyl)phenyl}cyclopropanecarboxylic acid;
(16) (1R,2S)-2-[3-{[2,6-dimethyl-4-(pyrazolo[1,5-a]pyrimidin-5-yloxy)benzoyl]amino}-4-(trifluoromethyl)phenyl]cyclopropanecarboxylic acid;
(17) rel-(1R,2S)-2-(3-{[2,6-dimethyl-4-(2-phenylethoxy)benzoyl]amino}-4-methylphenyl)cyclopropanecarboxylic acid;
(18) (1R,2S)-2-[3-{[4-(benzyloxy)-2-isopropylbenzoyl]amino}-4-(trifluoromethyl)phenyl]cyclopropanecarboxylic acid;
(19) (1R,2S)-2-[3-{[2-isopropyl-4-(2-phenylethoxy)benzoyl]amino}-4-(trifluoromethyl)phenyl]cyclopropanecarboxylic acid;
(20) (1R,2S)-2-[3-{[2-isopropyl-4-(3-phenylpropoxy)benzoyl]amino}-4-(trifluoromethyl)phenyl]cyclopropanecarboxylic acid;
(21) (1R,2S)-2-[3-{[3-(benzyloxy)-2-isopropylbenzoyl]amino}-4-(trifluoromethyl)phenyl]cyclopropanecarboxylic acid;
(22) (1R,2S)-2-[3-{[2-isopropyl-3-(2-phenylethoxy)benzoyl]amino}-4-(trifluoromethyl)phenyl]cyclopropanecarboxylic acid;
(23) (1R,2S)-2-[3-{[2-isopropyl-3-(3-phenylpropoxy)benzoyl]amino}-4-(trifluoromethyl)phenyl]cyclopropanecarboxylic acid;

(24) (1R,2S)-2-[4-(trifluoromethyl)-3-{[2,3,5-trimethyl-4-(2-phenylethoxy)benzoyl]amino}phenyl]cyclopropanecarboxylic acid;
(25) (1R,2S)-2-[3-({[3-isopropyl-1-(3-phenylpropyl)-1H-pyrazol-4-yl]carbonyl}amino)-4-(trifluoromethyl)phenyl]cyclopropanecarboxylic acid;
(26) (1R,2S)-2-[3-({[5-isopropyl-1-(3-phenylpropyl)-1H-pyrazol-4-yl]carbonyl}amino)-4-(trifluoromethyl)phenyl]cyclopropanecarboxylic acid;
(27) (1R,2S)-2-[3-({[2,6-dimethyl-4-(2-phenylethoxy)phenyl]carbonothioyl}amino)-4-(trifluoromethyl)phenyl]cyclopropanecarboxylic acid;
(28) (1R,2S)-2-[3-({[4-(2-cyclopropylethoxy)-2,6-dimethylphenyl]carbonothioyl}amino)-4-(trifluoromethyl)phenyl]cyclopropanecarboxylic acid;
(29) (1R,2S)-2-[3-({[2-sec-butyl-1-(3-phenylpropyl)-1H-pyrrol-3-yl]carbonyl}amino)-4-(trifluoromethyl)phenyl]cyclopropanecarboxylic acid;
(30) (1R,2S)-2-[3-({[2-isopropyl-1-(3-phenylpropyl)-1H-pyrrol-3-yl]carbonyl}amino)-4-(trifluoromethyl)phenyl]cyclopropanecarboxylic acid; or
(31) (1R,2S)-2-[3-({[2-(2-methyl-2-propanyl)-1-(3-phenylpropyl)-1H-pyrrol-3-yl]carbonyl}amino)-4-(trifluoromethyl)phenyl]cyclopropanecarboxylic acid;

[14] a pharmaceutical composition comprising the compound according to any one of items [1] to [13] or a pharmaceutically acceptable salt thereof as an active ingredient, and further comprising a pharmaceutically acceptable carrier;

[15] the pharmaceutical composition according to item [14], wherein the pharmaceutical composition is an $EP_2$ receptor antagonist;

[16] the pharmaceutical composition according to item [14] or [15], wherein the pharmaceutical composition is a therapeutic and/or prophylactic agent for a disease associated with the activation of an $EP_2$ receptor;

[17] the pharmaceutical composition according to item [16], wherein the disease associated with the activation of an $EP_2$ receptor is endometriosis, uterine fibroids, hypermenorrhea, adenomyosis, dysmenorrhea, chronic pelvic pain syndrome, cancer, inflammatory pain, neuropathic pain, headache, migraine, postoperative pain, interstitial cystitis, leiomyoma, irritable colon syndrome, Alzheimer's disease, Parkinson's disease, amyotrophic lateral sclerosis, multiple sclerosis, rheumatism, osteoarthritis, gout, an allergic disease, hypertension, brain dysfunction, ischemia, stroke, a kidney disease, transplant rejection, atherosclerosis, an ischemic heart disease, acne vulgaris, asthma, prostatitis, glomerulonephritis, sarcoidosis, vasculitis, or an autoimmune disease;

[18] the pharmaceutical composition according to item [16] or [17], wherein the disease associated with the activation of an $EP_2$ receptor is cancer, and the cancer is breast cancer, ovarian cancer, colorectal cancer, lung cancer, prostate cancer, head and neck cancer, lymphoma, uveal melanoma, thymoma, mesothelioma, esophageal cancer, stomach cancer, duodenal cancer, hepatocellular carcinoma, bile duct cancer, gallbladder cancer, pancreatic cancer, renal cell carcinoma, renal pelvis/ureteral cancer, bladder cancer, penile cancer, testicular cancer, uterine cancer, vaginal cancer, vulvar cancer, skin cancer (e.g., malignant melanoma), malignant bone tumor, soft tissue sarcoma, chondrosarcoma, leukemia, myelodysplastic syndrome, brain tumor or multiple myeloma;

[19] the pharmaceutical composition according to any one of items [14] to [18], wherein the pharmaceutical composition is administered in combination with at least one component selected from an alkylating agent, an antimetabolic agent, an anticancer antibiotic, a plant-derived preparation, a hormonal agent, a platinum compound, a topoisomerase inhibitor, a kinase inhibitor, an anti-CD20 antibody, an anti-HER2 antibody, an anti-EGFR antibody, an anti-VEGF antibody, a proteasome inhibitor, an HDAC inhibitor and an immunomodulatory drug;

[20] a method for preventing and/or treating a disease associated with the activation of an $EP_2$ receptor, the method comprising administering the compound according to any one of items [1] to [13], or a pharmaceutically acceptable salt thereof or the pharmaceutical composition according to item [14] or [15], to a patient in need of prevention and/or treatment of a disease associated with the activation of an $EP_2$ receptor;

[21] the compound according to any one of items [1] to [13] or a pharmaceutically acceptable salt thereof, for use in the prevention and/or treatment of a disease associated with the activation of an $EP_2$ receptor; and

[22] a use of the compound according to any one of items [1] to [13] or a pharmaceutically acceptable salt thereof, for the production of a preventive and/or therapeutic agent for a disease associated with the activation of an $EP_2$ receptor.

Advantageous Effects of Invention

The compound of the present invention has a potent antagonistic activity against an $EP_2$ receptor, and also has excellent pharmacokinetic properties (e.g., solubility and liver microsomal stability). Therefore, the compound of the present invention can be a prophylactic and/or therapeutic agent for a disease associated with the activation of an $EP_2$ receptor.

BRIEF DESCRIPTION OF DRAWING

The FIGURE shows the anti-tumor effect of the compound of the present invention in an allogenic transplantation model of a mouse colorectal cancer cell line CT26.

DESCRIPTION OF EMBODIMENTS

Hereinbelow, the present invention will be described in detail.

The term "halogen atom" as used herein is a fluorine atom, a chlorine atom, a bromine atom or an iodine atom.

The term "C1-4 alkyl group" as used herein is a methyl group, an ethyl group, a propyl group, a butyl group, or an isomer thereof.

The term "C1-6 alkyl group" as used herein is a methyl group, an ethyl group, a propyl group, a butyl group, a pentyl group, a hexyl group or an isomer thereof.

The term "C2-6 alkenyl group" as used herein refers to, for example, a C2-6 alkenyl group having one to two double bonds, and examples thereof include an ethenyl group, a propenyl group, a butenyl group, a butadienyl group, a pentenyl group, a pentadienyl group, a hexenyl group, a hexadienyl group and isomers thereof.

The term "C2-6 alkynyl group" as used herein refers to, for example, a C2-6 alkynyl group having one to two triple bonds, and examples thereof include an ethynyl group, a propynyl group, a butynyl group, a butadiynyl group, a pentynyl group, a pentadiynyl group, a hexynyl group, a hexadiynyl group, and isomers thereof.

The term "C1-4 alkylene group" as used herein is a methylene group, an ethylene group, a propylene group, a butylene group, or an isomer thereof.

The term "C1-8 alkylene group" as used herein is a methylene group, an ethylene group, a propylene group, a butylene group, a pentylene group, a hexylene group, a heptylene group, an octylene group, or an isomer thereof.

The term "C2-8 alkenylene group" as used herein refers to, for example, a C2-6 alkenylene group having one to two double bonds, and examples thereof include an ethenylene group, a propenylene group, a butenylene group, a butadienylene group, a pentenylene group, a pentadienylene group, a hexenylene group, a hexadienylene group, a heptenylene group, a heptadienylene group, an octenylene group, an octadienylene group and isomers thereof.

The term "C2-8 alkynylene group" as used herein refers to, for example, a C2-8 alkynylene group having one to two triple bonds, and examples thereof include an ethynylene group, a propynylene group, a butynylene group, a butadiynylene group, a pentynylene group, a pentadinylene group, a hexynylene group, a hexadiynylene group, a heptynylene group, a heptadiynylene group, an octynylene group, an octadiynylene group, and an isomer thereof.

The term "C1-4 alkoxy group" as used herein is a methoxy group, an ethoxy group, a propoxy group, a butoxy group, or an isomer thereof.

The term "C1-6 alkoxy group" as used herein refers to a methoxy group, an ethoxy group, a propoxy group, a butoxy group, a pentyloxy group, a hexyloxy group, or an isomer thereof.

The term "C1-6 alkylthio group" as used herein is a methylthio group, an ethylthio group, a propylthio group, a butylthio group, a pentylthio group, a hexylthio group, or an isomer thereof.

The term "C1-6 alkylsulfinyl group" as used herein is a methylsulfinyl group, an ethylsulfinyl group, a propylsulfinyl group, a butylsulfinyl group, a pentylsulfinyl group, a hexylsulfinyl group, or an isomer thereof.

The term "C1-6 alkylsulfonyl group" as used herein is a methylsulfonyl group, an ethylsulfonyl group, a propylsulfonyl group, a butylsulfonyl group, a pentylsulfonyl group, a hexylsulfonyl group, or an isomer thereof.

The term "C3-6 cycloalkyl group" as used herein is a cyclopropyl group, a cyclobutyl group, a cyclopentyl group, or a cyclohexyl group.

The term "C3-6 cycloalkyloxy group" as used herein is a cyclopropyloxy group, a cyclobutyloxy group, a cyclopentyloxy group, or a cyclohexyloxy group.

The term "C3-6 cycloalkylthio group" as used herein is a cyclopropylthio group, a cyclobutylthio group, a cyclopentylthio group, or a cyclohexylthio group.

The term "C3-6 cycloalkylsulfinyl group" as used herein is a cyclopropylsulfinyl group, a cyclobutylsulfinyl group, a cyclopentylsulfinyl group, or a cyclohexylsulfinyl group.

The term "C3-6 cycloalkylsulfonyl group" as used herein is a cyclopropylsulfonyl group, a cyclobutylsulfonyl group, a cyclopentylsulfonyl group, or a cyclohexylsulfonyl group.

The term "C1-6 alkoxycarbonyl group" as used herein is a methoxycarbonyl group, an ethoxycarbonyl group, a propoxycarbonyl group, a butoxycarbonyl group, a pentyloxycarbonyl group, a hexyloxycarbonyl group, or an isomer thereof.

The term "C1-4 acyl group" as used herein is a methanoyl group, an ethanoyl group, a propanoyl group, a butanoyl group, or an isomer thereof.

The term "C2-6 acyl group" as used herein is an ethanoyl group, a propanoyl group, a butanoyl group, a pentanoyl group, a hexanoyl group, or an isomer thereof.

The term "C2-6 acyloxy group" as used herein is an ethanoyloxy group, a propanoyloxy group, a butanoyloxy group, a pentanoyloxy group, a hexanoyloxy group, or an isomer thereof.

The term "C3-6 saturated carbocyclic ring" as used herein is, for example, a cyclopropane ring, a cyclobutene ring, a cyclopentane ring, or a cyclohexane ring.

The term "5-membered nitrogen-containing aromatic heterocyclic ring" as used herein refers to a 5-membered aromatic heterocyclic ring containing one or more nitrogen atoms, and examples thereof include a pyrrole ring, an imidazole ring, a triazole ring, a pyrazole ring, an oxazole ring, an isoxazole ring, a thiazole ring, and an isothiazole ring.

The term "5- to 6-membered nitrogen-containing aromatic heterocyclic ring" as used herein refers to a 5-membered or 6-membered aromatic heterocyclic ring containing one or more nitrogen atoms, and examples thereof include a pyrrole ring, an imidazole ring, a triazole ring, a pyrazole ring, a pyridine ring, a pyrazine ring, a pyrimidine ring, a pyridazine ring, an oxazole ring, an isoxazole ring, a thiazole ring, and an isothiazole ring.

The term "5- to 6-membered cyclic group" as used herein refers to a C5-6 carbocyclic ring or a 5- to 6-membered heterocyclic ring.

Examples of the C5-6 carbocyclic ring include cyclopentane, cyclohexane, cyclopentene, cyclohexene, cyclopentadiene, cyclohexadiene, and benzene.

Examples of the 5- to 6-membered heterocyclic ring include a pyrrole ring, an imidazole ring, a triazole ring, a tetrazole ring, a pyrazole ring, a pyridine ring, a pyrazine ring, a pyrimidine ring, a pyridazine ring, a furan ring, a pyran ring, a thiophene ring, a thiopyran ring, an oxazole ring, an isoxazole ring, a thiazole ring, an isothiazole ring, a furazan ring, an oxadiazole ring, an oxazine ring, an oxadiazine ring, a thiadiazole ring, a thiazine ring, a thiadiazine ring, a pyrroline ring, a pyrrolidine ring, an imidazoline ring, an imidazolidine ring, a triazoline ring, a triazolidine ring, a tetrazoline ring, a tetrazolidine ring, a pyrazoline ring, a pyrazolidine ring, a dihydropyridine ring, a tetrahydropyridine ring, a piperidine ring, a dihydropyrazine ring, a tetrahydropyrazine ring, a piperazine ring, a dihydropyrimidine ring, a tetrahydropyrimidine ring, a perhydropyrimidine ring, a dihydropyridazine ring, a tetrahydropyridazine ring, a perhydropyridazine ring, a dihydrofuran ring, a tetrahydrofuran ring, a dihydropyran ring, a tetrahydropyran ring, a dihydrothiophene ring, a tetrahydrothiophene ring, a dihydrothiopyran ring, a tetrahydrothiopyran ring, a dihydrooxazole ring, a tetrahydrooxazole(oxazolidine) ring, a dihydroisoxazole ring, a tetrahydroisoxazole(isoxazolidine) ring, a dihydrothiazole ring, a tetrahydrothiazole(thiazolidine) ring, a dihydroisothiazole ring, a tetrahydroisothiazole(isothiazolidine) ring, a dihydrofurazan ring, a tetrahydrofurazan ring, a dihydrooxadiazole ring, a tetrahydrooxadiazole(oxadiazolidine) ring, a dihydrooxazine ring, a tetrahydrooxazine ring, a dihydrooxadiazine ring, a tetrahydrooxadiazine ring, a dihydrothiadiazole ring, a tetrahydrothiadiazole(thiadiazolidine) ring, a dihydrothiazine ring, a tetrahydrothiazine ring, a dihydrothiadiazine ring, a tetrahydrothiadiazine ring, a morpholine ring, a thiomorpholine ring, an oxathiane ring, a dioxolane ring, a dioxane ring, a dithiolane ring, and a dithiane ring.

The term "3- to 6-membered cyclic group" as used herein refers to a C3-6 carbocyclic ring or a 3- to 6-membered heterocyclic ring.

Examples of the C3-6 carbocyclic ring include a cyclopropane ring, a cyclobutane ring, a cyclopentane ring, a cyclohexane ring, a cyclobutene ring, a cyclopentene ring, a cyclohexene ring, a cyclobutadiene ring, a cyclopentadiene ring, a cyclohexadiene ring, and a benzene ring.

Examples of the 3- to 6-membered heterocyclic ring is aziridine, azetidine, oxirane, oxetane, thiirane, thietane, the above-mentioned 5- to 6-membered heterocyclic ring or the like.

The term "C3-10 carbocyclic ring" as used herein is, for example, a cyclopropane ring, a cyclobutane ring, a cyclopentane ring, a cyclohexane ring, a cycloheptane ring, a cyclooctane ring, a cyclononane ring, a cyclodecane ring, a cyclobutene ring, a cyclopentene ring, a cyclohexene ring, a cycloheptene ring, a cyclooctene ring, a cyclononene ring, a cyclodecene ring, a cyclobutadiene ring, a cyclopentadiene ring, a cyclohexadiene ring, a cycloheptadiene ring, a cyclooctadiene ring, a benzene ring, a pentalene ring, a perhydropentalene ring, an azulene ring, a perhydroazulene ring, an indene ring, a perhydroindene ring, an indan ring, a naphthalene ring, a dihydronaphthalene ring, a tetrahydronaphthalene ring, and a perhydronaphthalene ring.

The term "3- to 10-membered heterocyclic ring" as used herein is, for example, the above-mentioned 5- to 6-membered heterocyclic ring, and an aziridine ring, an azetidine ring, an oxirane ring, an oxetane ring, a thiirane ring, a thietane ring, an azepine ring, a diazepine ring, an oxepine ring, a thiepine ring, an oxazepine ring, an oxadiazepine ring, a thiazepine ring, a thiadiazepine ring, an indole ring, an isoindole ring, an indolizine ring, a benzofuran ring, an isobenzofuran ring, a benzothiophene ring, an isobenzothiophene ring, a dithianaphthalene ring, an indazole ring, a quinoline ring, an isoquinoline ring, a quinolizine ring, a purine ring, a phthalazine ring, a pteridine ring, a naphthyridine ring, a quinoxaline ring, a quinazoline ring, a cinnoline ring, a benzoxazole ring, a benzothiazole ring, a benzoimidazole ring, a chromene ring, a benzofurazan ring, a benzothiadiazole ring, a benzotriazole ring, a dihydroazepine ring, a tetrahydroazepine ring, a perhydroazepine ring, a dihydrodiazepine ring, a tetrahydrodiazepine ring, a perhydrodiazepine ring, a dihydrooxepine ring, a tetrahydrooxepine ring, a perhydrooxepine ring, a dihydrothiepine ring, a tetrahydrothiepine ring, a perhydrothiepine ring, a dihydroxazepine ring, a tetrahydroxazepine ring, a perhydroxazepine ring, a dihydroxadiazepine ring, a tetrahydroxadiazepine ring, a perhydroxadiazepine ring, a dihydrothiazepine ring, a tetrahydrothiazepine ring, a perhydrothiazepine ring, a dihydrothiadiazepine ring, a tetrahydrothiadiazepine ring, a perhydrothiadiazepine ring, an indoline ring, an isoindoline ring, a dihydrobenzofuran ring, a perhydrobenzofuran ring, a dihydroisobenzofuran ring, a perhydroisobenzofuran ring, a dihydrobenzothiophene ring, a perhydrobenzothiophene ring, a dihydroisobenzothiophene ring, a perhydroisobenzothiophene ring, a dihydroindazole ring, a perhydroindazole ring, a dihydroquinoline ring, a tetrahydroquinoline ring, a perhydroquinoline ring, a dihydroisoquinoline ring, a tetrahydroisoquinoline ring, a perhydroisoquinoline ring, a dihydrophthalazine ring, a tetrahydrophthalazine ring, a perhydrophthalazine ring, a dihydronaphthyridine ring, a tetrahydronaphthyridine ring, a perhydronaphthyridine ring, a dihydroquinoxaline ring, a tetrahydroquinoxaline ring, a perhydroquinoxaline ring, a dihydroquinazoline ring, a tetrahydroquinazoline ring, a perhydroquinazoline ring, a dihydrocinnoline ring, a tetrahydrocinnoline ring, a perhydrocinnoline ring, a benzoxathiane ring, a dihydrobenzooxazine ring, a dihydrobenzothiazine ring, a pyrazinomorpholine ring, a dihydrobenzoxazole ring, a perhydrobenzoxazole ring, a dihydrobenzothiazole ring, a perhydrobenzothiazole ring, a dihydrobenzoimidazole ring, a perhydrobenzoimidazole ring, a dioxaindan ring, a benzodioxane ring, a chroman ring, a benzodithiolane ring, a benzodithiane ring, an azaspiro[4.4]nonane ring, an oxazaspiro[4.4]nonane ring, a dioxaspiro[4.4]nonane ring, an azaspiro[4.5]decane ring, a thiaspiro[4.5]decane ring, a dithiaspiro[4.5]decane ring, a dioxaspiro[4.5]decane ring, an oxazaspiro[4.5]decane ring, an azabicyclo[3.2.1]octane ring, and an oxabicyclo[3.2.1]octane ring.

In the present invention, the compound represented by general formula (I-A) is preferably a compound represented by general formula (I):

(I)

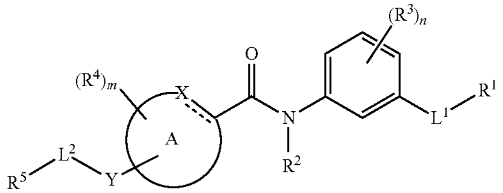

(wherein all symbols have the same meanings as mentioned above) or a pharmaceutically acceptable salt thereof.

In the present invention, the compound represented by general formula (I-A) is preferably a compound represented by general formula (I-a):

(I-a)

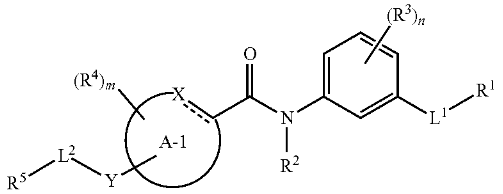

(wherein the ring A-1 represents a benzene ring or a 5-membered nitrogen-containing aromatic heterocyclic ring, and other symbols have the same meanings as mentioned above) or a pharmaceutically acceptable salt thereof.

In the present invention, another preferred embodiment of the compound represented by general formula (I-A) is a compound represented by general formula (I-b):

(I-b)

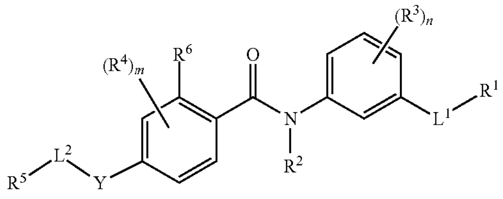

(wherein all symbols have the same meanings as mentioned above) or a pharmaceutically acceptable salt thereof.

In the present invention, another preferred embodiment of the compound represented by general formula (I-A) is a compound represented by general formula (I-c):

(I-c)

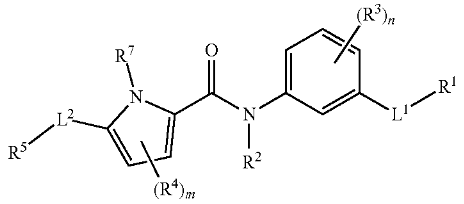

(wherein all symbols have the same meanings as mentioned above) or a pharmaceutically acceptable salt thereof.

In the present invention, the compound represented by general formula (I-A) is more preferably a compound represented by general formula (I-1):

(I-1)

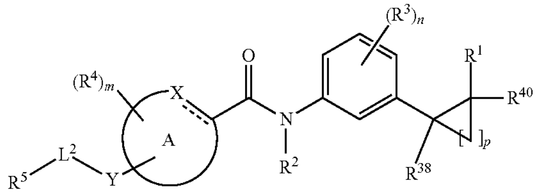

(wherein all symbols have the same meanings as mentioned above) or a pharmaceutically acceptable salt thereof.

In the present invention, another more preferred embodiment of the compound represented by general formula (I-A) is a compound represented by general formula (I-d):

(I-d)

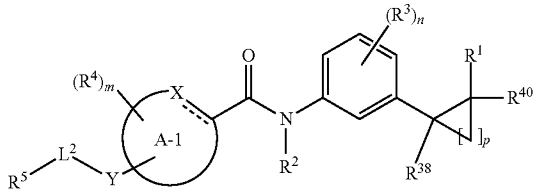

(wherein all symbols have the same meanings as mentioned above) or a pharmaceutically acceptable salt thereof.

In the present invention, another more preferred embodiment of the compound represented by general formula (I-A) is a compound represented by general formula (I-e):

(I-e)

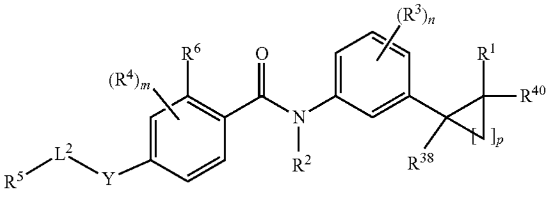

(wherein all symbols have the same meanings as mentioned above) or a pharmaceutically acceptable salt thereof.

In the present invention, another more preferred embodiment of the compound represented by general formula (I-A) is a compound represented by general formula (I-f):

(I-f)

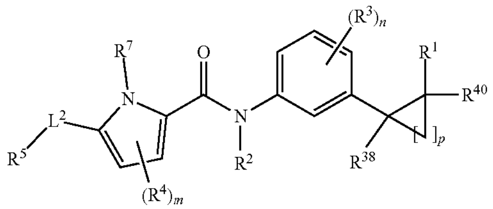

(wherein all symbols have the same meanings as mentioned above) or a pharmaceutically acceptable salt thereof.

In the present invention, another preferred embodiment of the compound represented by general formula (I-A) is a compound represented by general formula (I-g):

(I-g)

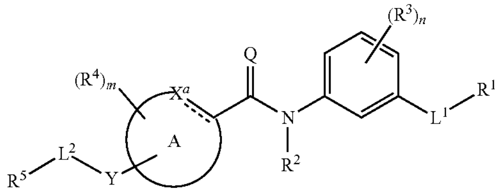

(wherein all symbols have the same meanings as mentioned above) or a pharmaceutically acceptable salt thereof.

In the present invention, another preferred embodiment of the compound represented by general formula (I-A) is a compound represented by general formula (I-h):

(I-h)

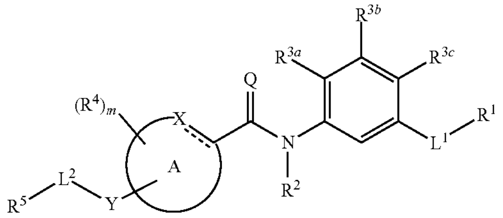

(wherein all symbols have the same meanings as mentioned above) or a pharmaceutically acceptable salt thereof.

In the present invention, another preferred embodiment of the compound represented by general formula (I-A) is a compound represented by general formula (I-B):

(I-B)

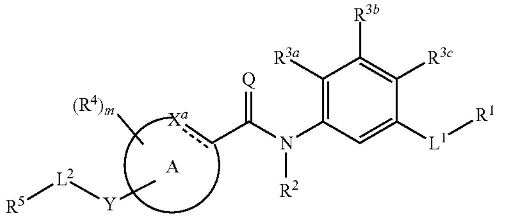

(wherein all symbols have the same meanings as mentioned above) or a pharmaceutically acceptable salt thereof.

In the present invention, another preferred embodiment of the compound represented by general formula (I-A) is a compound represented by general formula (I-i):

(I-i)

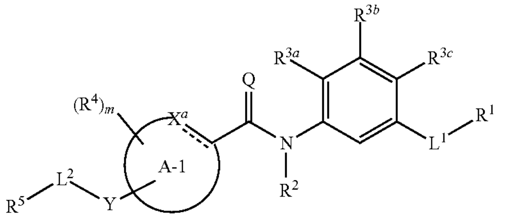

(wherein all symbols have the same meanings as mentioned above) or a pharmaceutically acceptable salt thereof.

In the present invention, another preferred embodiment of the compound represented by general formula (I-A) is a compound represented by general formula (I-i):

(I-j)

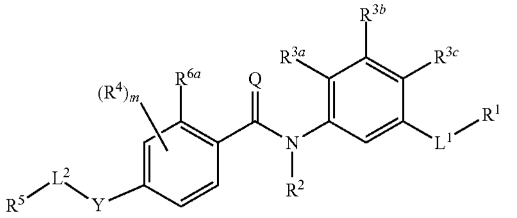

(wherein all symbols have the same meanings as mentioned above) or a pharmaceutically acceptable salt thereof.

In the present invention, another preferred embodiment of the compound represented by general formula (I-A) is a compound represented by general formula (I-k):

(I-k)

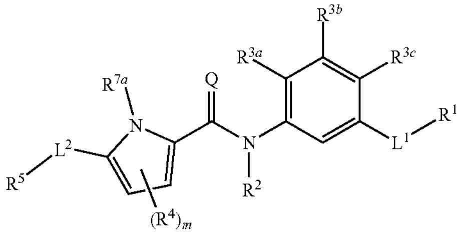

(wherein all symbols have the same meanings as mentioned above) or a pharmaceutically acceptable salt thereof.

In the present invention, another preferred embodiment of the compound represented by general formula (I-A) is a compound represented by general formula (I-L):

(I-L)

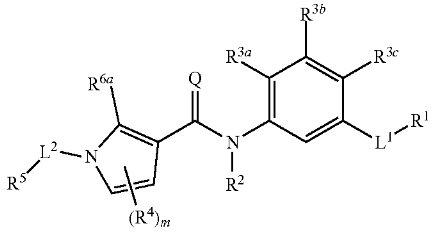

(wherein all symbols have the same meanings as mentioned above) or a pharmaceutically acceptable salt thereof.

In the present invention, the compound represented by general formula (I-A) is more preferably a compound represented by general formula (I-m):

(I-m)

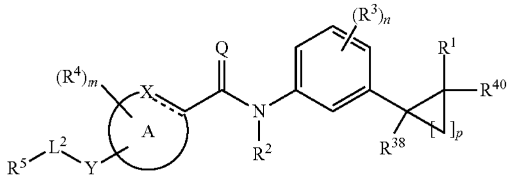

(wherein all symbols have the same meanings as mentioned above) or a pharmaceutically acceptable salt thereof.

In the present invention, the compound represented by general formula (I-A) is more preferably a compound represented by general formula (I-n):

(I-n)

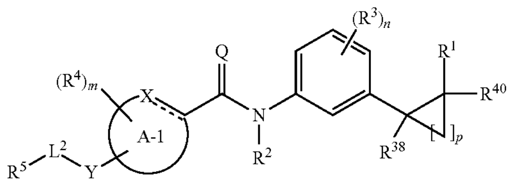

(wherein all symbols have the same meanings as mentioned above) or a pharmaceutically acceptable salt thereof.

In the present invention, the compound represented by general formula (I-A) is more preferably a compound represented by general formula (I-o):

(I-o)

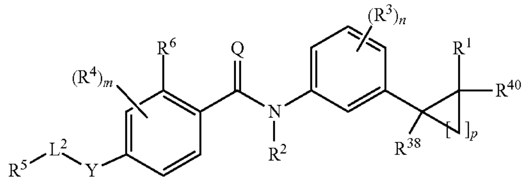

(wherein all symbols have the same meanings as mentioned above) or a pharmaceutically acceptable salt thereof.

In the present invention, the compound represented by general formula (I-A) is more preferably a compound represented by general formula (I-p):

(I-p)

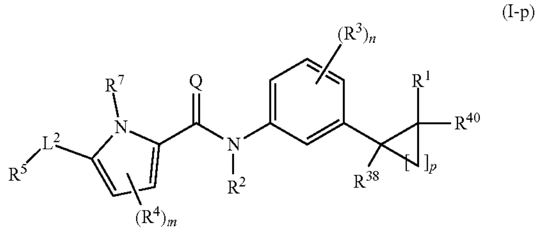

(wherein all symbols have the same meanings as mentioned above) or a pharmaceutically acceptable salt thereof.

In the present invention, the compound represented by general formula (I-A) is more preferably a compound represented by general formula (I-q):

(I-q)

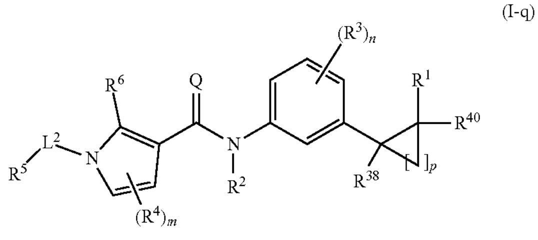

(wherein all symbols have the same meanings as mentioned above) or a pharmaceutically acceptable salt thereof.

In the present invention, the compound represented by general formula (I-A) is still more preferably a compound represented by general formula (I-C):

(I-C)

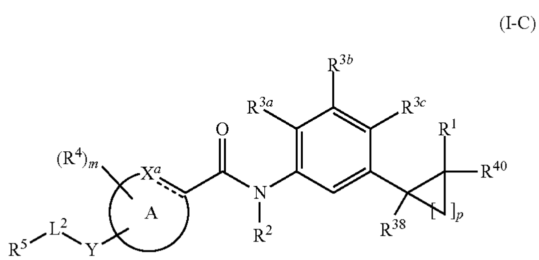

(wherein all symbols have the same meanings as mentioned above) or a pharmaceutically acceptable salt thereof.

In the present invention, the compound represented by general formula (I-A) is preferably a compound represented by general formula (II):

(II)

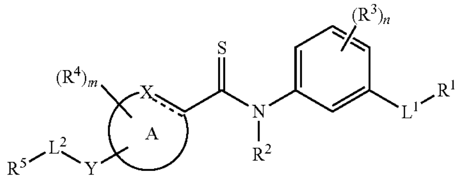

(wherein all symbols have the same meanings as mentioned above) or a pharmaceutically acceptable salt thereof.

In the present invention, $R^1$ is preferably $COOR^{10}$ or $CON^{14}R^{15}$, more preferably $COOR^{10}$, still more preferably COOH.

In the present invention, $R^{10}$ is preferably a hydrogen atom.

In the present invention, $R^2$ is preferably a hydrogen atom.

In the present invention, $R^3$ is preferably a halogen atom, a C1-6 alkyl group which may be substituted by a halogen atom, or a C1-6 alkoxy group which may be substituted by a halogen atom, more preferably a fluorine atom, a chlorine atom, a bromine atom, a methyl group, a methoxy group, or a trifluoromethyl group, most preferably a trifluoromethyl group.

In the present invention, at least one of $R^{3a}$, $R^{3b}$ and $R^{3c}$ represents a substituent other than a hydrogen atom. With respect to the combination of $R^{3a}$, $R^{3b}$ and $R^{3c}$, $R^{3b}$ may be a substituent other than a hydrogen atom and $R^{3a}$ and/or $R^{3c}$ may be a hydrogen atom; or $R^{3c}$ may be a substituent other than a hydrogen atom and $R^{3a}$ and/or $R^{3b}$ may be a hydrogen atom; or each of $R^{3a}$ and $R^{3b}$ may be a substituent other than a hydrogen atom and $R^{3c}$ may be a hydrogen atom; or each of $R^{3a}$ and $R^{3c}$ may be a substituent other than a hydrogen atom and $R^{3b}$ may be a hydrogen atom; or each of $R^{3b}$ and $R^{3c}$ may be a substituent other than a hydrogen atom and $R^{3a}$ may be a hydrogen atom; or each of $R^{3a}$ to $R^{3c}$ may be a substituent other than a hydrogen atom. It is preferred that $R^{3a}$ is a substituent other than a hydrogen atom and $R^{3b}$ and/or $R^{3c}$ is a hydrogen atom. More preferably, $R^{3a}$ is a substituent other than a hydrogen atom, and each of $R^{3b}$ and $R^{3c}$ is a hydrogen atom. The substituent other than a hydrogen atom is preferably a halogen atom, a C1-6 alkyl group which may be substituted by a halogen atom, or a C1-6 alkoxy group which may be substituted by a halogen atom, more preferably a fluorine atom, a chlorine atom, a bromine atom, a methyl group, a methoxy group, or a trifluoromethyl group, most preferably a trifluoromethyl group.

In the present invention, $R^4$ is preferably a halogen atom, a C1-6 alkyl group, or a C1-6 alkoxy group, more preferably a C1-6 alkyl group, still more preferably a methyl group.

In the present invention, $R^5$ is preferably a hydrogen atom, a C3-6 carbocyclic ring, or a 3- to 6-membered heterocyclic ring, more preferably a C3-6 carbocyclic ring or a 3- to 6-membered heterocyclic ring, more preferably a hydrogen atom, a cyclopropane ring, a benzene ring, or a 5- to 6-membered heterocyclic ring, more preferably a cyclopropane ring, a benzene ring, an imidazole ring, a pyrazole ring, a pyridine ring, a furan ring, or a tetrahydropyran ring, most preferably a benzene ring. $R^5$ may be substituted by 1 to 5 $R^{22}$s.

In the present invention, $R^{22}$ is preferably a halogen atom, a hydroxyl group, or a C1-6 alkyl group, more preferably a fluorine atom, a chlorine atom, a hydroxyl group, or a methyl group.

In the present invention, $R^6$ is preferably a halogen atom, or a C1-6 alkyl group which may be substituted by a halogen atom, more preferably a C1-6 alkyl group, still more preferably a methyl or isopropyl group, particularly preferably a methyl group.

In the present invention, $R^{6a}$ is preferably a halogen atom, or a C1-6 alkyl group which may be substituted by a halogen atom, more preferably a C1-6 alkyl group, still more preferably a methyl or isopropyl group, particularly preferably a methyl group.

In the present invention, $R^7$ is preferably a C1-6 alkyl group or a 3- to 6-membered cyclic group, more preferably an isopropyl, 2-butyl, 3-pentyl or a cyclopropyl group, more preferably an isopropyl, 3-pentyl or 2-butyl group, still more preferably a 2-butyl group. When the symbol:

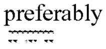

in the ring A is a double bond, $R^7$ is not present.

In the present invention, $R^{7a}$ is preferably a C1-6 alkyl group or a 3- to 6-membered cyclic group, more preferably an isopropyl, 2-butyl, 3-pentyl, or cyclopropyl group, more preferably an isopropyl, 3-pentyl, or 2-butyl group, still more preferably a 2-butyl group. When the symbol:

in the ring A is a double bond, $R^{7a}$ is not present.

In the present invention, $R^{38}$, $R^{39}$, $R^{40}$ and $R^{41}$ preferably independently represent a hydrogen atom or a C1-4 alkyl group.

In the present invention, Q is preferably an oxygen atom.

In the present invention, $L^1$ is preferably

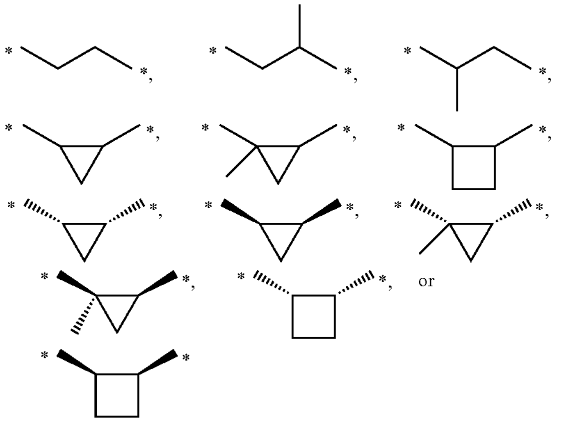

(wherein * represents a bonding site to a benzene ring or $R^1$, wherein the direction of the bonding may be either direction), more preferably

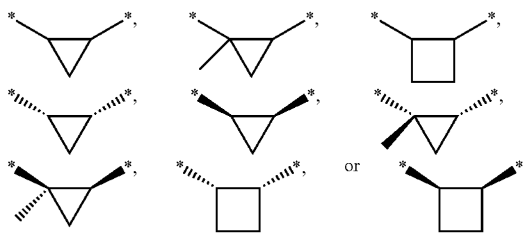

(wherein * represents a bonding site to a benzene ring or $R^1$, wherein the direction of the bonding may be either direction), In the present invention, $L^1$ is preferably a C3-6 saturated carbocyclic ring.

In the present invention, the ring A is preferably a benzene ring or a 5-membered nitrogen-containing aromatic heterocyclic ring, more preferably a benzene, pyrrole or pyrazole ring, particularly preferably a benzene or pyrrole ring.

In the present invention, Y is preferably a bond or an oxygen atom.

In the present invention, the combination of the ring A and Y is preferably a combination in which the ring A is a benzene ring and Y is an oxygen atom, or a combination in which the ring A is a 5-membered nitrogen-containing aromatic heterocyclic ring (more preferably a pyrrole or pyrazole ring, particularly preferably a pyrrole ring) and Y is a bond.

In the present invention, $L^2$ is preferably a bond or a C1-8 alkylene group in which one carbon atom may be replaced by an oxygen atom, more preferably a C1-8 alkylene group in which one carbon atoms may be replaced by an oxygen atom, still more preferably an ethylene group, a propylene group, $—OCH_2CH_2—$ or $—CH_2OCH_2CH_2—$.

In the present invention, the ring A-1 is a benzene, pyrrole, or pyrazole ring, more preferably a benzene or pyrrole ring.

In the present invention, p is preferably 1 or 2, more preferably 1.

In the present invention, m is preferably 0, 1 or 2, more preferably 0 or 1.

In the present invention, n is preferably 1, 2 or 3, more preferably 1.

In the present invention, in general formula (I-A), general formula (I), general formula (I-1), general formula (I-a), general formula (I-b), general formula (I-c), general formula (I-d), general formula (I-e), general formula (I-f), general formula (I-g), general formula (I-h), general formula (I-i), general formula (I-j), general formula (I-k), general formula (I-L), general formula (I-m), general formula (I-n), general formula (I-o), general formula (I-p), general formula (I-q), general formula (I-B), general formula (I-C) or general formula (II) mentioned above, $L^2$ is, each independently, preferably a bond or a C1-8 alkylene group which may contain one oxygen atom, more preferably a C1-8 alkylene group which may contain one oxygen atom, still more preferably an ethylene group, a propylene group, $—OCH_2CH_2—$ or $—CH_2OCH_2CH_2—$; $R^5$ is preferably a C3-6 carbocyclic ring or a 3- to 6-membered heterocyclic ring, wherein each of the C3-6 carbocyclic ring and the 3- to 6-membered heterocyclic ring may be substituted by 1 to 5 $R^{22}$s; $R^1$ is preferably COOH; and $R^2$ is preferably a hydrogen atom.

In the present invention, in general formula (I-A), the combination of $R^1$, $R^2$, $R^3$, $R^4$, $R^5$, Q, ring A, $L^1$, $L^2$, X, Y, n and m is preferably a combination of members which are respectively defined as being preferred for the individual symbols.

In the present invention, in general formula (I), the combination of $R^1$, $R^2$, $R^3$, $R^4$, $R^5$, ring A, $L^1$, $L^2$, X, Y, n and m is preferably a combination of members which are respectively defined as being preferred for the individual symbols.

In the present invention, in general formula (I-1), the combination of $R^1$, $R^2$, $R^3$, $R^4$, $R^5$, $R^{38}$, $R^{40}$, ring A, $L^2$, X, Y, p, n and m is preferably a combination of members which are respectively defined as being preferred for the individual symbols.

In the present invention, in general formula (I-a), the combination of $R^1$, $R^2$, $R^3$, $R^4$, $R^5$, ring A-1, $L^1$, $L^2$, X, Y, n and m is preferably a combination of members which are respectively defined as being preferred for the individual symbols.

In the present invention, in general formula (I-b), the combination of $R^1$, $R^2$, $R^3$, $R^4$, $R^5$, $R^6$, $L^1$, $L^2$, Y, n and m is preferably a combination of members which are respectively defined as being preferred for the individual symbols.

In the present invention, in general formula (I-c), the combination of $R^1$, $R^2$, $R^3$, $R^4$, $R^5$, $R^7$, $L^1$, $L^2$, n and m is preferably a combination of members which are respectively defined as being preferred for the individual symbols.

In the present invention, in general formula (I-d), the combination of $R^1$, $R^2$, $R^3$, $R^4$, $R^5$, $R^{38}$, $R^{40}$, ring A-1, $L^2$, X, Y, p, n and m is preferably a combination of members which are respectively defined as being preferred for the individual symbols.

In the present invention, in general formula (I-e), the combination of $R^1$, $R^2$, $R^3$, $R^4$, $R^5$, $R^6$, $R^{38}$, $R^{40}$, $L^2$, Y, p, n and m is preferably a combination of members which are respectively defined as being preferred for the individual symbols.

In the present invention, in general formula (I-f), the combination of $R^1$, $R^2$, $R^3$, $R^4$, $R^5$, $R^7$, $R^{38}$, $R^{40}$, $L^2$, p, n and m is preferably a combination of members which are respectively defined as being preferred for the individual symbols.

In the present invention, in general formula (I-g), the combination of $R^1$, $R^2$, $R^3$, $R^4$, $R^5$, Q, ring A, $L^1$, $L^2$, $X^a$, Y, n and m is preferably a combination of members which are respectively defined as being preferred for the individual symbols.

In the present invention, in general formula (I-h), the combination of $R^1$, $R^2$, $R^{3a}$, $R^{3b}$, $R^{3c}$, $R^4$, $R^5$, Q, ring A, $L^1$, $L^2$, X, Y and m is preferably a combination of members which are respectively defined as being preferred for the individual symbols.

In the present invention, in general formula (I-i), the combination of $R^1$, $R^2$, $R^{3a}$, $R^{3b}$, $R^{3c}$, $R^4$, $R^5$, Q, ring A-1, $L^1$, $L^2$, $X^a$, Y and m is preferably a combination of members which are respectively defined as being preferred for the individual symbols.

In the present invention, in general formula (I-j), the combination of $R^1$, $R^2$, $R^{3a}$, $R^{3b}$, $R^{3c}$, $R^4$, $R^5$, $R^{6a}$, Q, $L^1$, $L^2$, Y and m is preferably a combination of members which are respectively defined as being preferred for the individual symbols.

In the present invention, in general formula (I-k), the combination of $R^1$, $R^2$, $R^{3a}$, $R^{3b}$, $R^{3c}$, $R^4$, $R^5$, $R^{7a}$, Q, $L^1$, $L^2$ and m is preferably a combination of members which are respectively defined as being preferred for the individual symbols.

In the present invention, in general formula (I-L), the combination of $R^1$, $R^2$, $R^{3a}$, $R^{3b}$, $R^{3c}$, $R^4$, $R^5$, $R^{6a}$, Q, $L^1$, $L^2$ and m is preferably a combination of members which are respectively defined as being preferred for the individual symbols.

In the present invention, in general formula (I-m), the combination of $R^1$, $R^2$, $R^3$, $R^4$, $R^5$, $R^{38}$, $R^{40}$, Q, ring A, $L^2$, X, Y, p, n and m is preferably a combination of members which are respectively defined as being preferred for the individual symbols.

In the present invention, in general formula (I-n), the combination of $R^1$, $R^2$, $R^3$, $R^4$, $R^5$, $R^{38}$, $R^{40}$, Q, ring A-1, $L^2$, X, Y, p, n and m is preferably a combination of members which are respectively defined as being preferred for the individual symbols.

In the present invention, in general formula (I-o), the combination of $R^1$, $R^2$, $R^3$, $R^4$, $R^5$, $R^6$, $R^{38}$, $R^{40}$, Q, $L^2$, Y, p, n and m is preferably a combination of members which are respectively defined as being preferred for the individual symbols.

In the present invention, in general formula (I-p), the combination of $R^1$, $R^2$, $R^3$, $R^4$, $R^5$, $R^7$, $R^{38}$, $R^{40}$, Q, $L^2$, p, n and m is preferably a combination of members which are respectively defined as being preferred for the individual symbols.

In the present invention, in general formula (I-q), the combination of $R^1$, $R^2$, $R^3$, $R^4$, $R^5$, $R^6$, $R^{38}$, $R^{40}$, Q, $L^2$, p, n and m is preferably a combination of members which are respectively defined as being preferred for the individual symbols.

In the present invention, in general formula (I-B), the combination of $R^1$, $R^2$, $R^{3a}$, $R^{3b}$, $R^{3c}$, $R^4$, $R^5$, Q, ring A, $L^1$, $L^2$, $X^a$, Y and m is preferably a combination of members which are respectively defined as being preferred for the individual symbols.

In the present invention, in general formula (I-C), the combination of $R^1$, $R^2$, $R^{3a}$, $R^{3b}$, $R^{3c}$, $R^4$, $R^5$, $R^{38}$, $R^{40}$, ring A, $L^2$, $X^a$, Y, p and m is preferably a combination of members which are respectively defined as being preferred for the individual symbols.

In the present invention, in general formula (II), the combination of $R^1$, $R^2$, $R^3$, $R^4$, $R^5$, ring A, $L^1$, $L^2$, X, Y, n and m is preferably a combination of members which are respectively defined as being preferred for the individual symbols.

In the present invention, most preferred other embodiments of general formula (I-A) are compounds of Examples which are described in the below mentioned section "EXAMPLES" or pharmaceutically acceptable salts thereof.

In the present invention, the isomer includes all of these isomers, unless otherwise specified. For example, each of an alkyl group, an alkoxy group and an alkylene group includes both of a linear form and a branched form thereof. In addition, an isomer in a double bond, a ring or a condensed ring (an E-, Z-, cis- or trans-form), an isomer due to the presence of an asymmetric carbon or the like (an R- or S-form, an α- or β-configuration, an enantiomer, a diastereomer), an optical isomer having an optical rotation (a D-, L-, d- or l-form), a polar body obtained by chromatographic separation (a highly polar body, a poorly polar body), an equilibrium compound and a rotational isomer, and a mixture and a racemic mixture thereof at an arbitrary mixing ratio are also included within the scope of the present invention. In the present invention, the isomer includes all of tautomeric isomers.

In the present invention, as is apparent to persons skilled in the art, the symbol:

means that the bond into the plane of the paper (i.e., an α-configuration), the symbol:

means that the bond out of the plane of the paper (i.e., a β-configuration), and the symbol:

means that the bond is a mixture of the α-configuration and the β-configuration at an arbitrary mixing ratio, unless otherwise stated.

[Salt]

The compound represented by general formula (I-A) can be converted to a salt thereof by a known method.

The salt is a pharmaceutically acceptable salt.

The salt is preferably water-soluble.

Examples of the pharmaceutically acceptable salt include an acid addition salt, an alkali metal salt, an alkaline earth metal salt, an ammonium salt and an amine salt.

Examples of the acid addition salt include: an inorganic acid salt such as a hydrochloric acid salt, a hydrobromic acid salt, a hydroiodic acid salt, a sulfuric acid salt, a phosphoric acid salt and a nitric acid salt; and an organic acid salt such as an acetic acid salt, a lactic acid salt, a tartaric acid salt, a benzoic acid salt, a citric acid salt, a methanesulfonic acid salt, an ethanesulfonic acid salt, a trifluoroacetic acid salt, a benzenesulfonic acid salt, a toluenesulfonic acid salt, an isethionic acid salt, a glucuronic acid salt and a gluconic acid salt.

Examples of the alkali metal salt include a potassium salt and a sodium salt.

Examples of the alkaline earth metal salt include a calcium salt and a magnesium salt.

Examples of the ammonium salt include a tetramethylammonium salt.

Examples of the amine salt include a triethylamine salt, a methylamine salt, a dimethylamine salt, a cyclopentylamine salt, a benzylamine salt, a phenethylamine salt, a piperidine salt, a monoethanolamine salt, a diethanolamine salt, a tris(hydroxymethyl)aminomethane salt, a lysine salt, an arginine salt and a N-methyl-D-glucamine salt.

The compound of the present invention can be converted to an N-oxide form thereof by an arbitrary method. An N-oxide form of the compound represented by general formula (I-A) is a compound having such a structure that a nitrogen atom in the compound represented by general formula (I-A) is oxidized.

The compound represented by general formula (I-A) or a salt thereof may be present in a non-solvated form or a form solvated with a pharmaceutically acceptable solvent such was water and ethanol. The solvate is preferably a hydrate. The compound represented by general formula (I-A) or the salt thereof can be converted to a solvate.

The compound represented by general formula (I-A) may be formed into a cocrystal with a proper cocrystal forming agent. The cocrystal is preferably a pharmaceutically acceptable one that is formed with a pharmaceutically acceptable cocrystal forming agent. A cocrystal is typically defined as a crystal formed by at least two different molecules are bonded through an intermolecular interaction that is different from an ionic bond. The cocrystal may be a complex of a neutral molecule and a salt. The cocrystal can be prepared by a known method, such as melt-crystallization, recrystallization from a solvent, and physical grinding of all of components together. Examples of the proper cocrystal forming agent include those compounds which are described in WO2006/007448.

In the present invention, all of the statements about the compound of the present invention cover those about a compound represented by general formula (I-A), or a salt, N-oxide, solvate (e.g., hydrate) or cocrystal thereof, or an N-oxide, solvate (e.g., hydrate) or cocrystal of a salt of the compound represented by general formula (I-A).

[Prodrug]

The term "prodrug of the compound represented by general formula (I-A)" refers to a compound which can be converted to a compound represented by general formula (I-A) through a reaction with an enzyme, gastric acid or the like in vivo. Examples of the prodrug of the compound represented by general formula (I-A) include: in the case where the compound represented by general formula (I-A) has an amino group, a compound having such a structure that the amino group is acylated, alkylated or phosphorylated (e.g., a compound having such a structure that the amino group in the corresponding compound represented by general formula (I-A) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated or tert-butylated); in the case where the compound represented by general formula (I-A) has a hydroxyl group, a compound having such a structure that the hydroxyl group is acylated, alkylated, phosphorylated or borated (e.g., a compound having such a structure that the hydroxyl group in the corresponding compound represented by general formula (I-A) is acetylated, palmitoylated, propanoylated, pivaloylated, succinylated, fumarylated, alanylated or dimethylaminomethylcarbonylated); and in the case where the compound represented by general formula (I-A) has a carboxyl group, a compound having such a structure that the carboxyl group is esterified or amidated (e.g., a compound having such a structure that the carbonyl group in the corresponding compound represented by general formula (I-A) is ethyl-esterified, phenyl-esterified, carboxymethyl-esterified, dimethylaminomethyl-esterified, pivaloyloxymethyl-esterified, 1-{(ethoxycarbonyl)oxy}ethyl-esterified, phthalidyl-esterified, (5-methyl-2-oxo-1,3-dioxolen-4-yl)methyl-esterified, 1-{[(cyclohexyloxy)carbonyl]oxy}ethyl-esterified or methylamidated). These compounds can be produced by known methods. The prodrug of the compound represented by general formula (I-A) may be either one of a hydrate and a non-hydrate. Alternatively, the prodrug of the compound represented by general formula (I-A) may be a compound which can change into a compound represented by general formula (I-A) under physiological conditions as mentioned in "Development of Pharmaceuticals", vol. 7, "Design of Molecules", pages: 163-198, 1990, Hirokawa-Shoten Ltd.

Furthermore, each of atoms constituting the compound represented by general formula (I-A) may be substituted by an isotope thereof (e.g., $^{2}H$, $^{3}H$, $^{11}C$, $^{13}C$, $^{14}C$, $^{15}N$, $^{16}N$, $^{17}O$, $^{18}O$, $^{18}F$, $^{35}S$, $^{36}Cl$, $^{77}Br$, $^{125}I$) or the like.

[Method for Producing the Compound of the Present Invention]

The compound of the present invention can be produced by an appropriately modified method of a known method, such as the method described in Comprehensive Organic Transformations: A Guide to Functional Group Preparations, 3rd Edition (Richard C. Larock, John Wiley & Sons Inc, 2018) and the methods mentioned in the section "EXAMPLES" or by a combination of these methods. A starting material may be used in the form of a salt. The order of the reactions to be carried out may be changed appropriately depending on the types of protecting groups introduced and the conditions for the reactions.

The compound represented by general formula (I-A) can be produced through reaction scheme 1.

<Reaction Scheme 1>

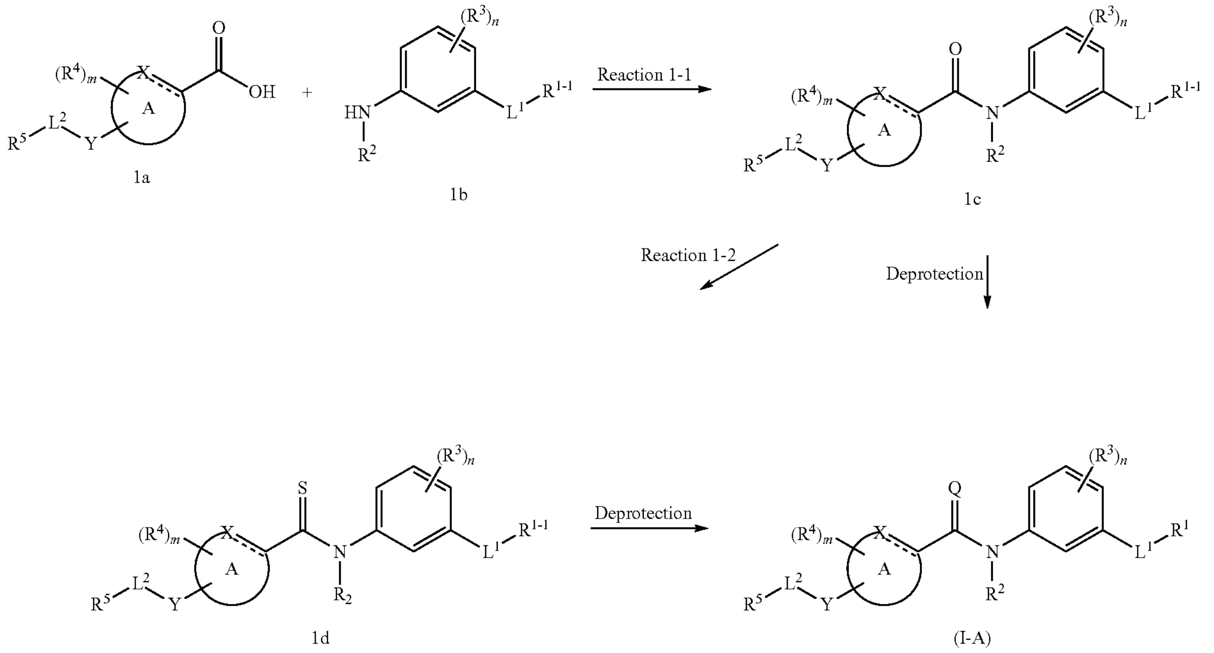

(In reaction scheme 1, $R^{1-1}$ represents $R^1$ which may be protected; and other symbols have the same meanings as mentioned above.)

In reaction scheme 1, reaction 1-1 is an amidation reaction. The amidation reaction is known, and includes, for example, the following methods:

(1) a method using an acid halide;

(2) a method using a mixed acid anhydride; and (3) a method using a condensing agent.

These methods will be described concretely as follows.

(1) The method using an acid halide is carried out by, for example, reacting a carboxylic acid with an acid halogenating agent (e.g., oxalyl chloride, thionyl chloride) in an organic solvent (e.g., chloroform, dichloromethane, diethyl ether, tetrahydrofuran) or without a solvent at −20° C. to a reflux temperature to produce an acid halide, and then reacting the acid halide with an amine in an organic solvent (e.g., chloroform, dichloromethane, diethyl ether, tetrahydrofuran) in the presence of a base (e.g., pyridine, triethylamine, di methyl aniline, dimethylaminopyridine, diisopropyl ethyl amine) at a temperature of 0 to 40° C. The method may also be carried out by reacting the acid halide with an amine in an organic solvent (e.g., dioxane, tetrahydrofuran) using an aqueous alkaline solution (e.g., an aqueous sodium bicarbonate solution or a sodium hydroxide solution) at 0 to 40° C.

(2) The method using a mixed acid anhydride can be carried out by, for example, reacting a carboxylic acid with an acid halide (e.g., pivaloyl chloride, tosyl chloride, mesyl chloride) or an acid derivative (e.g., ethyl chloroformate, isobutyl chloroformate) in an organic solvent (e.g., chloroform, dichloromethane, diethyl ether, tetrahydrofuran) or without a solvent in the presence of a base (e.g., pyridine, triethylamine, dimethylaniline, dimethylaminopyridine, diisopropylethylamine) at 0 to 40° C. to produce a mixed acid anhydride, and then reacting the mixed acid anhydride with an amine in an organic solvent (e.g., chloroform, dichloromethane, diethyl ether, tetrahydrofuran) at 0 to 40° C.

(3) The method using a condensing agent can be carried out by, for example, reacting a carboxylic acid with an amine in an organic solvent (e.g., chloroform, dichloromethane, dimethylformamide, diethyl ether, tetrahydrofuran) or without a solvent in the presence or absence of a base (e.g., pyridine, triethylamine, dimethylaniline, dimethylaminopyridine) using a condensing agent (e.g., 1,3-dicyclohexylcarbodiimide (DCC), 1-ethyl-3-[3-(dimethylamino)propyl] carbodiimide(EDC), 1,1'-carbonyldiimidazole (CDI), 2-chloro-1-methylpyridinium iodide, 1-propanephosphonic acid cyclic anhydride, PPA)) and using or without using 1-hydroxybenztriazole (HOBt) at 0 to 40° C.

It is desirable that each of these reactions (1), (2) and (3) is carried out in an inert gas (e.g., argon, nitrogen) atmosphere under waterless conditions.

In reaction scheme 1, reaction 1-2 is a thiolation reaction. The thiolation reaction is known, and can be produced by reacting a compound represented by general formula 1c in an organic solvent (e.g., tetrahydrofuran, toluene, benzene, acetonitrile, dichloromethane, pyridine) in the presence or absence of a base (e.g., sodium bicarbonate) and a thiolation reagent (e.g., a Lawesson's reagent (e.g., (2,4-bis(4-methoxyphenyl)-1,3,2,4-dithiadiphosphetane-2,4-disulfide), tetraphosphorus decasulfide, diphosphorus pentasulfide, hydrogen sulfide, sulfur) and in the presence or absence of a phosphine reagent (e.g., trichlorophosphate) at room temperature to a reflux temperature.

In reaction scheme 1, a compound represented by general formula 1c or 1d is optionally subjected to a deprotection reaction to produce a compound represented by general formula (I-A).

Examples of the protecting group for a carboxyl group include a methyl group, an ethyl group, a tert-butyl group, a trichloroethyl group, a benzyl (Bn) group, a phenacyl group, a p-methoxybenzyl group, a trityl group and a 2-chlorotrityl group.

Examples of the protecting group for an amino group or a tetrazolyl group include a benzyloxycarbonyl group, a tert-butoxycarbonyl group, an allyloxycarbonyl (Alloc) group, a 1-methyl-1-(4-biphenyl)ethoxycarbonyl (Bpoc) group, a trifluoroacetyl group, a 9-fluorenylmethyloxycarbonyl group, a benzyl (Bn) group, a p-methoxybenzyl group, a benzyloxymethyl (BOM) group, and a 2-(trimethylsilyl)ethoxymethyl (SEM) group.

Examples of the protecting group for a hydroxyl group or a hydroxamic acid include a methyl group, a trityl group, a methoxymethyl (MOM) group, a 1-ethoxyethyl (EE) group, a methoxyethoxymethyl (MEM) group, a 2-tetrahydropyranyl (THP) group, a trimethylsilyl (TMS) group, a triethylsilyl (TES) group, a tert-butyldimethylsilyl (TBDMS) group, a tert-butyldiphenylsilyl (TBDPS) group, an acetyl (Ac) group, a pivaloyl group, a benzoyl group, a benzyl (Bn) group, a p-methoxybenzyl group, an allyloxycarbonyl (Alloc) group, and a 2,2,2-trichloroethoxycarbonyl (Troc) group.

The deprotection reaction is known, and can be carried out by the following methods. For example, the following methods can be mentioned:

(1) a deprotection reaction by alkaline hydrolysis;
(2) a deprotection reaction under acidic conditions;
(3) a deprotection reaction by hydrogenolysis;
(4) a reaction of the deprotection of a silyl group;
(5) a deprotection reaction using a metal; and
(6) a deprotection reaction using a metal complex.

These methods will be described concretely as follows.

(1) The deprotection reaction by alkaline hydrolysis can be carried out, for example, in an organic solvent (e.g., methanol, tetrahydrofuran, dioxane) using a hydroxide of an alkali metal (e.g., sodium hydroxide, potassium hydroxide, lithium hydroxide), a hydroxide of an alkaline earth metal (e.g., barium hydroxide, calcium hydroxide), a carbonate (e.g., sodium carbonate, potassium carbonate) or an aqueous solution thereof or a mixture thereof at 0 to 40° C.

(2) The deprotection reaction under acidic conditions can be carried out, for example, in an organic solvent (e.g., dichloromethane, chloroform, dioxane, ethyl acetate, methanol, isopropyl alcohol, tetrahydrofuran, anisole) in an organic acid (e.g., acetic acid, trifluoroacetic acid, methanesulfonic acid, p-tosic acid) or an inorganic acid (e.g., hydrochloric acid, sulfuric acid) or a mixture thereof (e.g., hydrogen bromide/acetic acid) in the presence or absence of 2,2,2-trifluoroethanol at 0 to 100° C.

(3) The deprotection reaction by hydrogenolysis can be carried out, for example, in a solvent (e.g., an ether-type solvent (e.g., tetrahydrofuran, dioxane, dimethoxyethane, diethyl ether), an alcohol-type solvent (e.g., methanol, ethanol), a benzene-type solvent (e.g., benzene, toluene), a ketone-type solvent (e.g., acetone, methyl ethyl ketone), a nitrile-type solvent (e.g., acetonitrile), an amide-type solvent (e.g., N,N-dimethylformamide), water, ethyl acetate, acetic acid or a mixed solvent composed of two or more of these solvents) in the presence of a catalyst (e.g., palladium-carbon, palladium black, palladium hydroxide-carbon, platinum oxide, raney nickel) under a hydrogen atmosphere under ambient pressure or under pressure or in the presence of ammonium formate at 0 to 200° C.

(4) The reaction of deprotection of a silyl group can be carried out, for example, in an organic solvent miscible in water (e.g., tetrahydrofuran, acetonitrile) using tetrabutylammonium fluoride at 0 to 40° C. Alternatively, the deprotection reaction can also be carried out, for example, in an organic acid (e.g., acetic acid, trifluoroacetic acid, methanesulfonic acid, p-tosic acid) or an inorganic acid (e.g., hydrochloric acid, sulfuric acid) or a mixture thereof (e.g., hydrogen bromide/acetic acid) at −10 to 100° C.

(5) The deprotection reaction using a metal can be carried out, for example, in an acidic solvent (e.g., a mixed solution of acetic acid, a buffer solution having a pH value of 4.2 to 7.2 or a solution thereof with an organic solvent such as THF) in the presence of a zinc powder at 0 to 40° C. optionally while applying ultrasonic waves.

(6) The deprotection reaction using a metal complex can be carried out, for example, in an organic solvent (e.g., dichloromethane, N,N-dimethylformamide, tetrahydrofuran, ethyl acetate, acetonitrile, dioxane, ethanol), water or a mixed solvent thereof in the presence of a trapping reagent (e.g., tributyltin hydride, triethylsilane, dimedone, morpholine, diethylamine, pyrrolidine), an organic acid (e.g., acetic acid, formic acid, 2-ethyl hexanoic acid) and/or an organic acid salt (e.g., sodium 2-ethylhexanoate, potassium 2-ethylhexanoate) in the presence or absence of a phosphine-type reagent (e.g., triphenylphosphine) using a metal complex (e.g., tetrakis(triphenylphosphine)palladium (0), dichlorobis (triphenylphosphine)palladium (II), palladium acetate (II), chlorotris(triphenylphosphine)rhodium (I)) at 0 to 40° C.

In addition to the above-mentioned methods, the deprotection reaction can also be carried out by, for example, the method described in T. W. Greene, Protective Groups in Organic Synthesis, Wiley, New York, 5th Edition, 2014.

A typical example of the carboxylic acid represented by general formula 1a can be produced through reaction scheme 2.

<Reaction Scheme 2>

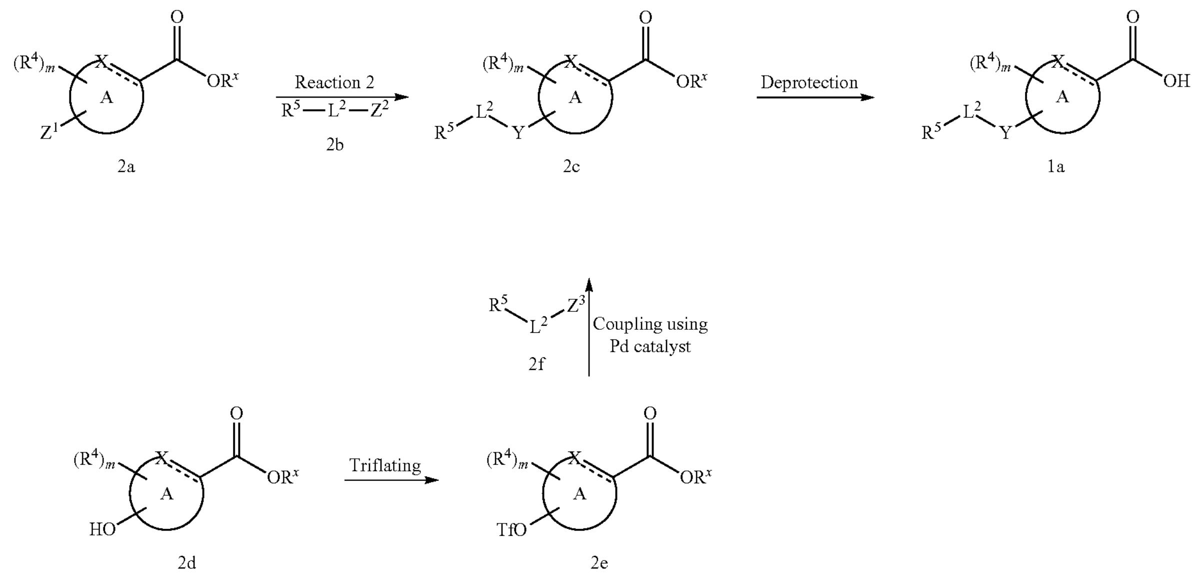

(In reaction scheme 2, $R^x$ represents a protecting group for a carboxylic acid; $Z^1$ represents a hydroxyl group or a thiol group; $Z^2$ represents a halogen atom or a hydroxyl group; $Z^3$ represents a $H_2C{=}CH$— group, a hydroxyl group, an amino group, a boronic acid group, a boronic acid ester group, a trialkyltin group, a trialkylsilane group or a halogenated zinc group; and other symbols have the same meanings as mentioned above.) In reaction scheme 2, reaction 2 is known. When $Z^2$ is a halogen atom, a compound represented by general formula 2c can be produced by a halogen substitution reaction.

The halogen substitution reaction is known, and can be carried out by, for example, reacting in an organic solvent (e.g., dimethylformamide, dimethylsulfoxide, chloroform, dichloromethane, diethyl ether, tetrahydrofuran, methyl t-butyl ether) in the presence of an alkali metal hydroxide (e.g., sodium hydroxide, potassium hydroxide, lithium hydroxide), an alkaline earth metal hydroxide (e.g., barium hydroxide, calcium hydroxide) or a carbonate (e.g., sodium carbonate, potassium carbonate) or an aqueous solution thereof or a mixture thereof at 0 to 100° C.

In reaction scheme 2, in the case where $Z^1$ is a hydroxyl group or a thiol group and $Z^2$ is a hydroxyl group, the compound represented by general formula 2c can be produced by a Mitsunobu reaction.

The Mitsunobu reaction is known, and can be achieved by, for example, reacting with a corresponding alcohol compound in an organic solvent (e.g., dichloromethane, diethyl ether, tetrahydrofuran, acetonitrile, benzene, toluene) in the presence of an azo compound (e.g., diethyl azodicarboxylate (DEAD), diisopropyl azodicarboxylate, 1,1'-(azodicarbonyl)dipiperidine, 1,1'-azobis (N,N-dimethylformamide)) and a phosphine compound (e.g., triphenylphosphine, tributylphosphine, trimethylphosphine, polymer-supported triphenylphosphine) at 0 to 60° C.

As another method for producing the compound represented by general formula 2c, the compound represented by general formula 2c can be produced by triflating a compound represented by general formula 2d and then subjecting the resultant produce to a coupling reaction with a compound represented by general formula 2f using a palladium catalyst.

The triflating is known, and can be achieved typically by reacting 1,1,1-trifluoro-N-(trifluoromethylsulfonyl)methanesulfonamide or trifluoromethanesulfonic anhydride in an organic solvent (e.g., dichloromethane, diethyl ether, tetrahydrofuran, acetonitrile, benzene, toluene) in the presence of a base (e.g., pyridine, triethylamine, dimethylaniline, dimethylaminopyridine, diisopropylethylamine).

Examples of the coupling reaction using a palladium catalyst include Suzuki coupling, Stille coupling, Buchwald coupling, Negishi coupling, Heck coupling and Hiyama coupling.

These reactions are known, and can be achieved by, for example, reacting in an organic solvent (e.g., benzene, toluene, dimethylformamide, dioxane, tetrahydrofuran, methanol, acetonitrile, dimethoxyethane, acetone) in the presence of a base (e.g., sodium ethylate, sodium hydroxide, potassium hydroxide, triethylamine, sodium carbonate, sodium bicarbonate, potassium carbonate, cesium carbonate, thallium carbonate, tripotassium phosphate, cesium fluoride, barium hydroxide, tetrabutylammonium fluoride)) or an aqueous solution thereof or a mixture thereof and a catalyst (e.g., tetrakis(triphenylphosphine)palladium($Pd(PPh_3)_4$), bis(triphenylphosphine)palladium dichloride ($PdCl_2(PPh_3)_2$), palladium acetate($Pd(OAc)_2$), palladium black, 1,1'-bis(diphenylphosphinoferrocene)dichloropalladium($PdCl_2(dppf)_2$), diallylpalladium chloride($PdCl_2(allyl)_2$), phenylbis(triphenylphosphine)palladium iodide($PhPdI(PPh_3)_2$)) at room temperature to 120° C.

The carboxylic acid represented by general formula 1a can be produced by the above-mentioned carboxyl group deprotection reaction using the compound represented by general formula 2c.

A typical example of the amine compound represented by general formula 1b can be produced through reaction scheme 3.

<Reaction Scheme 3>

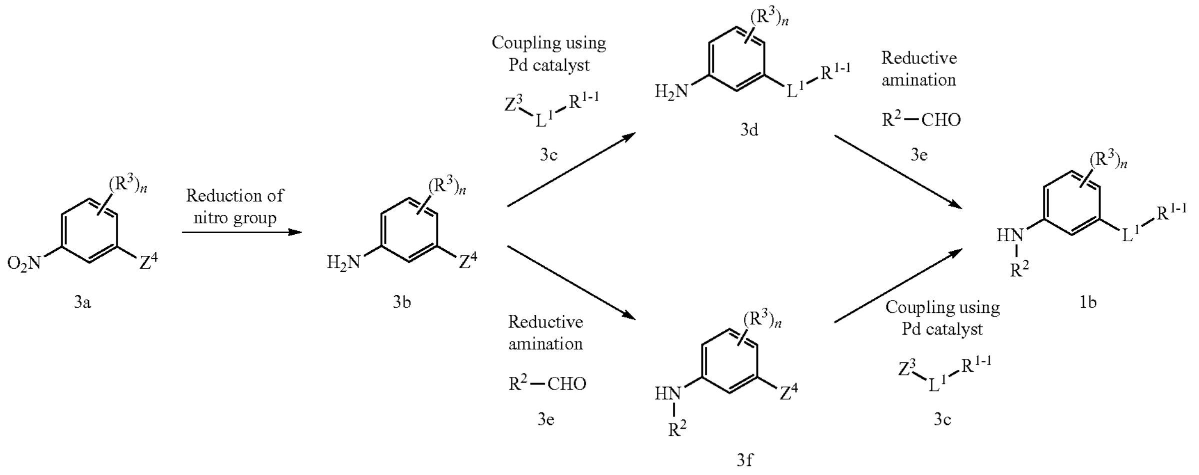

(wherein $Z^4$ represents a halogen atom; and other symbols have the same meanings as mentioned above.)

In reaction scheme 3, the reaction for reducing a nitro group is known, and can be achieved by, for example, in a solvent miscible with water (e.g., ethanol, methanol, tetrahydrofuran) in the presence or absence of an acid (e.g., hydrochloric acid, hydrobromic acid, ammonium chloride, acetic acid, ammonium formate) using a metal reagent (e.g., zinc, iron, tin, tin chloride, iron chloride, samarium, indium, sodium borohydride-nickel chloride) at a temperature of 0 to 150° C.

In reaction scheme 3, a compound represented by general formula 3d or general formula 1b can be produced by subjecting the coupling reaction using a palladium catalyst to the same reaction conditions as mentioned above.

In reaction scheme 3, the reductive amination reaction is known, and can be achieved by, for example, in an organic solvent (e.g., dichloroethane, dichloromethane, dimethylformamide, acetic acid, and a mixture thereof) in the presence of a reducing agent (e.g., sodium triacetoxyborohydride, sodium cyanoborohydride, sodium borohydride) at a temperature of 0 to 40° C. to produce a compound represented by general formula 3f or general formula 1b.

Among the compounds represented by general formula (I-A), a compound in which Q is an oxygen atom and $L^1$ is a C3-6 saturated carbocyclic ring, i.e., a compound represented by general formula (I-1):

(I-1)

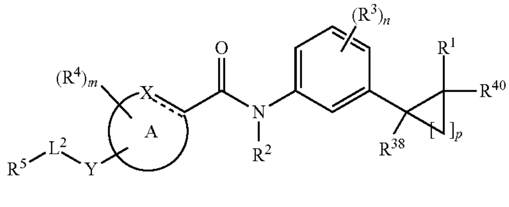

(wherein all symbols have the same meanings as mentioned above) can be produced through reaction scheme 4.

<Reaction Scheme 4>

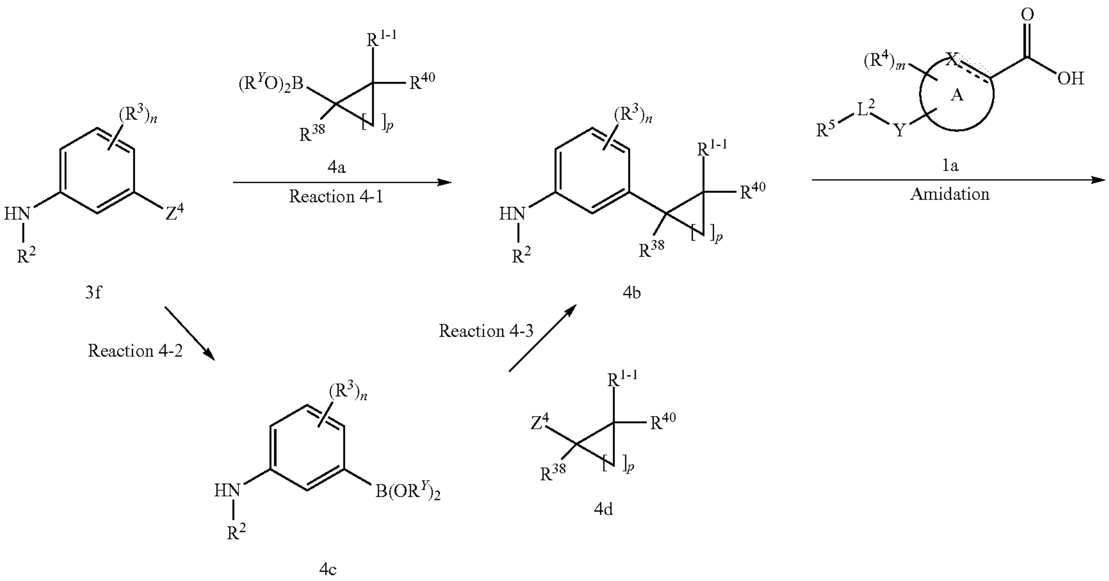

-continued

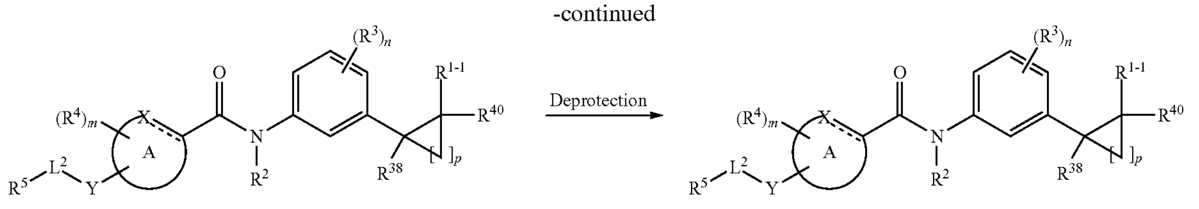

4e (I-1)

(wherein —$B(OR^Y)^2$ represents boronic acid or a boronic acid ester (e.g., dimethyl boronate ester, dioxaborolane, 4,4,5,5-tetramethyl-1,3,2-dioxaborolane, dioxaborinane, 5,5-dimethyl-1,3,2-dioxaborinane); and other symbols have the same meanings as mentioned above.)

In reaction scheme 4, the reaction 4-1 is known, and a compound represented by general formula 4b can be produced by subjecting a compound represented by general formula 3f and a compound represented by general formula 4a to the conditions for the Suzuki coupling reaction. As an alternative method for producing the compound represented by general formula 4b, the amine compound represented by general formula 4b can be produced by converting a compound represented by general formula 3f to a boronic acid ester represented by general formula 4c by the reaction 4-2 and then carrying out the reaction 4-3 using a compound represented by general formula 4d.

The reaction 4-2 is known, and can be produced by, for example, carrying out Suzuki Coupling reaction using bis(pinacolato)diboron.

Reaction 4-3 is known, and a compound represented by general formula 4b can be produced by subjecting a compound represented by general formula 4c and a compound represented by general formula 4d to Suzuki coupling reaction.

The compound represented by general formula 4b and the carboxylic acid compound represented by general formula 1a are amidated by the method described above to produce a compound represented by general formula 4e.

The compound represented by general formula 4e is optionally deprotected to prepare a compound represented by general formula (I-1).

The compound represented by general formula (I-1) can also be produced by amidating a compound represented by general formula 1a and a compound represented by general formula 3f and then subjecting the resultant products to reaction 4-1 with a compound represented by general formula 4a and then optionally deprotecting the resultant product.

The compound represented by general formula (I-1) can also be produced by amidating a compound represented by general formula 1a and a compound represented by general formula 3f, then carrying out reaction 4-2, then subjecting the resultant product and a compound represented by general formula 4d to reaction 4-3, and then optionally deprotecting the resultant product.

Among the compounds represented by general formula (I-A), a compound in which Q is an oxygen atom, the ring A is a 5-membered nitrogen-containing aromatic heterocyclic ring, X is $NR^7$, Y is a bond and $L^1$ is a C3-6 saturated carbocyclic ring, i.e., a compound represented by general formula (I-2):

(I-2)

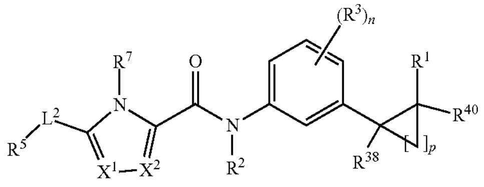

(wherein $X^1$ and $X^2$ each independently represent CH, $CR^4$ or a nitrogen atom; and other symbols have the same meanings as mentioned above), can be produced by reaction scheme 5 shown below.

<Reaction Scheme 5>

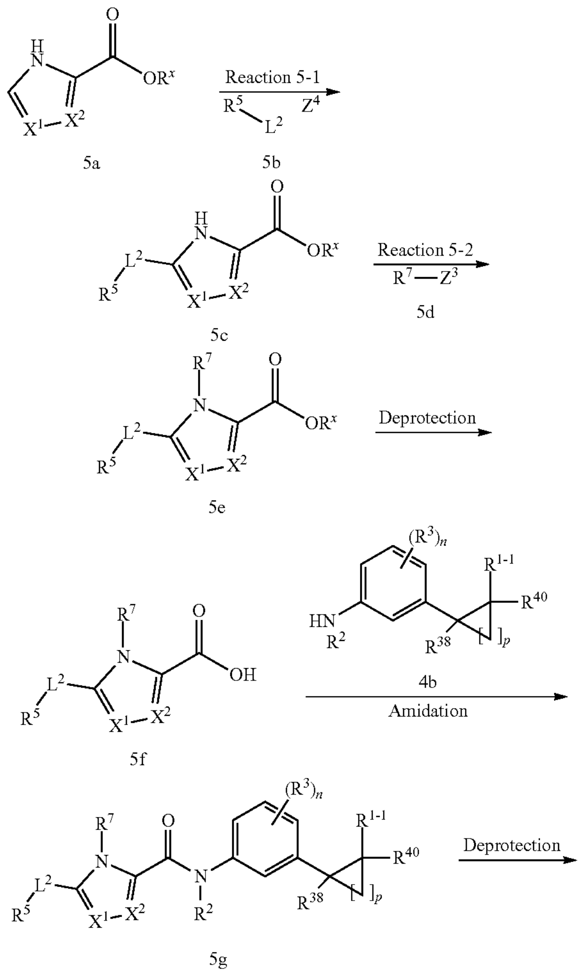

5a 5b 5c 5d 5e 5f 4b 5g

-continued

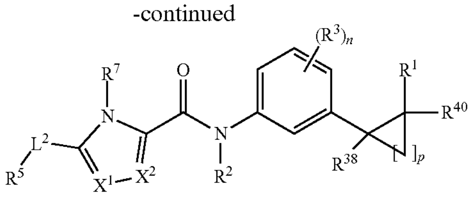

(I-2)

(wherein all symbols have the same meanings as mentioned above.)

Reaction 5-1 is known, and can be achieved by a C—H activation reaction using norbornene. For example, as described in Angewandte Chemie-International Edition, 2013, vol. 52, #23, p. 6080-6083, a compound represented by general formula 5c can be produced by carrying out the reaction using a compound represented by general formula 5a and a compound represented by general formula 5b in an organic solvent (e.g., N,N-dimethylacetamide, acetonitrile) in the presence of a base (e.g., potassium carbonate, potassium bicarbonate) by adding norbornene and a palladium catalyst (e.g., bis(acetonitrile)dichloropalladium (II)) at a temperature of 70° C. to 90° C.

In reaction scheme 5, reaction 5-2 is known, and a compound represented by general formula 5e can be produced by subjecting to the halogen substitution reaction or the Mitsunobu reaction.

The carboxylic acid deprotection, the amidation and the deprotection reaction for the compound represented by general formula 5e can be performed by the same procedures as mentioned above.

Among the compounds represented by general formula (I-A), a compound in which Q is an oxygen atom, the ring A is a 5-membered nitrogen-containing aromatic heterocyclic ring, X is $CR^6$, Y is a bond and $L^1$ is a C3-6 saturated carbocyclic ring, i.e., a compound represented by general formula (I-3):

(I-3)

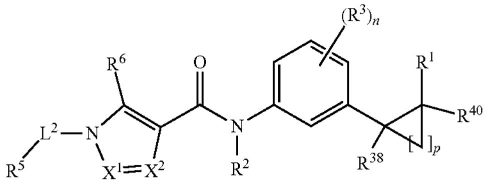

(wherein all symbols have the same meanings as mentioned above), can be produced by replacing a compound represented by general formula 5f in reaction scheme 5 by a compound represented by general formula 6d:

6d

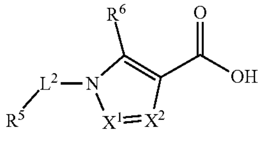

(wherein all symbols have the same meanings as mentioned above). A compound represented by general formula 6d can be produced through reaction scheme 6.

<Reaction Scheme 6>

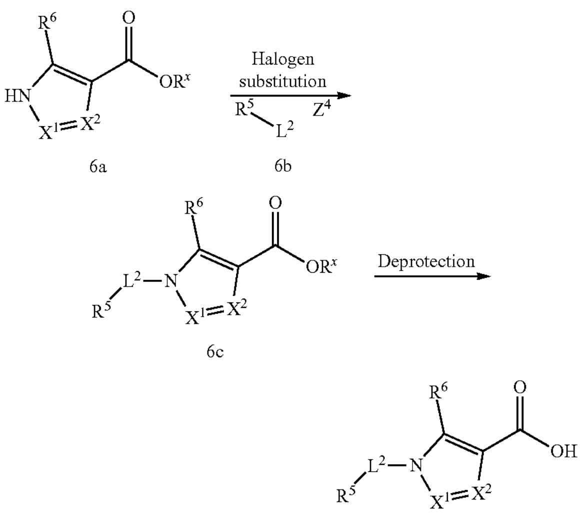

6a 6b 6c 6d (wherein all symbols have the same meanings as mentioned above.)

In reaction scheme 6, the halogen substitution reaction and the carboxylic acid deprotection reaction can be carried out under the same conditions as mentioned above.

Among the compounds represented by general formula (I-A), a compound in which Q is an oxygen atom, the ring A is a benzene ring, Y is an oxygen atom and $L^1$ is a C3-6 saturated carbocyclic ring, i.e., a compound represented by general formula (I-4):

(I-4)

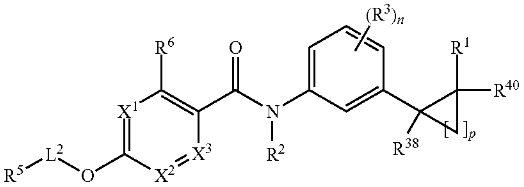

(wherein $X^1$, $X^2$ and $X^3$ each independently represent CH or $CR^4$; and other symbols have the same meanings as mentioned above), can be produced by reaction scheme 7 shown below.

<Reaction Scheme 7>

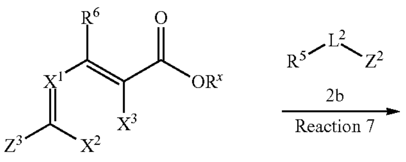

7a

-continued

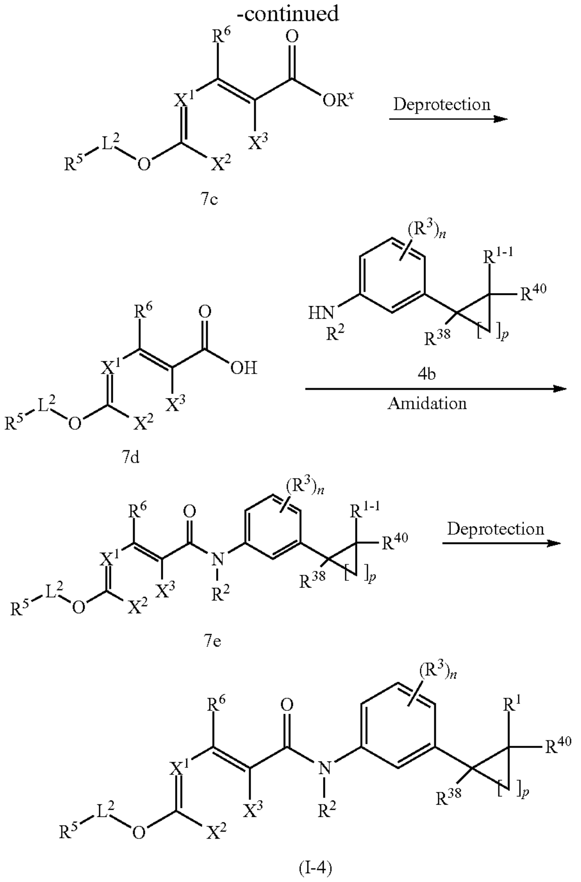

7c

4b

7d

7e (I-4)

(wherein all symbols have the same meanings as mentioned above.)

In reaction scheme 7, reaction 7 is known. When $Z^3$ is a hydroxyl group, a compound represented by general formula 7c can be produced by carrying out the above-mentioned Mitsunobu reaction.

In the case where $Z^2$ is a hydroxyl group and $Z^3$ is a halogen atom, a compound represented by general formula 7c can be produced by an Ullmann etherification reaction.

The Ullmann etherification reaction is known, and can be achieved by, for example, reacting in an organic solvent (e.g., benzene, toluene, dimethylformamide, dioxane, tetrahydrofuran, methanol, acetonitrile, dimethoxyethane, acetone) in the presence of a phosphine ligand (e.g., triphenylphosphine, 4,5-bis(diphenylphosphino)-9,9-dimethylxanthene(xantphos)), a base (e.g., sodium ethylate, sodium hydroxide, potassium hydroxide, triethylamine, sodium carbonate, sodium bicarbonate, potassium carbonate, cesium carbonate, thallium carbonate, tripotassium phosphate, cesium fluoride, barium hydroxide, tetrabutylammonium fluoride) or an aqueous solution thereof or a mixture thereof and a catalyst (e.g., copper iodide) at room temperature to 130° C.

In reaction scheme 7, the carboxylic acid deprotection, the amidation and the deprotection reaction of a compound represented by general formula 7c can be carried out by the same methods as mentioned above.

With respect to compounds other than the above-mentioned compositions among the compounds of the present invention, those compounds represented by general formula 2a, general formula 2b, general formula 2d, general formula 2f, general formula 3a, general formula 3c, general formula 3e, general formula 4a, general formula 4d, general formula 5a, general formula 5b, general formula 5d, general formula 6a, general formula 6b and general formula 7a, which are used as starting materials in the individual reactions mentioned in the specification are known, or can be produced easily by employing a known method, such as a method described in "Comprehensive Organic Transformations: A Guide to Functional Group Preparations, 3rd Edition (Richard C. Larock, John Wiley & Sons Inc, 2018) or the like, or a combination of methods each of which is a modification of a known method.

Each of compounds each having an amino group, a carboxy group or a hydroxyl group, which are used in the present invention, can be produced by optionally carrying out a proper reaction step using a compound protected with a protecting group that are commonly used for these groups, e.g., a protecting group described in "T. W. Greene, Protective Groups in Organic Synthesis, Wiley, New York, 5th Edition, 2014", and then carrying out a known deprotection reaction.

Among the compounds used in the present invention, compounds each having an optical activity can be produced by using a starting material or a reagent each having an optical activity, or by optically resolving an intermediate for the production of a racemic form and then converting the resultant product to the compound of the present invention, or by optically resolving a racemic form of a compound of the present invention.

The optical resolution is known, and examples thereof include a method in which a salt, a complex or the like is formed with other optically active compound, recrystallizing the salt, complex or the like and then isolating a desired compound, and a method in which a desired compound is separated directly using a chiral column or the like.

In each of the reactions mentioned in the specification, a reaction including heating can be carried out using a water bath, an oil bath, a sand bath or microwaves, as apparent to persons skilled in the art.

In each of the reactions mentioned in the specification, a solid-phase-supported reagent that is supported on a high-molecular-weight polymer (e.g., polystyrene, polyacrylamide, polypropylene, polyethylene glycol) may also be used appropriately.

In each of the reactions mentioned in the specification, a reaction product can be purified by a conventional purification means, such as distillation under ambient pressure or under reduced pressure, high-performance liquid chromatography using silica gel or magnesium silicate, thin-layer chromatography, an ion exchange resin, a scavenger resin, column chromatography, washing and recrystallization. The purification may be carried out for every reactions, or may be carried out after the completion of several reactions.

[Toxicity]

The toxicity of the compound of the present invention is low, and therefore can be used as a medicament safely.

[Application to Medicament]

An object of the present invention is to discover a compound that has a potent antagonistic activity against an $EP_2$ receptor and therefore is useful as a prophylactic and/or therapeutic agent for a disease associated with the activation of an $EP_2$ receptor.

The compound of the present invention can exert a potent antagonistic activity against an $EP_2$ receptor, and is therefore useful as a prophylactic and/or therapeutic agent for a disease associated with the activation of an $EP_2$ receptor, such as endometriosis, uterine fibroids, hypermenorrhea, adenomyosis, dysmenorrhea, chronic pelvic pain syndrome, cancer, inflammatory pain, neuropathic pain, headache, postoperative pain, interstitial cystitis, leiomyoma, irritable colon syndrome, Alzheimer's disease, Parkinson's disease, amyotrophic lateral sclerosis, multiple sclerosis, rheumatism, osteoarthritis, gout, an allergic disease, hypertension, brain dysfunction, ischemia, stroke, a kidney disease, transplant rejection, atherosclerosis, an ischemic heart disease, acne vulgaris, asthma, prostatitis, glomerulonephritis, sarcoidosis, vasculitis and an autoimmune disease.

More specifically, examples of the cancer include breast cancer, ovarian cancer, colorectal cancer (e.g., colon cancer), lung cancer (e.g., non-small-cell lung cancer), prostate cancer, head and neck cancer (e.g., oral squamous cell carcinoma, head and neck squamous cell carcinoma, pharyngeal cancer, laryngeal cancer, tongue cancer, thyroid cancer, acoustic schwannoma), lymphoma (e.g., B cell lymphoma, T cell lymphoma), uveal melanoma, thymoma, mesothelioma, esophageal cancer, stomach cancer, duodenal cancer, hepatocellular carcinoma, bile duct cancer, gallbladder cancer, pancreatic cancer, renal cell carcinoma, renal pelvis/ureteral cancer, bladder cancer, penile cancer, testicular cancer, uterine cancer, vaginal cancer, vulvar cancer, skin cancer (e.g., malignant melanoma), malignant bone tumor, soft tissue sarcoma, chondrosarcoma, leukemia (e.g., acute myelogenous leukemia, acute lymphocytic leukemia, chronic myelogenous leukemia, chronic lymphocytic leukemia), myelodysplastic syndrome, brain tumor and multiple myeloma. Examples of the autoimmune disease include amyotrophic lateral sclerosis (ALS), multiple sclerosis, Sjogren's syndrome, systemic lupus erythematosus and AIDS. Examples of the allergic disease include allergic conjunctivitis, allergic rhinitis, contact dermatitis and psoriasis. Examples of the headache include migraine, tension headache or mixed headache thereof, and cluster headache.

In the use of the compound of the present invention for the purpose of preventing and/or treating the above-mentioned diseases, the substance that acts as an active ingredient, is generally formulated into a preparation together with various additives or a pharmaceutically acceptable carrier such as a solvent and is administered in an oral or parenteral dosage form systemically or topically. The term "pharmaceutically acceptable carrier" as used herein refers to a substance which is commonly used in the formulation of a drug and is different from an active ingredient. The pharmaceutically acceptable carrier is preferably a substance which does not exert any pharmacological activity in the amount contained in the preparation to be administered, is nontoxic, and cannot interfere the therapeutic effect of the active ingredient. The pharmaceutically acceptable carrier can also be used for the purpose of increasing the usefulness of the active ingredient and the preparation, facilitating the production of the preparation, stabilizing the quality, improving the usefulness or the like. More specifically, a substance as described in, for example, "Japanese Pharmaceutical Excipients Directory" (edited by Japan Pharmaceutical Excipients Council), published in 2000 by Yakuji Nippo Limited may be selected appropriately depending on the intended use.

The compound of the present invention can be administered to a mammal (preferably human, more preferably a human patient) in a pharmaceutically active amount.

The amount of the compound of the present invention to be administered depends on ages, body weights, clinical condition, desired therapeutic effects, routes of administration, period of therapy and the like, and may therefore vary inevitably. In general, the compound of the present invention is administered orally in a single dose of 0.1 mg to 1000 mg per patient, or is administered parenterally or administered sustainably intravenously at a single dose of 0.01 mg to 100 mg per patient.

As mentioned above, the dose amount varies depending on various factors. Therefore, the administration in a smaller dose amount than the above-mentioned dose amount may be sufficient in some cases, or the administration in a larger dose amount than the above-mentioned dose amount may be needed in some cases.

Examples of the dosage forms include a preparation for oral administration (e.g., tablets, capsules, granules, a powder, an oral liquid preparation, a syrup, an oral jelly), a preparation for administration to oral cavity (e.g., tablets for oral cavity administration, a spray for oral cavity administration, a semi-solid preparation for oral cavity administration, a gargle), an injection preparation (e.g., an injection), a preparation for dialysis (e.g., a medicine for dialysis), a preparation for inhalation (e.g., an inhalant), an ophthalmic preparation (e.g., eye drops, an ophthalmic ointment), an otologic preparation (e.g., ear drops), a rhinologic preparation (e.g., nose drops), a rectal preparation (e.g., a suppository, a rectal semi-solid preparation, an enema), a vaginal preparation (e.g., vaginal tablets, a vaginal suppository), and a preparation for skin (e.g., a solid preparation for external application, a liquid for external application, a spray, an ointment, a cream, a gel, an adhesive skin patch).

[Preparation for Oral Administration]

Examples of the preparation for oral administration include tablets, capsules, granules, a powder, an oral liquid, a syrup and an oral jelly. The preparation for oral administration includes: a rapidly disintegrating preparation which is not particularly controlled with respect to the releasability of the active ingredient from the preparation; and a controlled release preparation which is controlled with respect to the releasability of the active ingredient from the preparation depending on the intended use by a specific preparation designing and a preparation method, such as an enteric preparation and a sustained-release preparation. The term "enteric preparation" refers to a preparation which is so designed as not to release an active ingredient in the stomach but release the active ingredient mainly in the small intestine for the purpose of, for example, preventing the degradation of the active ingredient in the stomach or reducing the irritable action of the active ingredient against the stomach, and is generally prepared by providing a coating film using an acid-insoluble enteric base. The term "sustained-release preparation" refers to a preparation which is controlled with respect to the rate, time, and the site of release of an active ingredient from the preparation to which the preparation is to be released for the purpose of reducing the time of frequency of administration or reducing adverse side effects, and can be generally prepared using a proper sustained-release agent. Among the preparations for oral administration, capsules, granules, tablets or the like may be provided with a coating film made from a sugar, a sugar alcohol, a polymeric compound or the like for the purpose of, for example, making the ingestion of the preparation easy or preventing the degradation of the active ingredient.

(1) Tablets

A table is a solid preparation which is intended to be administered orally and has a certain shape. Examples of the tablet include: a so-called "tablet" such as an uncoated tablet, a film-coated tablet, a sugar-coated tablet, a multi-layered tablet, and a dry-coated tablet; and an orally rapidly disintegrating tablet, a chewable tablet, an effervescent tablet, a dispersible tablet, and a soluble tablet. For the production of noncoated tablets, generally any one of the following techniques (a), (b) and (c) is employed:

(a) additives such as an excipient, a binder and a disintegrating agent are added to an active ingredient, the resultant mixture is agitated homogeneously, the agitated mixture is granulated by a proper method using a solution containing water or a binder, a lubricant or the like is then added to the granules, and the granules are compression-molded;

(b) additives such as an excipient, a binder and a disintegrating agent are added to an active ingredient, the resultant homogeneous mixture is directly compression-molded; or an active ingredient, a lubricant and the like are added to granules that have been prepared in advance using additives, the resultant mixture is agitated homogeneously and the resultant product is compression-molded; and (c) additives such as an excipient and a binder are added to an active ingredient, the resultant mixture is agitated homogeneously, and is then moisturized with a solvent to produce a kneaded product, the kneaded product is poured into a specific mold, and the resultant product is dried by a proper method.

The film-coated tablet can be generally produced by providing a thin coating film using a proper coating agent such as a polymeric compound onto an uncoated tablet. The sugar-coated tablet can be generally produced by providing a coating film using a coating agent containing a sugar or a sugar alcohol onto an uncoated tablet. The multi-layered tablet can be produced by overlaying granular bodies having different compositions in layers by a proper method, and the resultant product is compression-molded. The dry-coated tablet can be produced by covering an inner core tablet with an outer layer having a different composition from that of the inner core tablet. The tablet may be made into an enteric tablet or a controlled-release tablet by employing a known proper technique. Each of the orally rapidly disintegrating tablet, the chewable tablet, the effervescent tablet, the dispersing tablet and the soluble tablet is a tablet having a specific function imparted thereto by selecting additive appropriately, and can be produced by the same tablet production technique as those mentioned above. In this regard, the term "orally rapidly disintegrating tablet" refers to a tablet which can be dissolved or disintegrated rapidly in the oral cavity upon ingestion; the term "chewable tablet" refers to a tablet which is chewed upon ingestion; the term "the effervescent tablet" refers to a tablet which can be dissolved or dispersed in water while giving bubbles; the term "dispersing tablet" refers to a tablet which is dispersed in water upon ingestion; and the term "soluble tablet" refers to a tablet which is dissolved in water upon ingestion. The effervescent tablet can be produced by using a proper acidic substance, a carbonate salt, a bicarbonate salt or the like as an additive.

(2) Capsules

The capsule is a preparation prepared by filling in a capsule or coating and shaping with a capsule base material, and includes a hard capsule, a soft capsule and the like. The hard capsule can be produced by filling a material, which has been prepared by adding additives such as an excipient to an active ingredient and then agitating the mixture homogeneously or a granular or shaped product of the material by a proper method, in a capsule without any modification or after being slightly shaped. The soft capsule can be produced by coating and shaping a material, which has been prepared by adding additives to an active ingredient, into a given shape using a proper capsule base such as gelatin that has been increased in plasticity by adding glycerin, D-sorbitol or the like. The capsule can be prepared in an enteric capsule or a sustained-release capsule by employing a known proper technique. A coloring agent or a preservative may be added to the capsule base.

(3) Granules

The granule is a preparation granulated into granules, and include a so-called "granule", an effervescent granule and the like. For the production of the granules, generally any one of the following techniques (a), (b) and (c) is employed:

(a) additives such as an excipient, a binder, a disintegrating agent and the like are added to a powdery active ingredient, the resultant mixture is agitated homogeneously, and the agitated mixture is granulated by a proper method;

(b) additives such as an excipient are added to an active ingredient that has been prepared into a granular form in advance, and the resultant mixture is agitated homogeneously; and (c) additives such as an excipient are added to an active ingredient that has been prepared into a granular form in advance, the resultant mixture is agitated homogeneously, and the agitated product is made into granules by a proper method.

The granules may be provided with a coating, or may be prepared as enteric granules or sustained-release granules by employing a known proper technique. The effervescent granules can be produced by using a proper acidic substance, a proper carbonate salt, a proper bicarbonate salt or the like as an additive. The term "effervescent granules" refer to granules which can be dissolved or dispersed in water while rapidly forming bubbles. The granules may be in the form of fine granules by controlling the sizes of granules.

(4) Powder

The powder is a powdery preparation, and can be generally produced by adding an excipient or other additives to an active ingredient and then agitating the resultant mixture homogeneously.

(5) Oral Liquid

The oral liquid is a liquid or flowable viscous gel-like preparation, and include a common so-called "oral liquid" as well as an elixir, a suspension, an emulsion and a lemonade. The oral liquid can be generally produced by adding additives and purified water to an active ingredient, then agitating the resultant mixture to dissolve, emulsify or suspend these components homogeneously, and then optionally filtrating the resultant solution. The elixir is a clear, liquid-like oral liquid containing ethanol and having a sweet taste and an aromatic flavor, and can be generally produced by adding and dissolving ethanol, purified water, a flavoring agent, white sugar and other sugar or a sweetening agent to and in a solid active ingredient or a leaching solution thereof, and then made the resultant solution clear by filtration or other method. The suspension is an oral liquid in which an active ingredient is suspended finely homogeneously, and can be generally produced by adding a suspending agent or other additive and purified water or an oil to a solid active ingredient, then suspending the resultant mixture by a proper method to make the solution wholly homogeneous. The emulsion is an oral liquid in which an active ingredient is emulsified finely homogeneously, and can be generally produced by adding an emulsifying agent and purified water to a liquid active ingredient, then emulsifying the resultant mixture by a proper method to make the solution wholly homogeneous. The lemonade is a clear liquid-like oral liquid having a sweet taste and a sour taste.

(6) Syrup

The syrup is a preparation having a viscous liquid form or a solid form and containing a sugar or a sweetening agent, and includes a preparation for syrups. The syrup can be generally produced by adding an active ingredient to a solution of white sugar or other sugar or a sweetening agent or a simple syrup, then dissolving, agitating, suspending or emulsifying these components, then optionally boiling the resultant solution, and then filtrating the solution while heating. The preparation for syrups refers to a granular or powdery preparation which can be prepared into a syrup when water is added thereto, and is sometimes called a "dry syrup". The preparation for syrups can be generally produced in accordance with a technique for producing the granules or the powder using a sugar or a sweetening agent as an additive.

(7) Oral Jelly

The oral jelly is a gel-like preparation that is shaped and does not have fluidability, and can be generally produced by adding an additive and a polymeric gel base to an active ingredient, then agitating these components, then gelatinizing the resultant mixture by a proper method, and then shaping the resultant product in a given shape.

[Preparation for Injection]

(1) Injection

The injection is a solution, a suspension or an emulsion which can be administered subcutaneously or intramuscularly or can be administered directly to a tissue or organ such as a blood vessel in vivo, or is a solid germ-free preparation which can be dissolved or suspended upon use. The injection includes a common so-called "injection" as well as a freeze-dried injection, a powdery injection, a prefilled syringe, a cartridge, an infusion fluid, an implantable injection, and a long-acting injection. For the production of the injection, generally any one of the following techniques (a) and (b) is employed:

(a) an active ingredient or a mixture of the active ingredient and an additive is dissolved, suspended or emulsified in water for injection or other water-based solvent, a non-water-based solvent or the like homogeneously, then the resultant solution was packed in a container for injections, and then the container is hermetically sealed and sterilized; and (b) an active ingredient or a mixture of the active ingredient and an additive is dissolved, suspended or emulsified in water for injection or other water-based solvent, a non-water-based solvent or the like homogeneously, then the resultant solution was filtrated aseptically or the solution is prepared aseptically and made homogeneous, then the resultant solution is packed in a container for injections, and then the container is hermetically sealed.

The freeze-dried injection can be generally produced by dissolving an active ingredient or a mixture of the active ingredient and additives including an excipient in water for injections, then filtrating the resultant solution aseptically, and then packing the filtrated solution in a container for injections and then freeze-drying the solution or freeze-drying the filtrated solution in a specialized container and then packing the freeze-dried product in a container directly. The powdery injection can be generally produced by packing a powder that has been treated by aseptic filtration and then crystallized or a mixture of the powder and an additive that has undergone a sterilization treatment in a container for injections. The prefilled syringe can be generally produced by packing an active ingredient in an injection syringe, or by preparing a solution, a suspension or an emulsion using the active ingredient and an additive and then packing the solution, the suspension or the emulsion in an injection syringe. The cartridge is an injection having such a form that a cartridge having a drug solution packed therein is installed in a specialized injection syringe upon use. The cartridge having a drug solution packed therein can be generally produced by packing an active ingredient in a cartridge or by preparing a solution, a suspension or an emulsion using the active ingredient and an additive and then packing the solution, the suspension or the emulsion in a cartridge. The infusion fluid is an injection which is intended to be administered intravenously and generally has a volume of 100 mL or more. The implantable injection is a solid or gel-like injection which is intended to be administered for the purpose of releasing an active ingredient for a long period and can be applied subcutaneously, intramuscularly or the like using a tool for implantation use or by means of operative treatment. The implantable injection can be generally produced by using a biodegradable polymeric compound and forming the biodegradable polymeric compound into pellets, microspheres or a gel-like form. The long-acting injection refers to an injection which can be applied into a muscle or the like for the purpose of releasing an active ingredient for a long period, can be generally produced by dissolving or suspending an active ingredient in a vegetable oil or the like or by preparing a suspension of microspheres using the biodegradable polymeric compound.

The compound of the present invention may be administered as a concomitant drug in combination with other drug for the purpose of:

(1) the complementation and/or enhancement of the prophylactic and/or therapeutic effect of the compound;

(2) the improvement of the pharmacokinetics/absorption of the compound, the reduction in the amount of the compound to be administered; and/or (3) the relief of adverse side effects of the compound.

With respect to a combined drug comprising the compound of the present invention and other drug, the combined drug may be administered in the form of a blended preparation in which both of the components are blended in a single preparation, or these drugs may be administered in separately prepared preparations. In the case where the drugs are administered in separately prepared preparations, the administration includes simultaneous administration and time difference administration. In the case of time difference administration, it is possible to administer the compound of the present invention first and administer other drug later, or administer other drug first and administer the compound of the present invention later. The method for the administration of the compound of the present invention and the method for the administration of other drug may be the same as or different from each other.

The disease on which the combined drug can exert the prophylactic and/or therapeutic effect thereof is not particularly limited, and any disease may be employed as long as the prophylactic and/or therapeutic effect of the compound of the present invention can be complemented or enhanced against the disease.

Examples of the other drug for complementing and/or enhancing the prophylactic and/or therapeutic effect of the compound of the present invention against cancer include an alkylating agent, an antimetabolic agent, an anticancer antibiotic, a plant-derived preparation, a hormonal agent, a platinum compound, a topoisomerase inhibitor, a kinase inhibitor, an anti-CD20 antibody, an anti-HER2 antibody, an anti-EGFR antibody, an anti-VEGF antibody, a proteasome inhibitor, an HDAC inhibitor and an immunomodulatory drug.

Examples of the alkylating agent include cyclophosphamide, ifosfamide, dacarbazine, temozolomide, nimustine hydrochloride, ranimustine, bendamustine, thiotepa, and carboquone.

Examples of the antimetabolic agent include methotrexate, pemetrexed, fluorouracil, tegafur, tegafur•uracil, tegafur•gimestat•potassium otastat, doxifluridine, capecitabine, cytarabine, gemcitabine hydrochloride, fludarabine, nelarabine, carmofur, and procarbazine hydrochloride.

Examples of the anticancer antibiotic include mitomycin C, doxorubicin hydrochloride, aclarubicin hydrochloride, pirarubicin hydrochloride, epirubicin, chromomycin A3, bleomycin, peplomycin sulfate, and therarubicin.

Examples of the plant-derived preparation include irinotecan hydrochloride, etoposide, vincristine sulfate, vinblastine sulfate, vindesine sulfate, vinorelbine ditartrate, docetaxel hydrate, eribulin masilate, and paclitaxel.

Examples of the hormonal agent include estramustine phosphate sodium, flutamide, bicalutamide, goserelin acetate, leuprorelin acetate, tamoxifen citrate, toremifene citrate, anastrozole, letrozole, exemestane, mepitiostane, medroxyprogesterone acetate, epitiostanol, fosfestrol, fadrozole hydrochloride hydrate, abiraterone, fulvestrant, and aminoglutethimide.

Examples of the platinum compound include carboplatin, cisplatin, nedaplatin, and oxaliplatin.

Examples of the topoisomerase inhibitor include topotecan and sobuzoxane.

Examples of the kinase inhibitor, include erlotinib, gefitinib, and afatinib that are EGFR inhibitors, lapatinib that is a HER2 inhibitor, imatinib that is a BCR-ABL inhibitor, crizotinib that is an ALK inhibitor, regorafenib that is a multikinase inhibitor, and dasatinib.

Examples of the anti-CD20 antibody include rituximab, ibritumomab, ibritumomab tiuxetan, and ocrelizumab.

Examples of the anti-HER2 antibody include trastuzumab, trastuzumab-emtansine, and pertuzumab.

Examples of the anti-EGFR antibody include cetuximab and panitumumab.

An example of the anti-VEGF antibody is bevacizumab.

An example of the proteasome inhibitor is bortezomib.

An example of the HDAC inhibitor is vorinostat.

Examples of the immunomodulatory drug include thalidomide, lenalidomide, pomalidomide, BCG, and an interferon preparation.

Arbitrary two or more of these other drugs may be administered in combination.

The other drugs which can complement and/or enhance the prophylactic and/or therapeutic effect of the compound of the present invention include drugs which have been discovered until now as well as drugs which will be discovered in the future on the basis of the above-mentioned mechanism.

Unless otherwise specified, all of the technical and scientific terms and the abbreviated terms used in the specification have the same meanings as those which are understood normally by persons skilled in the art to which the present invention pertains.

In the specification, the entire contents of all of patent documents and non-patent documents cited explicitly are hereby incorporated by reference.

SYNTHESIS EXAMPLES

A solvent mentioned in a section relating to the separation by chromatography or shown in parentheses in TLC data is an elution solvent or a developing solvent used, wherein the ratio is expressed by volume.

A substance shown in parentheses in NMR data is a solvent used for the measurement.

Each of the compounds used in the specification is named using a computer program "ACD/Name" (registered trademark) which generally names in accordance with the IUPAC nomenclature rule, is named using Chemdraw Ultra (version 12.0, manufactured by CambridgeSoft Corporation), or is named in accordance with the IUPAC nomenclature method.

LC-MS/ELSD was carried out under the following condition.

Condition A;

column: Waters Triart $C_{18}$ (particle diameter: $1.9\times10^{-6}$ m; column length: 30×2.0 mm ID.); flow rate: 1.0 mL/min; column temperature: 30° C.; mobile phase (A): a 0.1% aqueous trifluoroacetic acid solution (also abbreviated as "TFA", hereinafter); mobile phase (B): a 0.1% TFA-acetonitrile solution; gradient (the (mobile phase A):(mobile phase B) ratio): [0 minutes] 95:5; [0.1 minutes] 95:5; [1.2 minutes] 5:95; [1.4 minutes] 5:95; [1.41 minutes] 95:5; [1.5 minutes] 95:5; detector: UV (PDA), ELSD, MS.

Condition B;

column: Waters Triart $C_{18}$ (particle diameter: $1.9\times10^{-6}$ m; column length: 30×2.0 mm ID.); flow rate: 1.0 mL/min; column temperature: 30° C.; mobile phase (A): a 0.1% TFA; mobile phase (B): a 0.1% TFA-acetonitrile solution; gradient (the (mobile phase A):(mobile phase B) ratio): [0 minutes] 95:5; [0.15 minutes] 95:5; [1.15 minutes] 5:95; [2.80 minutes]5:95; [2.81 minutes] 95:5; [3 minutes] 95:5; detector: UV(PDA), ELSD, MS.

Condition C;

column: ACQUITY UPLC BEH $C_{18}$ (particle diameter: $1.7\times10^{-6}$ m; column length: 50×2.1 mm ID.); flow rate: 0.6 mL/min; column temperature: 35° C.; mobile phase (A): a 0.1% TFA; mobile phase (B): a 0.1% TFA-acetonitrile solution; gradient (the (mobile phase A):(mobile phase B) ratio): [0 minutes] 97:3; [0.4 minutes] 97:3; [2.5 minutes] 298; [3.5 minutes] 2:98; [4.01 minutes] 97:3; detector: UV (PDA), ELSD, MS.

Condition D;

column: Xbridge $C_{18}$ (particle diameter: $3.5\times10^{-6}$ m; flow rate: 1.000 mL/min; column temperature: 35° C.; mobile phase (A): an 10 mM aqueous ammonium bicarbonate solution; mobile phase (B): acetonitrile; gradient (the (mobile phase A):(mobile phase B) ratio): [0 minutes] 95:5; [0.8 minutes] 95:5; [5 minutes] 2:98; [6 minutes] 2:98; [8.01 minutes] 95:5; detector: UV(PDA), ELSD, MS.

Condition E;

column: ACQUITY UPLC BEH $C_{18}$ (particle diameter: $1.7\times10^{-6}$ m; column length: 50×2.1 mm); flow rate: 0.6 mL/min; column temperature: 35° C.; mobile phase (A): 0.05% TFA; mobile phase (B): a 0.05% TFA-acetonitrile solution; gradient (the (mobile phase A):(mobile phase B) ratio): [0 minutes] 97:3; [0.4 minutes] 97:3; [2.5 minutes] 2:98; [3.5 minutes] 2:98; [3.8 minutes] 97:3; detector: UV (PDA), ELSD, MS.

Condition F;

column: ACQUITY UPLC BEH $C_{18}$ (particle diameter: $1.7\times10^{-6}$ m; column length: 50×2.1 mm); flow rate: 0.6 mL/min; column temperature: 35° C.; mobile phase (A): 0.07% TFA; mobile phase (B): a 0.07% TFA-acetonitrile solution; gradient (the (mobile phase A):(mobile phase B) ratio): [0 minutes] 97:3; [0.4 minutes] 97:3; [2.5 minutes] 2 98; [3.5 minutes] 2:98; [3.8 minutes] 97:3; detector: UV (PDA), ELSD, MS.

The HPLC retention time shows a retention time under condition A mentioned in the LC-MS/ELSD, unless otherwise specified.

As the microwave reaction device, "Initiator 60 EXP" manufactured by Biotage was used.

The preparatory purification by high-performance liquid chromatography (also abbreviated as "HPLC", hereinafter) was carried out under the following conditions.

Mobile phase A (0.1% TFA): mobile phase B (0.10% TFA/acetonitrile)=95:5→5:95

Reference Example 1: Ethyl 5-(3-phenylpropyl)-1H-pyrrole-2-carboxylate

Bicyclo[2.2.2]-2-heptene (also abbreviated as "norbornene", hereinafter) (CAS Number: 498-66-8, 3.40 g), potassium bicarbonate (5.40 g) and bis(acetonitrile)dichloropalladium (II) (CAS Number: 14592-56-4, 230 mg) were added to a solution of ethyl 1H-pyrrole-2-carboxylate (CAS Number: 2199-43-1, 2.50 g) in N,N-dimethylacetamide (also abbreviated as "DMA", hereinafter) (3 mL), and the resultant solution was degassed with ultrasonic waves. 1-Bromo-3-phenylpropane (CAS Number: 637-59-2, 7.20 g) was added to the reaction mix solution, and the resultant solution was stirred at 90° C. for 20 hours. The reaction solution was diluted with (ethyl acetate): hexane (1:1), and the resultant solution was filtrated through Celite (trade name). The filtrate was washed with a saturated aqueous ammonium chloride solution and saturated saline, was then dried over sodium sulfate anhydride, and a dried product was concentrated under a reduced pressure. The resultant residue was purified by silica gel column chromatography (hexane:(ethyl acetate)=95:5→3:1). In this manner, the title compound (3.82 g) having the following physical property values was produced.

HPLC retention time (min): 1.12;

MS(ESI, Pos.): 258 $(M+H)^+$.

Reference Example 2: Ethyl 1-(butan-2-yl)-5-(3-phenylpropyl)-1H-pyrrole-2-carboxylate 2-Butanol (0.78 g) and cyanomethylenetributylphosphorane (also abbreviated as "CMBP", hereinafter) (CAS Number: 157141-27-0, 0.76 g) were added to a solution of the compound produced in Reference Example 1 (0.27 g) in toluene (5 mL), and the resultant solution was stirred using a microwave device at 130° C. for 3 hours. The reaction solution was concentrated under a reduced pressure, and the resultant residue was purified by silica gel column chromatography (hexane:(ethyl acetate)=100:0→9:1). In this manner, the title compound (0.24 g) having the following physical property values was produced.

HPLC retention time (min): 1.34;

MS(ESI, Pos.): 314 $(M+H)^+$.

Reference Example 3: 1-(Butan-2-yl)-5-(3-phenylpropyl)-1H-pyrrole-2-carboxylic acid Methanol (2 mL) and a 50% aqueous potassium hydroxide solution (1 mL) were added to a solution of the compound produced in Reference Example 2 (0.24 g) in 1,2-dimethoxyethane (also abbreviated as "DME", hereinafter) (2 mL), and the resultant solution was stirred at 90° C. for 22 hours. The reaction solution was cooled in the air, was then made acidic with 1N hydrochloric acid, and was then extracted with ethyl acetate. An organic layer was dried over sodium sulfate anhydride, and a dried product was concentrated under a reduced pressure. The resultant residue was purified by silica gel column chromatography (hexane:(ethyl acetate)=95:5→4:1). In this manner, the title compound (0.18 g) having the following physical property values was produced.

HPLC retention time (min): 1.13;

MS(ESI, Pos.): 286 $(M+H)^+$.

Reference Examples 3-1 to 3-2

The same reactions as in Reference Example 2→Reference Example 3 were carried out using, in place of 2-butanol, each of corresponding alcohols. In this manner, the title compounds having the following physical property values were produced.

Reference Example 3-1: 1-[(2S)-Butan-2-yl]-5-(3-phenylpropyl)-1H-pyrrole-2-carboxylic acid HPLC retention time (min): 1.10;

MS(ESI, Pos.): 286 $(M+H)^+$.

Reference Example 3-2: 5-(3-Phenylpropyl)-1-(propan-2-yl)-1H-pyrrole-2-carboxylic acid HPLC retention time (min): 1.10;

MS(ESI, Pos.): 272 $(M+H)^+$.

Reference Example 4: Ethyl rel-(1R,2S)-2-[3-amino-4-(trifluoromethyl)phenyl]cyclopropane-1-carboxylate Racemic Mixture Ethyl 2-(4,4,5,5-tetramethyl-1,3,2-dioxaborolan-2-yl)cyclopropanecarboxylate (CAS Number: 1215107-29-1, 3 g), a 2M aqueous potassium phosphate solution (18.8 mL) and [1,1'-bis(diphenylphosphino)ferrocene]palladium(II) dichloride-dichloromethane adduct (CAS Number: 95464-05-4, 1 g) were added to a solution of 5-bromo-2-(trifluoromethyl)aniline (CAS Number: 703-91-3, 3 g) in 1,4-dioxane (60 mL), and the resultant solution was stirred at 100° C. for 2 hours. The reaction solution was diluted with ethyl acetate, the resultant solution was washed with water and saturated saline and was then dried over sodium sulfate anhydride, and a dried product was concentrated under a reduced pressure. The resultant residue was purified by HPLC. In this manner, the title compound (0.8 g) having the following physical property values was produced.

HPLC retention time (min): 1.03;

MS(ESI, Pos.): 273 $(M+H)^+$.

Reference Example 5: 5-(5,5-Dimethyl-1,3,2-dioxaborinan-2-yl)-2-(trifluoromethyl)aniline Potassium acetate (1.2 g) and [1,1'-bis(diphenylphosphino)ferrocene]palladium(II) dichloride-dichloromethane adduct (340 mg) were added to a solution of 5-bromo-2-(trifluoromethyl)aniline (1 g) and bis(neopentyl glycolato) diboron (CAS Number: 201733-56-4, 1.9 g) in dimethyl sulfoxide (also abbreviated as "DMSO", hereinafter) (10 mL), and the resultant solution was stirred at 100° C. for 2 hours. The reaction solution was diluted with water, and the resultant solution was extracted with 2-methoxy-2-methylpropane (also abbreviated as "MTBE", hereinafter). An organic layer was washed with saturated saline and was then dried over sodium sulfate anhydride, and a dried product was concentrated under a reduced pressure. The resultant residue was purified by silica gel column chromatography (hexane:(ethyl acetate)=9:1→0:1). In this manner, the title compound (1 g) having the following physical property values was produced.

$^1$H-NMR ($CDCl_3$): δ1.55, 3.76, 4.06-4.15, 7.16-7.21, 7.39-7.42.

Reference Example 6: Ethyl (1R,2S)-2-[3-amino-4-(trifluoromethyl)phenyl]cyclopropane-1-carboxylate A 2M aqueous cesium carbonate solution (2.2 mL) and chloro(2-dicyclohexylphosphino-2',4',6'-triisopropylbiphenyl)(2'-aminobiphenyl-2-yl)palladium (II) (also abbreviated as "XPhos Pd G2", hereinafter) (CAS Number: 1310584-14-5, 236 mg) were added to a solution of the compound produced in Reference Example 5 (491 mg) and ethyl (1S,2S)-2-iodocyclopropanecarboxylate (CAS Number: 1629125-76-3, 400 mg) in 1,4-dioxane (10 mL), and the resultant solution was stirred at 100° C. for 4.5 hours. The reaction solution was diluted with ethyl acetate, the resultant solution was washed with water and saturated saline and was then dried over sodium sulfate anhydride, and a dried product was concentrated under a reduced pressure. The resultant residue was purified by silica gel column chromatography (NH silica) (hexane:(ethyl acetate)=9:1→0:1) and silica gel column chromatography (hexane:(ethyl acetate) =9:1→1:1). In this manner, the title compound (110 mg) having the following physical property values was produced.

HPLC retention time (min): 0.95;

MS(ESI, Pos.): 274 $(M+H)^+$.

Reference Example 7: Ethyl (1R,2S)-2-[5-amino-2-chloro-4-(trifluoromethyl)phenyl]cyclopropane-1-carboxylate N-Chlorosuccinimide (CAS Number: 128-09-6, 37 mg) was added to a solution of the compound produced in Reference Example 6 (50 mg) in DMF (1 mL), and the resultant solution was stirred at 60° C. for 1 hour. The reaction solution was purified by silica gel column chromatography (hexane:(ethyl acetate)=9:1→0:1). In this manner, the title compound (13 mg) having the following physical property values was produced.

HPLC retention time (min): 1.02;

MS(ESI, Pos.): 308 $(M+H)^+$.

Reference Example 8: Ethyl rel-(1R,2S)-2-[3-{[1-(butan-2-yl)-5-(3-phenylpropyl)-1H-pyrrole-2-carbonyl]amino}-4-(trifluoromethyl)phenyl]cyclopropane-1-carboxylate Racemic Mixture N,N-Diisopropylethylamine (also abbreviated as "DIPEA", hereinafter) (CAS Number: 7087-68-5, 135 mg) and chloro-N,N,N',N'-tetramethylformamidinium-hexafluorophosphate (also abbreviated as "TCFH", hereinafter) (CAS Number: 94790-35-9, 147 mg) were added to a solution of the compound produced in Reference Example 4 (105 mg) and the compound produced in Reference Example 3 (100 mg) in dichloromethane (1 mL), and the resultant solution was stirred at room temperature for 13 hours. The reaction solution was concentrated under a reduced pressure, and the resultant product was purified by HPLC. In this manner, the title compound (100 mg) having the following physical property values was produced.

HPLC retention time (min): 1.39;

MS(ESI, Pos.): 541 $(M+H)^+$.

Example 1: rel-(1R,2S)-2-[3-({[1-sec-Butyl-5-(3-phenylpropyl)-1H-pyrrole-2-carbonyl]amino)-4-(trifluoromethyl)phenyl]cyclopropanecarboxylic acid Racemic Mixture

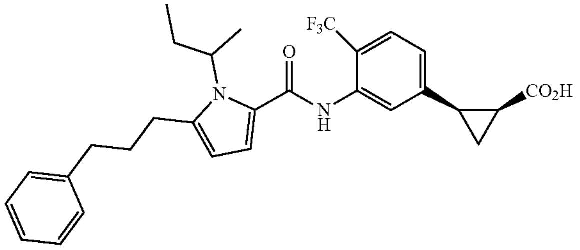

and

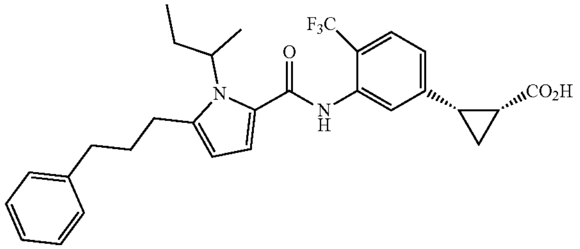

A 5N aqueous sodium hydroxide solution (0.5 mL) was added to a solution of the compound produced in Reference Example 8 (95 mg) in tetrahydrofuran (also abbreviated as "THF", hereinafter) (2.5 mL) and methanol (2.5 mL), and the resultant solution was stirred at room temperature for 3.5 hours. The reaction solution was neutralized with 5N hydrochloric acid, and the resultant solution was extracted with ethyl acetate. An organic layer was washed with saturated saline, was then dried over sodium sulfate anhydride, and a dried product was concentrated under a reduced pressure. In this manner, the compound of the present invention (82 mg) having the following physical property values was produced.

HPLC retention time (min): 1.22;

MS(ESI, Pos.): 513 $(M+H)^+$;

$^1$H-NMR ($CDCl_3$): δ0.58-0.82, 1.34-1.53, 1.61-2.22, 2.54-2.81, 4.63-5.18, 5.93-6.04, 6.58-6.71, 7.07-7.13, 7.17-7.24, 7.28-7.35, 7.46-7.54, 7.86-7.97, 8.06-8.18.

Reference Example 9: N-[5-Bromo-2-(trifluoromethyl)phenyl]-1-[(2S)-butan-2-yl]-5-(3-phenylpropyl)-1H-pyrrole-2-carboxamide The same reaction as in Reference Example 8 was carried out using, in place of the compound produced in Reference Example 4, 5-bromo-2-(trifluoromethyl)aniline and also using, in place of the compound produced in Reference Example 3, the compound produced in Reference Example 3-1. In this manner, the title compound having the following physical properties was produced.

HPLC retention time (min): 1.43;

MS(ESI, Pos.): 507 $(M+H)^+$.

Reference Example 10: Ethyl 2-[3-({1-[(2S)-butan-2-yl]-5-(3-phenylpropyl)-1H-pyrrole-2-carbonyl}amino)-4-(trifluoromethyl)phenyl]cyclopropane-1-carboxylate Ethyl 2-(4,4,5,5-tetramethyl-1,3,2-dioxaborolan-2-yl)cyclopropanecarboxylate (94 mg), a 2M aqueous potassium phosphate solution (0.59 mL) and [1,1'-bis(diphenylphosphino)ferrocene]palladium(II) dichloride-dichloromethane adduct (96 mg) were added to a solution of the compound produced in Reference Example 9 (200 mg) in 1,4-dioxane (2 mL), and the resultant solution was stirred using a microwave device at 120° C. for 1 hour. The reaction solution was used in the subsequent reaction without being purified.

Example 2: rel-(1R,2S)-2-{3-[({1-[(2S)-2-Butanyl]-5-(3-phenylpropyl)-1H-pyrrol-2-yl}carbonyl)amino]-4-(trifluoromethyl)phenyl}cyclopropanecarboxylic acid Diastereomer Mixture

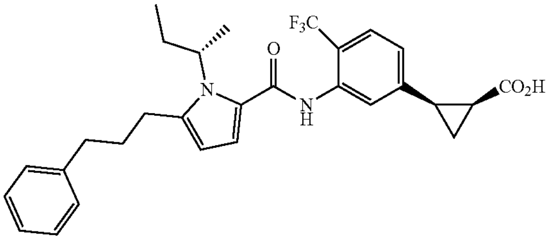
and

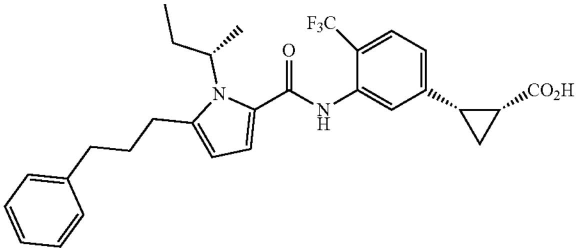

A 5N aqueous sodium hydroxide solution (1 mL) was added to the reaction solution produced in Reference Example 10, and the resultant solution was stirred at 50° C. for 2 hours. The reaction solution was made acidic with 5N hydrochloric acid, and was then extracted with ethyl acetate. An organic layer was washed with saturated saline, was then dried over sodium sulfate anhydride, was then concentrated under a reduced pressure, and was then purified by HPLC. In this manner, the compound of the present invention (45 mg) having the following physical property values was produced.

HPLC retention time (min): 1.22;

MS(ESI, Pos.): 513 $(M+H)^+$;

$^1$H-NMR ($CDCl_3$): δ0.76, 1.36-1.45, 1.51, 1.62-1.72, 1.73-1.87, 1.90-2.14, 2.57-2.79, 4.58-5.27, 5.98, 6.65, 7.03, 7.17-7.24, 7.28-7.35, 7.47, 7.94, 8.22.

Examples 2-1 to 2-4

The same procedures as in Reference Example 9→Reference Example 10→Example 2 were carried out using, in place of 5-bromo-2-(trifluoromethyl)aniline, each of corresponding aniline derivatives, and also using ethyl 2-(4,4,5,5-tetramethyl-1,3,2-dioxaborolan-2-yl)cyclopropanecarboxylate or a corresponding boronic acid ester. In this manner, the compounds of the present invention having the following physical properties were produced.

Example 2-1: rel-(1R,2S)-2-{3-[({1-[(2S)-2-Butanyl]-5-(3-phenylpropyl)-1H-pyrrol-2-yl}carbonyl)amino]-5-methylphenyl}cyclopropanecarboxylic acid Diastereomer Mixture

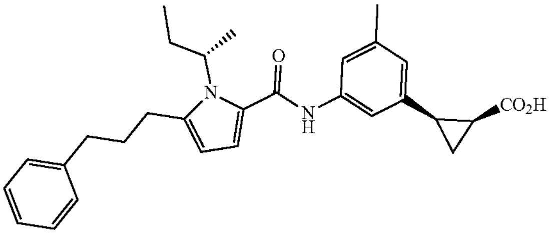
and

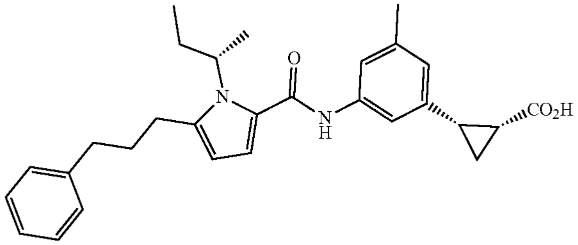

HPLC retention time (min): 1.36;

MS(ESI, Pos.): 459 $(M+H)^+$;

$^1$H-NMR ($CDCl_3$): δ0.68-0.81, 1.31-1.39, 1.50, 1.61-1.87, 1.96-2.12, 2.26-2.30, 2.51-2.80, 4.21-5.10, 5.95, 6.61, 6.83, 7.11-7.36, 7.58.

Example 2-2: rel-(1R,2R)-2-{3-[({1-[(2S)-2-Butanyl]-5-(3-phenylpropyl)-1H-pyrrol-2-yl}carbonyl)amino]-5-methylphenyl}cyclopropanecarboxylic acid Diastereomer Mixture

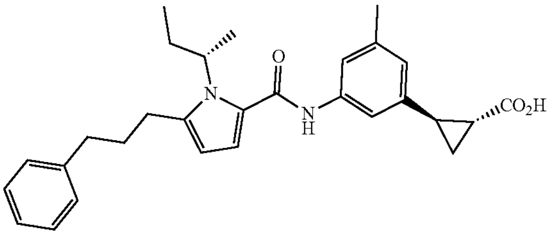
and

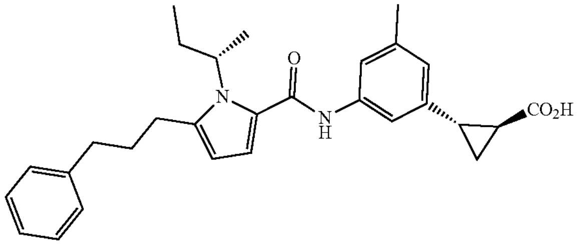

HPLC retention time (min): 1.38;

MS(ESI, Pos.): 459 $(M+H)^+$;

$^1$H-NMR ($CDCl_3$): δ0.76, 1.36-1.47, 1.52, 1.57-1.66, 1.71-2.08, 2.31, 2.49-2.61, 2.65-2.81, 4.43-5.37, 5.95, 6.59, 6.65, 7.09-7.36, 7.49-7.57.

Example 2-3: rel-(1R,2S)-2-{5-[({1-[(2S)-2-Butanyl]-5-(3-phenylpropyl)-1H-pyrrol-2-yl}carbonyl) amino]-2-(trifluoromethyl) phenyl}cyclopropanecarboxylic acid Diastereomer Mixture

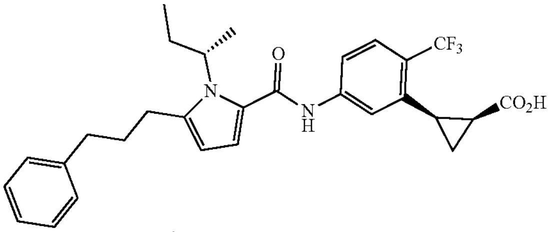

and

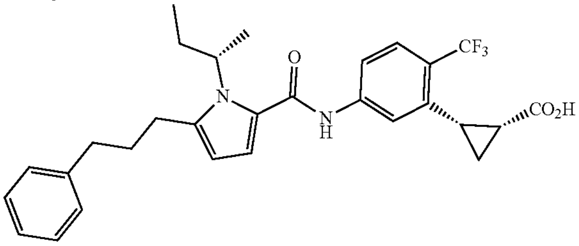

HPLC retention time (min): 1.41;

MS(ESI, Pos.): 513 $(M+H)^+$;

$^1$H-NMR ($CDCl_3$): δ0.73-0.80, 1.42-1.57, 1.95-2.09, 2.14-2.28, 2.61-2.87, 4.32-5.33, 5.97, 6.67, 7.17-7.36, 7.42, 7.54-7.59, 7.62-7.78.

Example 2-4: rel-(1R,2R)-2-{5-[({1-[(2S)-2-Butanyl]-5-(3-phenylpropyl)-1H-pyrrol-2-yl}carbonyl) amino]-2-(trifluoromethyl) phenyl}cyclopropanecarboxylic acid Diastereomer Mixture

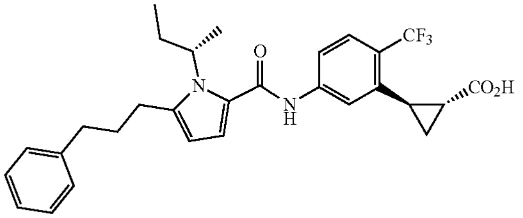

and

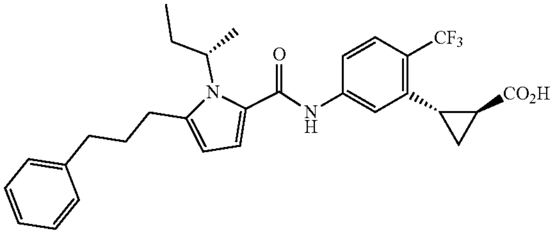

HPLC retention time (min): 1.43;

MS(ESI, Pos.): 513 $(M+H)^+$;

$^1$H-NMR ($CDCl_3$): δ0.77, 1.47-1.57, 1.63-1.88, 1.90-2.08, 2.63-2.93, 4.26-5.25, 5.98, 6.66, 7.12-7.34, 7.39, 7.44-7.50, 7.57-7.62, 7.68.

Examples 3-1 to 3-2

The same reactions as in Reference Example 2→Reference Example 3→Reference Example 9→Reference Example 10→Example 1 were carried out using, in place of 2-butanol, isopropanol and also using, in place of ethyl 2-(4,4,5,5-tetramethyl-1,3,2-dioxaborolan-2-yl)cyclopropanecarboxylate, each of corresponding boronic acid esters. In this manner, the compounds of the present invention having the following physical property values were produced.

Example 3-1: (1S,2R)-2-[3-({[1-Isopropyl-5-(3-phenylpropyl)-1H-pyrrol-2-yl]carbonyl}amino)-4-(trifluoromethyl)phenyl]cyclopropanecarboxylic acid

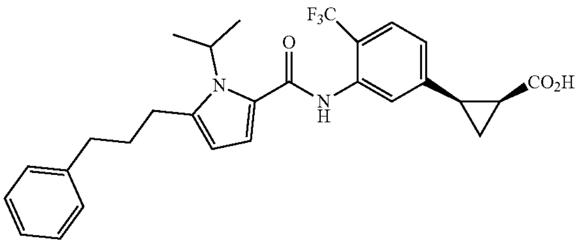 [SMILES: CC(C)n1c(CCCc2ccccc2)ccc1C(=O)Nc1cc([C@@H]2C[C@@H]2C(=O)O)ccc1C(F)(F)F]

HPLC retention time (min): 1.19;

MS(ESI, Pos.): 499 $(M+H)^+$;

$^1$H-NMR ($CDCl_3$): δ1.39-1.47, 1.52, 1.64-1.74, 1.96-2.13, 2.58-2.80, 5.00-5.21, 5.97, 6.65, 6.90-7.17, 7.17-7.24, 7.28-7.36, 7.48, 7.95, 8.26.

Example 3-2: (1R,2R)-2-[3-({[1-Isopropyl-5-(3-phenylpropyl)-1H-pyrrol-2-yl]carbonyl}amino)-4-(trifluoromethyl)phenyl]cyclopropanecarboxylic acid

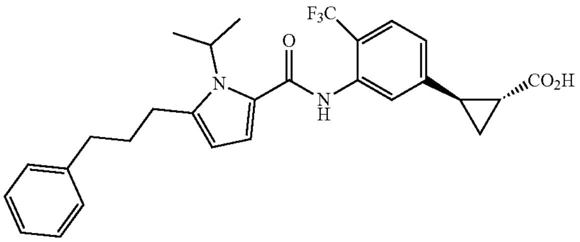 [SMILES: CC(C)n1c(CCCc2ccccc2)ccc1C(=O)Nc1cc([C@@H]2C[C@H]2C(=O)O)ccc1C(F)(F)F]

HPLC retention time (min): 1.21;

MS(ESI, Pos.): 499 $(M+H)^+$;

$^1$H-NMR ($CDCl_3$): δ1.45-1.51, 1.54, 1.66-1.76, 1.96-2.09, 2.60-2.83, 5.05-5.18, 5.97, 6.65, 6.89, 7.18-7.24, 7.28-7.34, 7.51, 7.98, 8.17.

Reference Example 11: 4-Iodo-1-methoxy-2-nitrobenzene

A 28% solution of sodium methoxide in methanol (7.3 mL) was added to a solution of 1-fluoro-4-iodo-2-nitrobenzene (CAS Number: 364-75-0, 3.2 g) in methanol (10 mL), and the resultant solution was stirred at 50° C. for 15 hours. The reaction solution was diluted with ethyl acetate, the resultant solution was washed with water and saturated saline, was then dried over sodium sulfate anhydride, and a dried product was concentrated under a reduced pressure. In this manner, the title compound (3.3 g) having the following physical property values was produced.

HPLC retention time (min): 0.94;

$^1$H-NMR ($CDCl_3$): δ3.95, 6.87, 7.81, 8.12.

Reference Example 12: 5-Iodo-2-methoxyaniline

Water (1 mL) and an iron powder (1.4 g) were added to a solution of the compound produced in Reference Example 11 (2.3 g) in acetic acid (10 mL), and the resultant solution was stirred at 50° C. for 6 hours. The reaction solution was diluted with MTBE and hexane, and the resultant solution was filtrated through Celite (trade name). The filtrate was washed with a 2N aqueous sodium hydroxide solution and saturated saline and was then dried over sodium sulfate anhydride, and a dried product was concentrated under a reduced pressure. The resultant residue was purified by silica gel column chromatography (NH silica) (hexane:(ethyl acetate)=9:1→1:1). In this manner, the title compound (1.8 g) having the following physical property values was produced.

HPLC retention time (min): 0.63;

MS(ESI, Pos.): 250 $(M+H)^+$.

Reference Example 13: 1-[(2S)-Butan-2-yl]-N-(5-iodo-2-methoxyphenyl)-5-(3-phenylpropyl)-1H-pyrrole-2-carboxamide The same reaction as in Reference Example 8 was carried out using, in place of the compound produced in Reference Example 4, the compound produced in Reference Example 12 and also using, in place of the compound produced in Reference Example 3, the compound produced in Reference Example 3-1. In this manner, the title compound having the following physical properties was produced.

HPLC retention time (min): 1.41;

MS(ESI, Pos.): 517 $(M+H)^+$.

Reference Example 14: 1-[(2S)-Butan-2-yl]-N-[5-(5,5-dimethyl-1,3,2-dioxaborinan-2-yl)-2-methoxyphenyl]-5-(3-phenylpropyl)-1H-pyrrole-2-carboxamide Potassium acetate (28 mg) and [1,1'-bis(diphenylphosphino)ferrocene]palladium(II) dichloride-dichloromethane adduct (8 mg) were added to a solution of the compound produced in Reference Example 13 (50 mg) and bis(neopentyl glycolato)diboron (43 mg) in DMSO (1 mL), and the resultant solution was stirred at 100° C. for 1 hour. The reaction solution was diluted with MTBE, the resultant solution was washed with water and saturated saline and was then dried over sodium sulfate anhydride, and a dried product was concentrated under a reduced pressure. The resultant residue was purified by silica gel column chromatography (hexane:(ethyl acetate)=9:1→0:1). In this manner, the title compound (35 mg) having the following physical property values was produced.

HPLC retention time (min): 1.14.

Reference Example 15: Ethyl (1R,2S)-2-{3-[({1-[(2S)-2-butanyl]-5-(3-phenylpropyl)-1H-pyrrol-2-yl}carbonyl)amino]-4-methoxyphenyl}cyclopropanecarboxylate A 2M aqueous cesium carbonate solution (0.17 mL) and XPhos Pd G2 (11 mg) were added to a solution of the compound produced in Reference Example 14 (35 mg) and ethyl (1S,2S)-2-iodocyclopropanecarboxylate (22.3 mg) in 1,4-dioxane (1 mL), and the resultant solution was stirred at 100° C. for 30 minutes. The reaction solution was used in the subsequent reaction without being purified.

Example 4: (1R,2S)-2-{3-[({1-[(2S)-2-Butanyl]-5-(3-phenylpropyl)-1H-pyrrol-2-yl}carbonyl)amino]-4-methoxyphenyl}cyclopropanecarboxylic acid

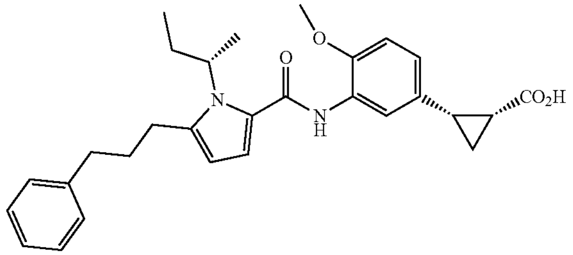 [SMILES: CC[C@H](C)n1c(CCCc2ccccc2)ccc1C(=O)Nc1cc([C@H]2C[C@H]2C(=O)O)ccc1OC]

Methanol (1 mL) and a 5N aqueous sodium hydroxide solution (1 mL) were added to the reaction solution obtained in Reference Example 15, and the resultant solution was stirred at 50° C. for 1 hour. The reaction solution was cooled to room temperature, was then neutralized with 5N hydrochloric acid, and was then extracted with MTBE. An organic layer was washed with saturated saline, and was then dried over sodium sulfate anhydride, and a dried product was concentrated under a reduced pressure. The resultant residue was purified by HPLC. In this manner, the compound of the present invention (3 mg) having the following physical property values was produced.

HPLC retention time (min): 1.39;

MS(ESI, Pos.): 475 $(M+H)^+$;

$^1$H-NMR ($CDCl_3$): δ0.72-0.81, 1.33-1.44, 1.48-1.55, 1.62-1.71, 1.75-2.16, 2.59-2.79, 3.83-3.87, 4.62-5.16, 5.93-5.99, 6.59-6.66, 6.75-6.81, 6.87-6.94, 7.14-7.24, 7.27-7.35, 8.17-8.27, 8.32-8.36.

Reference Example 16: (1R,2S,5R)-5-Methyl-2-(propan-2-yl)cyclohexyl rel-(1R,2S)-2-[3-({1-[(2S)-butan-2-yl]-5-(3-phenylpropyl)-1H-pyrrole-2-carbonyl}amino)-4-(trifluoromethyl)phenyl] cyclopropane-1-carboxylate Diastereomer Mixture DIPEA (63 mg), L-menthol (45 mg), 4-dimethylaminopyridine (also abbreviated as "DMAP", hereinafter) and 1-(chloro-1-pyrrolidinylmethylene)pyrrolidinium hexafluorophosphate (also abbreviated as "CyCIU", hereinafter) (CAS Number: 135540-11-3, 65 mg) were added to a solution of the compound produced in Example 2 (50 mg) in dichloromethane (1 mL) and acetonitrile (1 mL), and the resultant solution was stirred at 70° C. for 2 hours. The reaction solution was concentrated and was used in the subsequent resolution.

Reference Examples 16-1 to 16-2: Resolution

The mixture produced in Reference Example 16 was purified by HPLC. In this manner, the title compounds having the following physical property values were produced.

Reference Example 16-1: (1R,2S,5R)-5-Methyl-2-(propan-2-yl)cyclohexyl (1S,2R)-2-[3-({1-[(2S)-butan-2-yl]-5-(3-phenylpropyl)-1H-pyrrole-2-carbonyl}amino)-4-(trifluoromethyl)phenyl] cyclopropane-1-carboxylate HPLC retention time (min): 1.67 (condition B);

MS(ESI, Pos.): 651 $(M+H)^+$.

Reference Example 16-2: (1R,2S,5R)-5-Methyl-2-(propan-2-yl)cyclohexyl (1R,2S)-2-[3-({1-[(2S)-butan-2-yl]-5-(3-phenylpropyl)-1H-pyrrole-2-carbonyl}amino)-4-(trifluoromethyl)phenyl] cyclopropane-1-carboxylate HPLC retention time (min): 1.70 (condition B);

MS(ESI, Pos.): 651 $(M+H)^+$.

Example 5: (1S,2R)-2-{3-[({1-[(2S)-2-Butanyl]-5-(3-phenylpropyl)-1H-pyrrol-2-yl}carbonyl)amino]-4-(trifluoromethyl)phenyl}cyclopropanecarboxylic acid

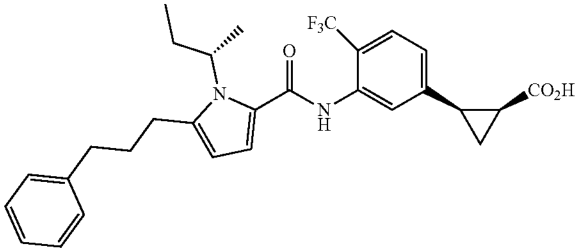 [SMILES: CC[C@H](C)n1c(CCCc2ccccc2)ccc1C(=O)Nc1cc([C@@H]2C[C@@H]2C(=O)O)ccc1C(F)(F)F]

A 5N aqueous sodium hydroxide solution (1 mL) was added to a solution of the compound produced in Reference Example 16-1 in methanol (1 mL) and THE (1 mL), and the resultant solution was stirred at 50° C. for 1 hour. The reaction solution was neutralized with 5N hydrochloric acid, and was then extracted with ethyl acetate. An organic layer was washed with saturated saline, was then dried over sodium sulfate anhydride, and was concentrated under a reduced pressure. In this manner, the compound of the present invention (16 mg) having the following physical property values was produced.

HPLC retention time (min): 1.29;

MS(ESI, Pos.): 513 $(M+H)^+$;

$^1$H-NMR ($CDCl_3$): δ0.72-0.81, 1.17-1.47, 1.48-1.54, 1.63-1.87, 1.92-2.16, 2.58-2.80, 4.38-4.84, 5.95-6.01, 6.62-6.68, 7.03-7.08, 7.17-7.24, 7.28-7.35, 7.44-7.51, 7.91-7.98, 8.19-8.24.

Example 6: (1R,2S)-2-{3-[({1-[(2S)-2-Butanyl]-5-(3-phenylpropyl)-1H-pyrrol-2-yl}carbonyl)amino]-4-(trifluoromethyl)phenyl}cyclopropanecarboxylic acid

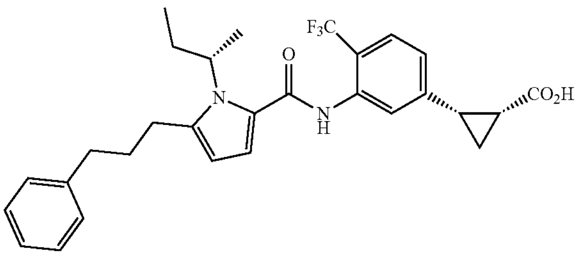 [SMILES: CC[C@H](C)n1c(CCCc2ccccc2)ccc1C(=O)Nc1cc([C@H]2C[C@H]2C(=O)O)ccc1C(F)(F)F]

A 5N aqueous sodium hydroxide solution (1 mL) was added to a solution of the compound produced in Reference Example 16-2 in methanol (1 mL) and THE (1 mL), and the resultant solution was stirred at 50° C. for 1 hour. The reaction solution was neutralized with 5N hydrochloric acid, and was then extracted with ethyl acetate. An organic layer was washed with saturated saline, was then dried over sodium sulfate anhydride, and a dried product was concentrated under a reduced pressure. In this manner, the compound of the present invention (11 mg) having the following physical property values was produced.

HPLC retention time (min): 1.29;

MS(ESI, Pos.): 513 $(M+H)^+$;

$^1$H-NMR ($CDCl_3$): δ0.76, 1.37-1.46, 1.52, 1.62-1.72, 1.73-1.86, 1.89-2.17, 2.56-2.82, 4.34-5.29, 5.98, 6.65, 7.02, 7.17-7.24, 7.27-7.35, 7.47, 7.94, 8.22.

Example 7: (1R,2S)-2-{3-[({1-[(2S)-2-Butanyl]-5-(3-phenylpropyl)-1H-pyrrol-2-yl}carbonyl)amino]-4-chlorophenyl}cyclopropanecarboxylic acid

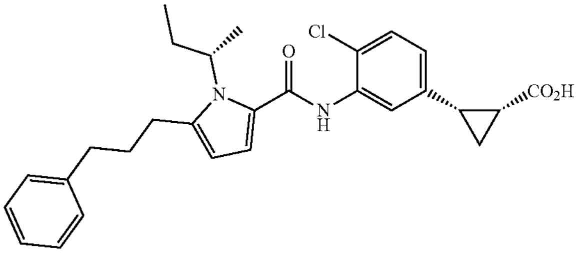 [SMILES: CC[C@H](C)n1c(CCCc2ccccc2)ccc1C(=O)Nc1cc([C@H]2C[C@H]2C(=O)O)ccc1Cl]

The same procedures as in Reference Example 9→Reference Example 10→Example 1 were carried out using, in place of the compound produced in Reference Example 4, 5-bromo-2-chloroaniline. In this manner, the compound of the present invention having the following physical property values was produced.

HPLC retention time (min): 1.41;

MS(ESI, Pos.): 479 $(M+H)^+$;

$^1$H-NMR (DMSO-$d_6$): δ0.62-0.69, 1.11-1.51, 1.63-2.12, 2.34-2.80, 4.58-5.26, 5.88-6.00, 6.83-6.88, 6.97-7.07, 7.12-7.41, 7.50-7.56, 9.20-9.24, 11.90.

Reference Example 17: Ethyl 5-[2-(benzyloxy) ethyl]-1H-pyrrole-2-carboxylate

Potassium bicarbonate (80 g), 2-bromoethoxymethylbenzene (CAS Number: 1462-37-9, 57 g) and bis(acetonitrile)

dichloropalladium (II) (3.5 g) were added to a solution of ethyl 1H-pyrrole-2-carboxylate (37 g) and norbornene (50 g) in DMA (265 mL), and the resultant solution was stirred at 100° C. for 24 hours. Water was added to the reaction solution, the resultant solution was filtrated through Celite (trade name), and the filtrate was extracted with ethyl acetate. An organic layer was washed with water and saturated saline, and was then dried over sodium sulfate anhydride, and a dried product was concentrated under a reduced pressure. The resultant residue was purified by silica gel column chromatography (hexane:(ethyl acetate)=8:1→6:1). The resultant residue was dissolved in heptane, the resultant solution was washed with a methanol/water (1:1) mixed solution, a heptane layer was dried over sodium sulfate anhydride, and a dried product was concentrated under a reduced pressure. The resultant residue was purified by silica gel column chromatography (hexane:(ethyl acetate)=99:1→6:4). In this manner, the title compound (11 g) having the following physical property values was produced.

TLC: Rf 0.34 (hexane:(ethyl acetate)=5:1);

HPLC retention time (min): 1.04;

MS(ESI, Pos.): 274 $(M+H)^+$.

Reference Example 18: Ethyl 5-[2-(benzyloxy)ethyl]-1-[(2S)-butan-2-yl]-1H-pyrrole-2-carboxylate (R)-(−)-2-butanol (CAS Number 14898-79-4, 12 mL) and CMBP (12 mL) were added to a solution of the compound produced in Reference Example 17 (6 g) in toluene (22 mL), and the resultant solution was stirred using a microwave device at 130° C. for 3 hours. The reaction solution was concentrated under a reduced pressure, and the resultant residue was purified by silica gel column chromatography (hexane:(ethyl acetate)=95:5). In this manner, the title compound (4.6 g) having the following physical property values was produced.

HPLC retention time (min): 1.32;

MS(ESI, Pos.): 330 $(M+H)^+$.

Reference Example 19: 5-[2-(Benzyloxy)ethyl]-1-[(2S)-butan-2-yl]-1H-pyrrole-2-carboxylic acid A 50% aqueous potassium hydroxide solution (2.7 mL) was added to a solution of the compound produced in Reference Example 18 (3 g) in 1-methylpyrrolidinone (also abbreviated as "NMP", hereinafter) (8 mL) and methanol (2.7 mL), and the resultant solution was stirred at 85° C. for 1 hour. MTBE was added to the reaction solution, the resultant solution was cooled on ice, was then adjusted to pH 5 with a 10% aqueous phosphoric acid solution and was then extracted with ethyl acetate. An organic layer was washed with water and saturated saline, was then dried over sodium sulfate anhydride, and was concentrated under a reduced pressure. In this manner, the title compound (2.7 g) having the following physical property values was produced.

$^1$H-NMR ($CDCl_3$): δ0.69-0.80, 1.45-1.55, 1.74-1.92, 1.96-2.08, 2.91-3.11, 3.69-3.78, 4.53-4.59, 5.16-5.92, 5.95-6.02, 7.09-7.15, 7.27-7.40.

Reference Example 20: Ethyl (1R,2S)-2-{3-[({5-[2-(benzyloxy)ethyl]-1-[(2S)-2-butanyl]-1H-pyrrol-2-yl}carbonyl)amino]-4-(trifluoromethyl)phenyl}cyclopropanecarboxylate The same procedure as in Reference Example 8 was carried out using, in place of the compound produced in Reference Example 3, the compound produced in Reference Example 19 and also using, in place of the compound produced in Reference Example 4, the compound produced in Reference Example 6. In this manner, the title compound (305 mg) having the following physical property values was produced.

HPLC retention time (min): 1.27;

MS(ESI, Pos.): 557 $(M+H)^+$.

Example 8: (1R,2S)-2-{3-[({5-[2-(Benzyloxy)ethyl]-1-[(2S)-2-butanyl]-1H-pyrrol-2-yl}carbonyl)amino]-4-(trifluoromethyl)phenyl}cyclopropanecarboxylic acid

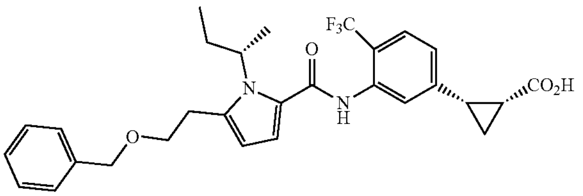 [SMILES: CC[C@H](C)n1c(CCOCc2ccccc2)ccc1C(=O)Nc1cc([C@H]2C[C@H]2C(=O)O)ccc1C(F)(F)F]

The same procedure as in Example 1 was carried out using, in place of the compound produced in Reference Example 8, the compound produced in Reference Example 20. In this manner, the compound of the present invention having the following physical property values was produced.

HPLC retention time (min): 1.13;

MS(ESI, Pos.): 529 $(M+H)^+$;

$^1$H-NMR ($CDCl_3$): δ0.61-0.70, 1.05-1.31, 1.33-1.46, 1.80-2.03, 2.20-2.39, 2.93-3.02, 3.69-3.75, 4.53-4.57, 4.64-4.95, 5.94-5.98, 6.61-6.66, 7.13-7.39, 7.41-7.48, 7.57-7.64, 7.80-7.87.

Reference Example 21: Ethyl 1-[(2S)-butan-2-yl]-5-(2-hydroxyethyl)-1H-pyrrole-2-carboxylate Palladium hydroxide (CAS Number: 12135-22-7, 300 mg) was added to a solution of the compound produced in Reference Example 18 (1.5 g) in ethyl acetate (30 mL), and the resultant solution was stirred at room temperature for 6 hours under a hydrogen atmosphere. The reaction solution was filtrated through Celite (trade name), and was then concentrated under a reduced pressure. The resultant residue was used as it was in the subsequent reaction without being purified.

Reference Example 22: Ethyl 1-[(2S)-butan-2-yl]-5-{2-[(2-fluoropyridin-4-yl)oxy]ethyl}-1H-pyrrole-2-carboxylate CMBP (2.2 g) was added to a solution of the reaction mixture produced in Reference Example 21 and 2-fluoropyridin-4-ol (CAS Number: 22282-69-5, 1 g) in toluene (15 mL), and the resultant solution was stirred at 90° C. for 2 hours. The reaction solution was concentrated under a reduced pressure, and the resultant residue was purified by silica gel column chromatography (hexane:(ethyl acetate)=9:1→0:1). In this manner, the title compound (0.95 g) having the following physical property values was produced.

HPLC retention time (min): 1.20;

MS(ESI, Pos.): 335 $(M+H)^+$.

Reference Example 23: 1-[(2S)-Butan-2-yl]-5-{2-[(2-fluoropyridin-4-yl)oxy]ethyl}-1H-pyrrole-2-carboxylic acid A 5N aqueous sodium hydroxide solution (5 mL) was added to a solution of the compound produced in Reference Example 22 (0.95 g) in NMP (15 mL), and the resultant solution was stirred at 80° C. for 2 hours. The reaction solution was washed with MTBE, and an aqueous layer was neutralized with a 5% aqueous phosphoric acid solution and was then extracted with MTBE. An organic layer was concentrated under a reduced pressure, and the resultant residue was purified by silica gel column chromatography (hexane:(ethyl acetate)=9:1→0:1) and column chromatography using diol silica (Fuji Silysia Chemical Ltd., Chromatorex DIOL60). In this manner, the title compound (0.19 g) having the following physical property values was produced.

HPLC retention time (min): 0.95;

MS(ESI, Pos.): 307 $(M+H)^+$.

Example 9: rel-(1R,2S)-2-[3-{[(1-[(2S)-2-Butanyl]-5-{2-[(2-fluoro-4-pyridinyl)oxy]ethyl}-1H-pyrrol-2-yl)carbonyl]amino}-4-(trifluoromethyl)phenyl]cyclopropanecarboxylic acid Diastereomer Mixture

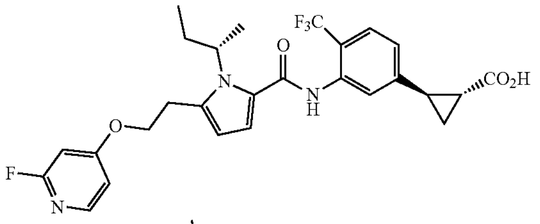

and

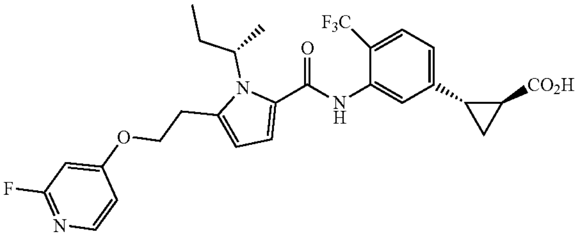

The same procedures as in Reference Example 8→Example 1 were carried out using, in place of the compound produced in Reference Example 3, the compound produced in Reference Example 23. In this manner, the compound of the present invention having the following physical property values was produced.

HPLC retention time (min): 1.11;

MS(ESI, Pos.): 534 $(M+H)^+$;

$^1$H-NMR (DMSO-$d_6$): δ0.70, 1.20-1.28, 1.32-1.39, 1.42-1.57, 1.71-1.87, 2.04-2.12, 2.63-2.74, 3.12-3.20, 4.35-4.41, 4.68-5.27, 6.05, 6.81, 6.92-6.96, 7.29, 7.36-7.41, 7.61, 8.04, 9.44, 11.98.

Reference Example 24: Ethyl (1R,2S)-2-{3-[({1-[(2S)-2-butanyl]-5-(2-hydroxyethyl)-1H-pyrrol-2-yl}carbonyl)amino]-4-(trifluoromethyl)phenyl}cyclopropanecarboxylate A solution of 1M boron tribromide in dichloromethane (CAS Number: 10294-33-4, 0.6 mL) was added to a solution of the compound produced in Reference Example 20 (220 mg) in dichloromethane (10 mL) under ice cooling, and the resultant solution was stirred at room temperature for 2.5 hours. A saturated aqueous sodium bicarbonate solution was added to the reaction solution, and the resultant solution was extracted with ethyl acetate. An organic layer was washed with saturated saline, and was then dried over sodium sulfate anhydride, and a dried product was concentrated under a reduced pressure. The resultant residue was purified by silica gel column chromatography (hexane:(ethyl acetate)=1:9→0:1). In this manner, the title compound (140 mg) having the following physical property values was produced.

HPLC retention time (min): 1.02;

MS(ESI, Pos.): 467 $(M+H)^+$.

Reference Example 25: Ethyl (1R,2S)-2-[3-{[(1-[(2S)-2-butanyl]-5-{2-[(2-chloro-6-fluoro-4-pyridinyl)oxy]ethyl}-1H-pyrrol-2-yl)carbonyl]amino}-4-(trifluoromethyl)phenyl]cyclopropanecarboxylate 2-Chloro-6-fluoropyridin-4-ol (CAS Number: 1807206-99-0, 0.3 g) and CMBP (0.5 g) were added to a suspension of the compound produced in Reference Example 24 (0.8 g) in toluene (20 mL), and the resultant solution was stirred at 90° C. for 1 hour. The reaction solution was concentrated under a reduced pressure, and the resultant residue was purified by silica gel column chromatography (hexane:(ethyl acetate)=3:97→1:1). In this manner, the title compound (0.9 g) having the following physical property values was produced.

HPLC retention time (min): 1.43;

MS(ESI, Pos.): 596 $(M+H)^+$.

Example 10: (1R,2S)-2-[3-{[(1-[(2S)-2-Butanyl]-5-{2-[(2-chloro-6-fluoro-4-pyridinyl)oxy]ethyl}-1H-pyrrol-2-yl)carbonyl]amino}-4-(trifluoromethyl)phenyl]cyclopropanecarboxylic acid

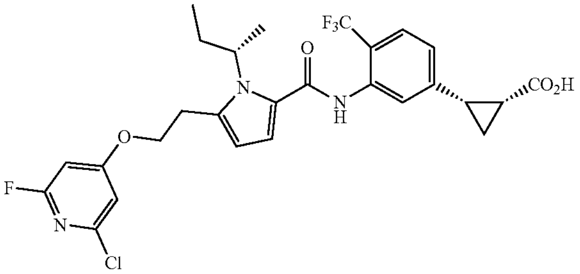 [SMILES: CC[C@H](C)n1c(CCOc2cc(F)nc(Cl)c2)ccc1C(=O)Nc1cc([C@H]2C[C@H]2C(=O)O)ccc1C(F)(F)F]

Sulfuric acid (2 mL) was added to a solution of the compound produced in Reference Example 25 (900 mg) in 1,4-dioxane (10 mL), and the resultant solution was stirred at 100° C. 48 hours. The reaction solution was diluted with ethyl acetate, the resultant solution was washed with water and saturated saline and was then dried over sodium sulfate anhydride, and a dried product was concentrated under a reduced pressure. The resultant residue was purified by HPLC. In this manner, the compound of the present invention (300 mg) having the following physical property values was produced.

HPLC retention time (min): 1.31;

MS(ESI, Pos.): 568 $(M+H)^+$;

$^1$H-NMR (DMSO-$d_6$): δ0.67-0.73, 1.21-1.29, 1.33-1.41, 1.43-1.50, 1.51-1.58, 1.71-1.84, 2.03-2.20, 2.63-2.73, 3.10-

3.19, 4.39-4.45, 4.94-5.44, 6.02-6.07, 6.77-6.84, 6.87-6.93, 7.15-7.20, 7.25-7.31, 7.37-7.40, 7.61, 9.42-9.46, 11.98.

Examples 10-1 to 10-3

The same procedures as in Reference Example 25→Example 10 were carried out using, in place of 2-chloro-6-fluoropyridin-4-ol, each of corresponding alcohols. In this manner, the compounds of the present invention having the following physical property values were produced.

Example 10-1: (1R,2S)-2-{3-[({1-[(2S)-2-Butanyl]-5-[2-(2-chloro-3,5-difluorophenoxy)ethyl]-1H-pyrrol-2-yl}carbonyl)amino]-4-(trifluoromethyl)phenyl}cyclopropanecarboxylic acid HPLC retention time (min): 1.37;

MS(ESI, Pos.): 585 $(M+H)^+$;

$^1$H-NMR ($CDCl_3$): δ0.83, 1.42-1.53, 1.61, 1.68-1.80, 1.83-1.97, 2.02-2.16, 2.63-2.77, 3.26-3.33, 4.22-4.30, 4.71-5.33, 6.07-6.14, 6.47-6.62, 6.65-6.70, 7.11-7.16, 7.50-7.56, 7.90-7.97, 8.14-8.20.

Example 10-2: (1R,2S)-2-{3-[({1-[(2S)-2-Butanyl]-5-[2-(2,4-difluorophenoxy)ethyl]-1H-pyrrol-2-yl}carbonyl)amino]-4-(trifluoromethyl)phenyl}cyclopropanecarboxylic acid HPLC retention time (min): 1.32;

MS(ESI, Pos.): 551 $(M+H)^+$;

$^1$H-NMR ($CDCl_3$): δ0.82, 1.41-1.52, 1.59, 1.69-1.77, 1.83-1.95, 1.98-2.25, 2.61-2.76, 3.16-3.29, 4.27, 4.69-5.28, 6.08, 6.67, 6.74-6.98, 7.12, 7.48-7.55, 7.94, 8.18.

Example 10-3: (1R,2S)-2-[3-{[(1-[(2S)-2-Butanyl]-5-{2-[(1-methyl-1H-pyrazol-4-yl)oxy]ethyl}-1H-pyrrol-2-yl)carbonyl]amino}-4-(trifluoromethyl)phenyl]cyclopropanecarboxylic acid HPLC retention time (min): 1.14;

MS(ESI, Pos.): 519 $(M+H)^+$;

$^1$H-NMR ($CDCl_3$): δ 0.82, 1.40-1.51, 1.58, 1.67-1.75, 1.78-1.92, 1.95-2.21, 2.60-2.74, 3.15, 3.84, 4.14, 4.66-5.21, 6.03, 6.66, 7.06-7.16, 7.48-7.56, 7.94, 8.19.

Reference Example 26: Methyl 2,6-dimethyl-4-(2-phenylethoxy)benzoate

Potassium carbonate (5.8 g) and 2-bromoethylbenzene (CAS Number: 103-63-9, 7.7 g) were added to a solution of methyl 4-hydroxy-2,6-dimethylbenzoate (CAS Number: 83194-70-1, 2.5 g) in DMF (10 mL), and the resultant solution was stirred at 80° C. for 15 hours. Subsequently, additional amounts of 2-bromoethylbenzene (1.4 g) and potassium carbonate (1 g) were further added to the solution, and the resultant solution was stirred overnight. The reaction solution was diluted with ethyl acetate and hexane, the resultant solution was washed with water and saturated saline and was then dried over sodium sulfate anhydride, and a dried product was concentrated under a reduced pressure. The resultant residue was purified by silica gel column chromatography (hexane:(ethyl acetate)=9:1→7:3). In this manner, the title compound (3.3 g) having the following physical property values was produced.

HPLC retention time (min): 1.15;

MS(ESI, Pos.): 285 $(M+H)^+$;

$^1$H-NMR ($CDCl_3$): δ 2.29, 3.08, 3.88, 4.16, 6.56, 7.11-7.46.

Reference Example 27: 2,6-Dimethyl-4-(2-phenylethoxy)benzoic acid

A 50% aqueous potassium hydroxide solution (4 mL) was added to a solution of the compound produced in Reference Example 26 (2 g) in NMP (2 mL), and the resultant solution was stirred at 120° C. for 3 hours. The reaction solution was washed with ethyl acetate and hexane, was then made acidic with hydrochloric acid and was then extracted with ethyl acetate. An organic layer was washed with saturated saline and was then dried over sodium sulfate anhydride, and a dried product was concentrated under a reduced pressure. The resultant residue was slurry-washed with hexane. In this manner, the title compound (0.83 g) having the following physical property values was produced.

HPLC retention time (min): 0.98;

MS(ESI, Pos.): 271 $(M+H)^+$.

Example 11: rel-(1R,2S)-2-[3-{[2,6-Dimethyl-4-(2-phenylethoxy)benzoyl]amino}-4-(trifluoromethyl)phenyl]cyclopropanecarboxylic acid Racemic Mixture

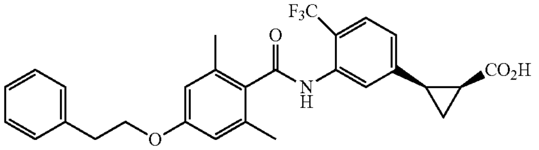

and

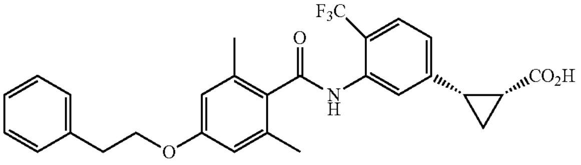

The same procedures as in Reference Example 8→Example 1 were carried out using, in place of the compound produced in Reference Example 3, the compound produced in Reference Example 27. In this manner, the compound of the present invention having the following physical property values was produced.

HPLC retention time (min): 1.15;

MS(ESI, Pos.): 498 $(M+H)^+$;

$^1$H-NMR ($CDCl_3$): δ1.47, 1.66-1.77, 2.11-2.22, 2.35, 2.62-2.74, 3.10, 4.17, 6.60, 7.14, 7.21-7.37, 7.43-7.54, 8.27.

Examples 11-1 to 11-3

The same procedures as in Reference Example 26→Reference Example 27→Reference Example 8→Example 1 were carried out using, in place of methyl 4-hydroxy-2,6-dimethylbenzoate, each of corresponding phenols and also using, in place of the compound produced in Reference Example 4, the compound produced in Reference Example 6. In this manner, the compounds of the present invention having the following physical property values were produced.

Example 11-1: (1R,2S)-2-[3-{[2-Methyl-4-(2-phenylethoxy)benzoyl]amino}-4-(trifluoromethyl)phenyl]cyclopropanecarboxylic acid

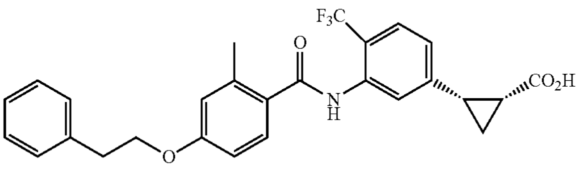 [SMILES: Cc1cc(OCCc2ccccc2)ccc1C(=O)Nc1cc([C@H]2C[C@H]2C(=O)O)ccc1C(F)(F)F]

HPLC retention time (min): 2.28 (condition C);
MS(ESI, Pos.): 484 $(M+H)^+$;
$^1$H-NMR (DMSO-$d_6$): δ0.95-1.02, 1.21-1.29, 1.70-1.79, 2.04-2.13, 2.40, 3.05, 4.24, 6.83-6.89, 7.20-7.27, 7.29-7.43, 7.44-7.52, 9.76.

Example 11-2: (1R,2S)-2-[3-{[2-Chloro-4-(2-phenylethoxy)benzoyl]amino}-4-(trifluoromethyl)phenyl] cyclopropanecarboxylic acid

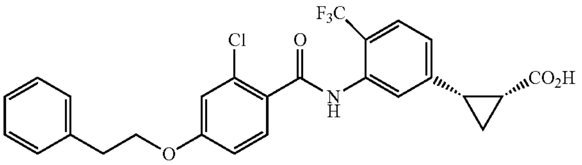

HPLC retention time (min): 2.31 (condition C);
MS(ESI, Pos.): 504 $(M+H)^+$;
$^1$H-NMR (DMSO-$d_6$): δ1.36-1.41, 1.51-1.59, 2.07-2.15, 2.64-2.75, 3.05, 4.29, 7.02-7.07, 7.05, 7.21-7.28, 7.29-7.37, 7.42-7.52, 7.65, 10.06, 12.01.

Example 11-3: (1R,2S)-2-[3-{[4-(2-Phenylethoxy)-2-(trifluoromethyl)benzoyl]amino}-4-(trifluoromethyl)phenyl]cyclopropanecarboxylic acid

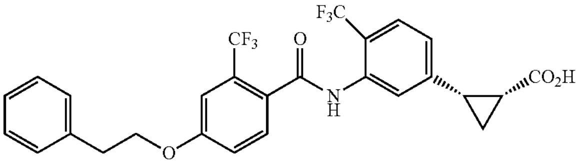 [SMILES: O=C(Nc1cc([C@H]2C[C@H]2C(=O)O)ccc1C(F)(F)F)c1ccc(OCCc2ccccc2)cc1Cl]

HPLC retention time (min): 2.32 (condition C);
MS(ESI, Pos.): 538 $(M+H)^+$;
$^1$H-NMR (DMSO-$d_6$): δ1.30-1.38, 1.45-1.56, 2.02-2.13, 2.56-2.69, 3.08, 4.35, 7.20-7.41, 7.55-7.67, 10.19, 12.01.

Reference Example 28: Methyl 2,6-dimethyl-4-[(1E)-3-phenylprop-1-en-1-yl]benzoate Allylbenzene (CAS Number: 300-57-2, 0.73 g), palladium acetate (CAS Number: 3375-31-3, 46 mg), tri-2-tolylphosphine (CAS Number: 6163-58-2, 0.19 g) and DIPEA (1.6 g) were added to a solution of methyl 4-bromo-2,6-dimethylbenzoate (CAS Number: 90841-46-6, 1 g) in DMF (1 mL), and the resultant solution was stirred at 90° C. for 6 hours and then at 120° C. for 3 hours under a nitrogen atmosphere. A saturated aqueous ammonium chloride solution was added to the reaction solution, and the resultant solution was extracted with ethyl acetate. An organic layer was washed with water and saturated saline, and was then dried over sodium sulfate anhydride, and a dried product was concentrated under a reduced pressure. The resultant residue was purified by silica gel column chromatography (hexane:(ethyl acetate)=7:3→2:3). In this manner, the title compound (1.1 g) having the following physical property values was produced.

HPLC retention time (min): 1.27;
MS(ESI, Pos.): 281 $(M+H)^+$.

Reference Example 29: Methyl 2,6-dimethyl-4-(3-phenylpropyl)benzoate

Palladium hydroxide (45 mg) was added to a solution of the compound produced in Reference Example 28 (180 mg) in ethyl acetate (1 mL), and the resultant solution was stirred at room temperature for 1.5 hours under a hydrogen atmosphere. The reaction solution was filtrated through Celite (trade name), and was then concentrated under a reduced pressure. The resultant residue was purified by silica gel column chromatography (hexane:(ethyl acetate)=100:0→95:5). In this manner, the title compound (160 mg) having the following physical property values was produced.
$^1$H-NMR ($CDCl_3$): δ1.87-1.97, 2.29, 2.57, 2.64, 3.90, 6.85, 7.15-7.23, 7.25-7.32.

Reference Example 30: 2,6-Dimethyl-4-(3-phenylpropyl)benzoic acid

Water (2 mL) and potassium hydroxide (600 mg) were added to a solution of the compound produced in Reference Example 29 (160 mg) in NMP (2 mL), and the resultant solution was stirred at 120° C. for 21 hours. 1N Hydrochloric acid was added to the reaction solution to make the reaction solution acidic, and the solution was extracted with ethyl acetate. An organic layer was washed with saturated saline, was then dried over sodium sulfate anhydride, and a dried product was concentrated under a reduced pressure. In this manner, the title compound (210 mg) having the following physical property values was produced.
$^1$H-NMR ($CDCl_3$): δ1.89-1.97, 2.40, 2.59, 2.65, 6.88, 7.15-7.24, 7.26-7.33.

Reference Example 31: 4-(Acetyloxy)-2,6-dimethylbenzoic acid

Acetic anhydride (2 mL) and pyridine (1.8 mL) were added to a suspension of 4-hydroxy-2,6-dimethylbenzoic acid (CAS Number: 75056-97-2, 3 g) in ethyl acetate (18 mL), and the resultant solution was stirred at room temperature overnight. The reaction solution was diluted with ethyl acetate, was then washed with dilute hydrochloric acid and saturated saline, and was then dried over sodium sulfate anhydride, and a dried product was concentrated under a reduced pressure. The resultant residue was slurry-washed with hexane and ethyl acetate. In this manner, the title compound (2.9 g) having the following physical property values was produced.
$^1$H-NMR ($CDCl_3$): δ 2.30, 2.45, 6.82.

Reference Example 32: Benzyl 4-hydroxy-2,6-dimethylbenzoate

Potassium carbonate (50 g) and benzyl bromide (43 g) were added to a solution of the compound produced in Reference Example 31 (50 g) in DMF (175 mL), and the resultant solution was stirred at room temperature for 3 hours. Methanol (125 mL) and potassium carbonate (50 g) were added to the reaction solution, and the resultant solution was stirred at room temperature for 1 hour. The reaction solution was diluted with 5N hydrochloric acid and water, and was then extracted with ethyl acetate. An organic layer was washed with saturated saline, and was then dried over sodium sulfate anhydride, and a dried product was concentrated under a reduced pressure. The resultant residue was slurry-washed with hexane. In this manner, the title compound (57 g) having the following physical property values was produced.

TLC: Rf 0.60 (hexane:(ethyl acetate)=2:1);

$^1$H-NMR (DMSO-$d_6$): δ2.13, 3.32, 5.27, 6.44, 7.31-7.48, 9.63.

Reference Example 33: Benzyl 4-[2-(2,4-difluorophenyl)ethoxy]-2,6-dimethylbenzoate A solution of 2-(2,4-difluorophenyl)ethanol (CAS Number: 81228-02-6, 1 g), triphenylphosphine (2.5 g) and diethyl azodicarboxylate (also abbreviated as "DEAD", hereinafter) in toluene (2.2M, 4.3 mL) was added to a solution of the compound produced in Reference Example 32 (1.6 g) in THF (10 mL), and the resultant solution was stirred at room temperature for 5 hours. Subsequently, a solution of DEAD in toluene (2.2 M, 2 mL) was further added to the solution, and the resultant solution was stirred at room temperature for 30 minutes. The reaction solution was concentrated under a reduced pressure, and the resultant residue was purified by silica gel column chromatography (hexane:(ethyl acetate)=95:5→75:25). In this manner, the title compound (1.8 g) having the following physical property value was produced.

TLC: Rf 0.79 (hexane:(ethyl acetate)=3:1).

Reference Example 34: 4-[2-(2,4-Difluorophenyl)ethoxy]-2,6-dimethylbenzoic acid

10% Palladium/carbon (0.6 g) was added to a solution of the compound produced in Reference Example 33 (1.8 g) in methanol (20 mL), and the resultant solution was stirred at room temperature for 3.5 hours under a hydrogen atmosphere. The reaction solution was filtrated through Celite (trade name), and the filtrate was concentrated under a reduced pressure. In this manner, the title compound (1.4 g) having the following physical property values was produced.

$^1$H-NMR ($CDCl_3$): δ2.40, 3.08, 4.15, 6.57, 6.76-6.88, 7.17-7.28.

Reference Example 35: Ethyl (1R,2S)-2-{3-[2,6-dimethyl-4-(3-phenylpropyl)benzamide]-4-(trifluoromethyl)phenyl}cyclopropane-1-carboxylate Thionyl chloride (0.01 mL) was added to a suspension of the compound produced in Reference Example 30 (23 mg) in toluene (1 mL), and the resultant solution was stirred at 80° C. for 1 hour. The reaction solution was concentrated under a reduced pressure, and the resultant residue was dissolved in acetonitrile (1 mL). The compound produced in Reference Example 6 (20 mg) was added to the reaction solution, and the resultant solution was stirred at room temperature for 21 hours. The reaction solution was concentrated and was used in the subsequent reaction.

Example 12: (1R,2S)-2-[3-{[2,6-Dimethyl-4-(3-phenylpropyl)benzoyl]amino}-4-(trifluoromethyl)phenyl]cyclopropanecarboxylic acid

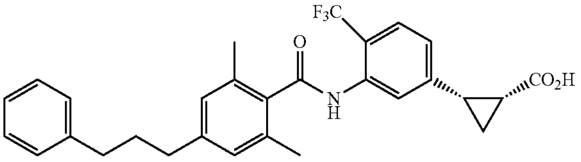 [SMILES: Cc1cc(CCCc2ccccc2)cc(C)c1C(=O)Nc1cc([C@H]2C[C@H]2C(=O)O)ccc1C(F)(F)F]

The same procedure as in Example 1 was carried out using, in place of the compound produced in Reference Example 8, the compound produced in Reference Example 35. In this manner, the compound of the present invention having the following physical property values was produced.

HPLC retention time (min): 1.32;

MS(ESI, Pos.): 496 $(M+H)^+$;

$^1$H-NMR ($CDCl_3$): δ1.46-1.54, 1.67-1.79, 1.89-2.00, 2.16-2.24, 2.36, 2.56-2.74, 6.90, 7.15-7.23, 7.26-7.32, 7.46-7.57, 8.17.

Example 13: (1R,2S)-2-[3-({4-[2-(2,4-Difluorophenyl)ethoxy]-2,6-dimethylbenzoyl}amino)-4-(trifluoromethyl)phenyl]cyclopropanecarboxylic acid The same procedures as in Reference Example 35→Example 12 were carried out using, in place of the compound produced in Reference Example 30, the compound produced in Reference Example 34. In this manner, the compound of the present invention having the following physical property values was produced.

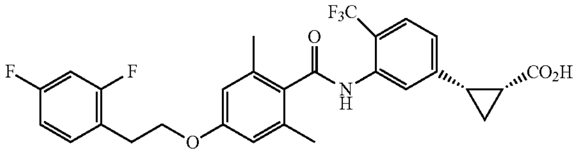 [SMILES: Cc1cc(OCCc2ccc(F)cc2F)cc(C)c1C(=O)Nc1cc([C@H]2C[C@H]2C(=O)O)ccc1C(F)(F)F]

HPLC retention time (min): 1.27;

MS(ESI, Pos.): 534 $(M+H)^+$;

$^1$H-NMR ($CDCl_3$): δ1.46-1.56, 1.75, 2.15-2.27, 2.35, 2.66-2.78, 3.09, 4.15, 6.59, 6.76-6.89, 7.16-7.32, 7.46-7.57, 8.23.

Reference Example 36: Ethyl 2-(2,3-dichloro-4-fluorophenyl)cyclopropane-1-carboxylate Ethyl 2-(4,4,5,5-tetramethyl-1,3,2-dioxaborolan-2-yl)cyclopropanecarboxylate (197 mg), a 2M aqueous potassium phosphate solution (1.2 mL) and [1,1'-bis(diphenylphosphino)ferrocene]palladium(II) dichloride-dichloromethane adduct (134 mg) were added to a solution of 1-bromo-2,3-dichloro-4-fluorobenzene (CAS Number: 1093092-14-8, 200 mg) in 1,4-dioxane (6 mL), and the resultant solution was stirred at 100° C. for 20 hours. The reaction solution was diluted with ethyl acetate, the resultant solution was washed with water and saturated saline and was then dried over sodium sulfate anhydride, and a dried product was concentrated under a reduced pressure. The resultant residue was purified by silica gel column chromatography (hexane:

(ethyl acetate)=97:3→3:1). In this manner, a mixture (150 mg) containing the title compound having the following physical property values was produced.

HPLC retention time (min): 1.12, 1.17;

MS(ESI, Pos.): 277 $(M+H)^+$.

Reference Example 37: Ethyl 2-(2,3-dichloro-4-fluoro-5-nitro phenyl)cyclopropane-1-carboxylate A mixture of concentrated sulfuric acid (0.15 mL) and fuming nitric acid (0.07 mL) was added dropwise to a solution of the mixture produced in Reference Example 36 (150 mg) in concentrated sulfuric acid (0.15 mL) under ice cooling, and the resultant solution was stirred at room temperature for 1 hour. The reaction solution was poured onto ice, and was then extracted with ethyl acetate. An organic layer was washed with saturated saline, and was then dried over sodium sulfate anhydride, and a dried product was concentrated under a reduced pressure. The resultant residue was used as it was without being purified in the subsequent reaction.

Reference Example 38: Ethyl 2-(5-amino-2,3-dichloro-4-fluorophenyl)cyclopropane-1-carboxylate The same procedure as in Reference Example 12 was carried out using, in place of the compound produced in Reference Example 11, the compound produced in Reference Example 37. In this manner, a mixture containing the title compound was produced.

Examples 14-1 to 14-2

The same procedures as in Reference Example 35→Example 1 were carried out using, in place of the compound produced in Reference Example 30, the compound produced in Reference Example 27 and also using, in place of the compound produced in Reference Example 6, the compound produced in Reference Example 38, and the preparative purification with HPLC was then carried out. In this manner, the compounds of the present invention having the following physical property values were produced.

Example 14-1: rel-(1R,2S)-2-(2,3-Dichloro-5-{[2,6-dimethyl-4-(2-phenylethoxy)benzoyl]amino}-4-fluorophenyl)cyclopropanecarboxylic acid Racemic Mixture

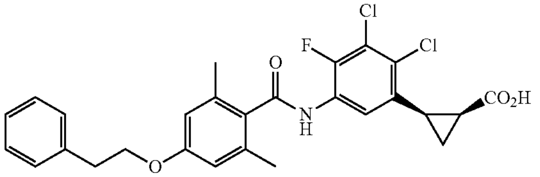

and

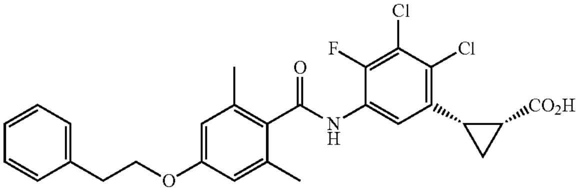

HPLC retention time (min): 1.31;

MS(ESI, Pos.): 516 $(M+H)^+$;

$^1$H-NMR ($CDCl_3$): δ1.53-1.60, 1.69-1.77, 2.23-2.31, 2.34, 2.57-2.66, 3.10, 4.18, 6.60, 7.20-7.37, 7.39-7.43, 8.37.

Example 14-2: rel-(1R,2R)-2-(2,3-Dichloro-5-{[2,6-dimethyl-4-(2-phenylethoxy)benzoyl]amino}-4-fluorophenyl)cyclopropanecarboxylic acid Racemic Mixture

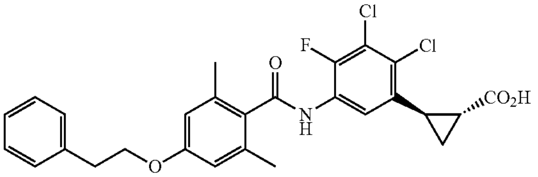

and

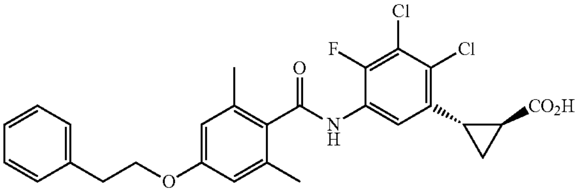

HPLC retention time (min): 1.32;

MS(ESI, Pos.): 516 $(M+H)^+$;

$^1$H-NMR ($CDCl_3$): δ1.50-1.62, 1.68-1.81, 1.85-1.94, 2.33, 2.74-2.87, 3.10, 4.18, 6.61, 7.21-7.38, 7.44, 8.25.

Reference Example 39: Ethyl (1R,2S)-2-{2-chloro-5-[2,6-dimethyl-4-(2-phenylethoxy)benzamide]-4-(trifluoromethyl)phenyl}cyclopropane-1-carboxylate DIPEA (4 mg) and phosphorus oxychloride (3 mg) were added to a solution of the compound produced in Reference Example 27 (8 mg) and the compound produced in Reference Example 7 (6 mg) in acetonitrile (0.5 mL), and the resultant solution was stirred at 50° C. for 2 hours. The reaction solution was concentrated under a reduced pressure, and the resultant residue was purified by silica gel column chromatography (hexane:(ethyl acetate)=95:5→4:1). In this manner, the title compound (6 mg) having the following physical property values was produced.

HPLC retention time (min): 1.25;

MS(ESI, Pos.): 560 $(M+H)^+$.

Example 15: (1R,2S)-2-[2-Chloro-5-{[2,6-dimethyl-4-(2-phenylethoxy)benzoyl]amino}-4-(trifluoromethyl)phenyl]cyclopropanecarboxylic acid

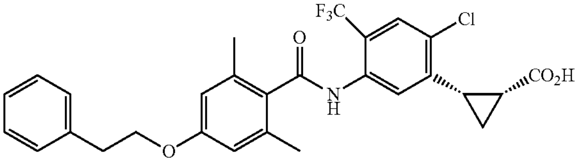 [SMILES: Cc1cc(OCCc2ccccc2)cc(C)c1C(=O)Nc1cc([C@H]2C[C@H]2C(=O)O)c(Cl)cc1C(F)(F)F]

A 5N aqueous sodium hydroxide solution (0.05 mL) was added to a solution of the compound produced in Reference Example 39 (6 mg) in methanol (0.3 mL), and the resultant solution was stirred at room temperature for 17 hours. An additional amount of a 5N aqueous sodium hydroxide solution (0.05 mL) was added to the reaction solution, and the resultant solution was stirred for 3 hours. DME (0.1 mL) was added to the reaction solution, and the resultant solution was stirred for 1 hour. An additional amount of a 5N aqueous sodium hydroxide solution (0.1 mL) was added to the reaction solution, and the resultant solution was stirred for 22 hours. The reaction solution was neutralized with 5N hydrochloric acid, and was then extracted with ethyl acetate. An organic layer was washed with saturated saline, was then dried over sodium sulfate anhydride, and a dried product was concentrated under a reduced pressure. In this manner, a mixture (4 mg) containing the compound of the present invention having the following physical property values was produced.

HPLC retention time (min): 1.12;

MS(ESI, Pos.): 532 $(M+H)^+$;

$^1$H-NMR ($CDCl_3$: δ1.54-1.62, 1.67-1.76, 2.22-2.37, 2.59-2.66, 3.10, 4.16-4.20, 6.59, 7.18-7.37, 7.45, 7.59, 8.30.

Example 16: (1R,2S)-2-(4-Chloro-3-{[2,6-dimethyl-4-(2-phenylethoxy)benzoyl]amino}phenyl)cyclopropanecarboxylic acid

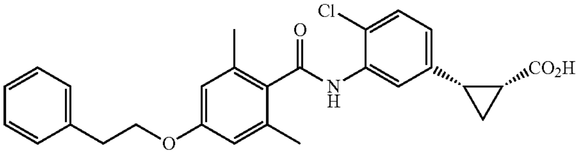 [SMILES: Cc1cc(OCCc2ccccc2)cc(C)c1C(=O)Nc1cc([C@H]2C[C@H]2C(=O)O)ccc1Cl]

The same procedures as in Reference Example 8→Reference Example 14→Reference Example 15→Reference Example 35→Example 1 were carried out using, in place of the compound produced in Reference Example 4, 5-bromo-2-chloroaniline and also using, in place of the compound produced in Reference Example 3, the compound produced in Reference Example 27. In this manner, the compound of the present invention having the following physical property values was produced.

MS(ESI, Pos.): 464 $(M+H)^+$;

$^1$H-NMR ($CDCl_3$): δ1.21-1.27, 1.30-1.36, 1.42-1.49, 2.00-2.07, 2.28-2.32, 2.99-3.05, 4.19, 6.67, 7.06-7.10, 7.19-7.24, 7.28-7.34, 7.36-7.41, 7.49, 9.90, 11.94.

Examples 17-1 to 17-2

The same procedures as in Reference Example 12→Reference Example 35→Reference Example 10→Example 1 were carried out using, in place of the compound produced in Reference Example 11, 3-bromo-4,5-dichloronitrobenzene and also using, in place of the compound produced in Reference Example 30, the compound produced in Reference Example 27 and also using, in place of ethyl 2-(4,4,5,5-tetramethyl-1,3,2-dioxaborolan-2-yl)cyclopropanecarboxylate, a corresponding boronic acid ester, and the preparative purification with HPLC was then carried out. In this manner, the compounds of the present invention having the following physical property values were produced.

Example 17-1: rel-(1R,2S)-2-(2,3-Dichloro-5-{[2,6-dimethyl-4-(2-phenylethoxy)benzoyl]amino}phenyl)cyclopropanecarboxylic acid Racemic Mixture

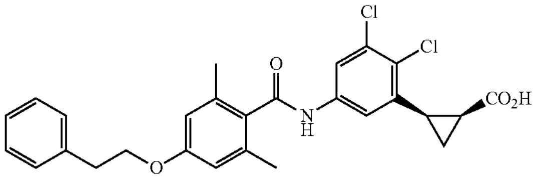

and

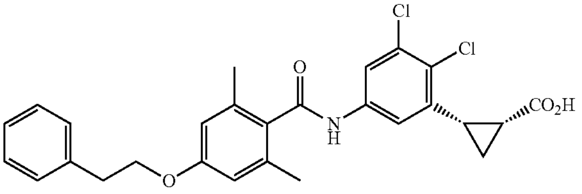

HPLC retention time (min): 1.30;

MS(ESI, Pos.): 498 $(M+H)^+$;

$^1$H-NMR ($CDCl_3$): δ1.44-1.69, 2.32, 2.56-2.70, 3.07-3.12, 4.13-4.19, 6.58, 7.20-7.38, 7.91.

Example 17-2: rel-(1R,2R)-2-(2,3-Dichloro-5-{[2,6-dimethyl-4-(2-phenylethoxy)benzoyl]amino}phenyl)cyclopropanecarboxylic acid Racemic Mixture

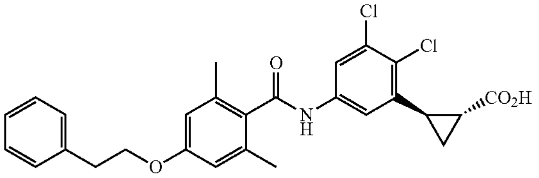

and

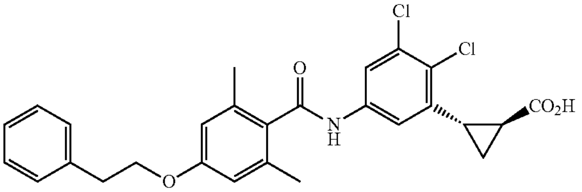

HPLC retention time (min): 1.32;

MS(ESI, Pos.): 498 $(M+H)^+$;

$^1$H-NMR ($CDCl_3$): δ1.39-1.49, 1.67-1.73, 1.81-1.88, 2.32, 2.73-2.90, 3.10, 4.17, 6.59, 7.19-7.42, 7.72.

Reference Example 40: N-[5-Bromo-2-(trifluoromethyl)phenyl]-2,6-dimethyl-4-(2-phenylethoxy)benzamide DIPEA (0.72 g) and phosphorus oxychloride (0.62 g) were added to a solution of the compound produced in Reference Example 27 (1 g) and 5-bromo-2-(trifluoromethyl)aniline (1.1 g) in acetonitrile (10 mL), and the resultant solution was stirred at 50° C. for 12 hours. An additional amount of phosphorus oxychloride (0.12 g) was further added to the reaction solution, and the resultant solution was stirred for 6 hours. The reaction solution was cooled to room temperature, a 1N aqueous sodium hydroxide solution (10 mL) was added to the reaction solution, and the resultant solution was stirred for 10 minutes. Precipitates were filtrated out and were washed with hexane. In this manner, the title compound (1.5 g) having the following physical property values was produced.

HPLC retention time (min): 1.26;

MS(ESI, Pos.): 492 $(M+H)^+$.

Reference Example 41: N-[5-(5,5-Dimethyl-1,3,2-dioxaborinan-2-yl)-2-(trifluoromethyl)phenyl]-2,6-dimethyl-4-(2-phenylethoxy)benzamide Bis(neopentyl glycolato)diboron(459 mg) and potassium acetate (300 mg) were added to a solution of the compound produced in Reference Example 40 (500 mg) in DME (5 mL), the resultant solution was then degassed, [1,1'-bis(diphenylphosphino)ferrocene]palladium(II) dichloride-dichloromethane adduct (83 mg) was then added to the solution, and the resultant solution was stirred at 88° C. for 1.5 hours. The reaction solution was diluted with MTBE, and the resultant solution was filtrated through Celite (trade name). The filtrate was washed with water, and was then dried over sodium sulfate anhydride, and a dried product was concentrated under a reduced pressure. The resultant residue was purified by silica gel column chromatography (hexane:(ethyl acetate)=95:5→1:4). In this manner, the title compound (508 mg) having the following physical property value was produced.

HPLC retention time (min): 1.03.

Reference Example 42: Ethyl (1R,2S)-2-{3-[2,6-dimethyl-4-(2-phenylethoxy)benzamide]-4-(trifluoromethyl)phenyl}cyclopropane-1-carboxylate Ethyl (1S,2S)-2-iodocyclopropanecarboxylate (185 mg) and a 2M aqueous cesium carbonate solution (1.2 mL) were added to a solution of the compound produced in Reference Example 41 (488 mg) in 1,4-dioxane (5.4 mL), the resultant solution was degassed, XPhos Pd G2 (122 mg) was then added to the solution, and the resultant solution was stirred at 100° C. for 1.5 hours. The reaction solution was diluted with MTBE, and the resultant solution was washed with water and was then dried over sodium sulfate anhydride, and a dried product was concentrated under a reduced pressure. The resultant residue was purified by silica gel column chromatography (hexane:(ethyl acetate)=95:5→0:1). In this manner, the title compound (316 mg) having the following physical property values was produced.

HPLC retention time (min): 1.20;

MS(ESI, Pos.): 526 $(M+H)^+$.

Example 18: (1R,2S)-2-[3-{[2,6-Dimethyl-4-(2-phenylethoxy)benzoyl]amino}-4-(trifluoromethyl)phenyl]cyclopropanecarboxylic acid

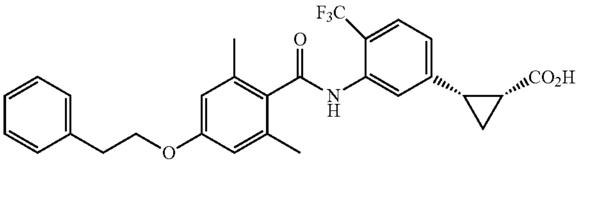 [SMILES: Cc1cc(OCCc2ccccc2)cc(C)c1C(=O)Nc1cc([C@H]2C[C@H]2C(=O)O)ccc1C(F)(F)F]

A 5N aqueous sodium hydroxide solution (1.5 mL) was added to a solution of the compound produced in Reference Example 42 (500 mg) in THF (1.5 mL) and methanol (1.5 mL) under ice cooling, and the resultant solution was stirred at 50° C. for 1 hour. Water was added to the reaction solution, and the resultant solution was washed with hexane. 5N Hydrochloric acid was added to an aqueous layer to neutralize the aqueous layer, and the resultant solution was extracted with MTBE. An organic layer produced was washed with saturated saline, and was then dried over sodium sulfate anhydride, and a dried product was concentrated under a reduced pressure. The resultant residue was purified by silica gel column chromatography (hexane:(ethyl acetate)=95:5→1:1). In this manner, the compound of the present invention (395 mg) having the following physical property values was produced.

HPLC retention time (min): 1.06;

MS(ESI, Pos.): 498 $(M+H)^+$;

$^1$H-NMR ($CDCl_3$): δ1.39-1.51, 1.64-1.75, 2.09-2.21, 2.34, 2.62-2.73, 3.10, 4.15-4.21, 6.59, 7.11-7.18, 7.22-7.37, 7.45-7.53, 8.24.

Example 19: (1S,2R)-2-[3-{[2,6-Dimethyl-4-(2-phenylethoxy)benzoyl]amino}-4-(trifluoromethyl)phenyl]cyclopropanecarboxylic acid

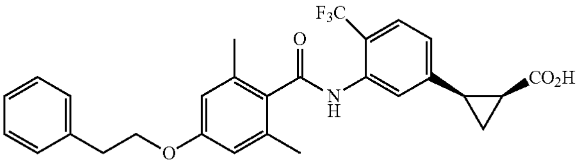 [SMILES: Cc1cc(OCCc2ccccc2)cc(C)c1C(=O)Nc1cc([C@@H]2C[C@@H]2C(=O)O)ccc1C(F)(F)F]

The same procedures as in Reference Example 42→Example 18 were carried out using, in place of ethyl (1S,2S)-2-iodocyclopropanecarboxylate, a corresponding iodine compound. In this manner, the compound of the present invention having the following physical property values was produced.

HPLC retention time (min): 1.08;

MS(ESI, Pos.): 498 $(M+H)^+$;

$^1$H-NMR ($CDCl_3$): δ1.43-1.53, 1.68-1.77, 2.10-2.21, 2.34, 2.63-2.76, 3.10, 4.17, 6.59, 7.17, 7.22-7.36, 7.47-7.58, 8.22.

Reference Example 43: Ethyl (1R,2S)-2-{3-[4-(acetyloxy)-2,6-dimethylbenzamide]-4-(trifluoromethyl)phenyl}cyclopropane-1-carboxylate Thionyl chloride (0.4 mL) and DMF (42 mg) were added to a suspension of the compound produced in Reference Example 31 (914 mg) in toluene (5 mL), and the resultant solution was stirred at 75° C. for 2 hours. The reaction solution was concentrated under a reduced pressure, a solution of the compound produced in Reference Example 6 (1 g) in acetonitrile was added to the resultant residue, and the resultant solution was stirred at 55° C. for 2 hours. The reaction solution was diluted with hexane and MTBE, was then washed with a 1N aqueous sodium hydroxide solution, 5N hydrochloric acid and saturated saline, and was then dried over sodium sulfate anhydride, and a dried product was concentrated under a reduced pressure. The resultant residue was purified by silica gel column chromatography (hexane:(ethyl acetate)=9:1→1:1). In this manner, the title compound (1.4 g) having the following physical property value was produced.

HPLC retention time (min): 1.03;

MS(ESI, Pos.): 464 $(M+H)^+$.

Reference Example 44: Ethyl (1R,2S)-2-[3-(4-hydroxy-2,6-dimethylbenzamide)-4-(trifluoromethyl)phenyl]cyclopropane-1-carboxylate Potassium carbonate (1.3 g) was added to a solution of the compound produced in Reference Example 43 (1.4 g) in ethanol (40 mL), and the resultant solution was stirred at room temperature for 22 hours. The reaction solution was filtrated through Celite (trade name), and the filtrate was concentrated under a reduced pressure. The resultant residue was purified by silica gel column chromatography (hexane:(ethyl acetate)=9:1→0:1). In this manner, the title compound (1.1 g) having the following physical property values was produced.

HPLC retention time (min): 0.94;

MS(ESI, Pos.): 422 $(M+H)^+$.

Example 20: (1R,2S)-2-[3-({2,6-Dimethyl-4-[2-(1-methyl-1H-pyrazol-4-yl)ethoxy]benzoyl}amino)-4-(trifluoromethyl)phenyl]cyclopropanecarboxylic acid

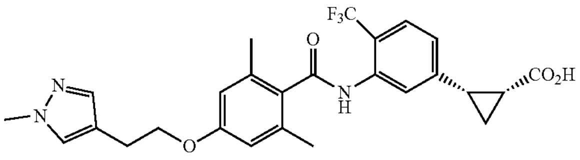 [SMILES: Cc1cc(OCCc2cnn(C)c2)cc(C)c1C(=O)Nc1cc([C@H]2C[C@H]2C(=O)O)ccc1C(F)(F)F]

2-(1-Methyl-1H-pyrazol-4-yl)ethanol (CAS Number: 176661-75-9, 12 mg) and CMBP (17 mg) were added to a solution of the compound produced in Reference Example 44 (20 mg) in toluene (0.5 mL), and the resultant solution was stirred at 80° C. for 2 hours. An additional amount of CMBP (17 mg) was further added to the reaction solution, and the resultant solution was stirred for 1.5 hours. A residue produced by condensing the reaction solution was dissolved in methanol (0.3 mL), a 5N aqueous sodium hydroxide solution (0.05 mL) was added to the solution, and the resultant solution was stirred at 50° C. for 14 hours. The reaction solution was neutralized with 5N hydrochloric acid and was then purified by HPLC. In this manner, the compound of the present invention (4 mg) having the following physical property values was produced.

HPLC retention time (min): 1.05;

MS(ESI, Pos.): 502 $(M+H)^+$;

$^1$H-NMR ($CDCl_3$): δ1.45-1.53, 1.71-1.78, 2.15-2.23, 2.36, 2.64-2.76, 2.93, 3.87, 4.04-4.11, 6.61, 7.18, 7.27, 7.40, 7.48, 7.53, 8.29.

Examples 20-1 to 20-23

The same procedure as in Example 20 was carried out using, in place of 2-(1-methyl-1H-pyrazol-4-yl)ethanol, each of corresponding alcohols. In this manner, the compounds of the present invention having the following physical property values were produced.

Example 20-1: (1R,2S)-2-[3-{[4-(2-Cyclopropylethoxy)-2,6-dimethylbenzoyl]amino}-4-(trifluoromethyl)phenyl]cyclopropanecarboxylic acid

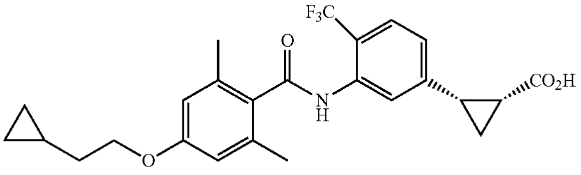 [SMILES: Cc1cc(OCCC2CC2)cc(C)c1C(=O)Nc1cc([C@H]2C[C@H]2C(=O)O)ccc1C(F)(F)F]

HPLC retention time (min): 1.24;

MS(ESI, Pos.): 462 $(M+H)^+$;

$^1$H-NMR ($CDCl_3$): δ0.09-0.17, 0.47-0.53, 0.77-0.91, 1.44-1.55, 1.65-1.78, 2.20, 2.36, 2.63-2.75, 4.04, 6.62, 7.20, 7.46-7.58, 8.18.

Example 20-2: (1R,2S)-2-{3-[(2,6-Dimethyl-4-propoxybenzoyl)amino]-4-(trifluoromethyl)phenyl}cyclopropanecarboxylic acid HPLC retention time (min): 1.19;

MS(ESI, Pos.): 436 $(M+H)^+$;

$^1$H-NMR ($CDCl_3$): δ1.04, 1.45-1.53, 1.66-1.87, 2.11-2.26, 2.35, 2.62-2.74, 3.93, 6.60, 7.20, 7.44-7.58, 8.17.

Example 20-3: (1R,2S)-2-[3-f{[4-(Hexyloxy)-2,6-dimethylbenzoyl]amino}-4-(trifluoromethyl)phenyl]cyclopropanecarboxylic acid HPLC retention time (min): 1.14;

MS(ESI, Pos.): 478 $(M+H)^+$;

$^1$H-NMR ($CDCl_3$): δ0.86-0.98, 1.04-1.16, 1.03-1.55, 1.72-1.83, 1.84-1.95, 2.19-2.31, 3.95, 6.53, 7.07-7.14, 7.31-7.39, 7.46-7.57, 7.67-7.76.

Example 20-4: (1R,2S)-2-[3-{[4-(Benzyloxy)-2,6-dimethylbenzoyl]amino}-4-(trifluoromethyl)phenyl]cyclopropanecarboxylic acid HPLC retention time (min): 1.22;

MS(ESI, Pos.): 484 $(M+H)^+$;

$^1$H-NMR ($CDCl_3$): δ1.43-1.55, 1.73, 2.14-2.27, 2.36, 2.65-2.76, 5.07, 6.69, 7.20, 7.31-7.46, 7.49-7.59, 8.17.

Example 20-5: (1R,2S)-2-[3-{[4-(2-Methoxyethoxy)-2,6-dimethylbenzoyl]amino}-4-(trifluoromethyl)phenyl]cyclopropanecarboxylic acid HPLC retention time (min): 1.07;

MS(ESI, Pos.): 452 $(M+H)^+$;

$^1$H-NMR ($DMSO-d_6$): δ1.35-1.43, 1.49-1.59, 2.05-2.15, 2.30, 2.63-2.79, 3.30, 3.60-3.68, 4.08, 6.67, 7.27-7.34, 7.44, 7.58-7.68, 9.95, 12.03.

Example 20-6: (1R,2S)-2-[3-({2,6-Dimethyl-4-[2-(tetrahydro-2H-pyran-2-yl)ethoxy]benzoyl}amino)-4-(trifluoromethyl)phenyl]cyclopropanecarboxylic acid HPLC retention time (min): 1.21;

MS(ESI, Pos.): 506 $(M+H)^+$;

$^1$H-NMR ($CDCl_3$): δ1.22-1.76, 1.80-1.96, 2.15-2.24, 2.35, 2.63-2.77, 3.35-3.60, 3.91-4.18, 6.62, 7.19, 7.46-7.57, 8.19.

Example 20-7: (1R,2S)-2-[3-({4-[2-(2-Furyl)ethoxy]-2,6-dimethylbenzoyl}amino)-4-(trifluoromethyl)phenyl]cyclopropanecarboxylic acid HPLC retention time (min): 1.20;

MS(ESI, Pos.): 488 $(M+H)^+$;

$^1$H-NMR ($CDCl_3$): δ1.45-1.55, 1.69-1.76, 2.16-2.23, 2.35, 2.62-2.77, 3.13, 4.22, 6.15, 6.32, 6.61, 7.20, 7.29-7.40, 7.44-7.59, 8.18.

Example 20-8: (1R,2S)-2-[3-({4-[2-(2-Chlorophenyl)ethoxy]-2,6-dimethylbenzoyl}amino)-4-(trifluoromethyl)phenyl]cyclopropanecarboxylic acid HPLC retention time (min): 1.30;

MS(ESI, Pos.): 532 $(M+H)^+$; $^1$H-NMR ($CDCl_3$): δ1.43-1.53, 1.67-1.78, 2.18, 2.34, 2.61-2.74, 3.24, 4.20, 6.61, 7.14-7.26, 7.32-7.42, 7.44-7.50, 7.50-7.56, 8.22.

Example 20-9: (1R,2S)-2-[3-({4-[2-(3-Chlorophenyl)ethoxy]-2,6-dimethylbenzoyl}amino)-4-(trifluoromethyl)phenyl]cyclopropanecarboxylic acid HPLC retention time (min): 1.30;

MS(ESI, Pos.): 532 $(M+H)^+$;

$^1$H-NMR ($CDCl_3$): δ1.44-1.55, 1.67-1.77, 2.16-2.24, 2.35, 2.65-2.74, 3.07, 4.17, 6.59, 7.14-7.31, 7.45-7.55, 8.20.

Example 20-10: (1R,2S)-2-[3-({4-[2-(1H-Imidazol-1-yl)ethoxy]-2,6-dimethylbenzoyl}amino)-4-(trifluoromethyl)phenyl]cyclopropanecarboxylic acid HPLC retention time (min): 0.84;

MS(ESI, Pos.): 488 $(M+H)^+$; $^1$H-NMR ($CDCl_3$): δ1.46-1.55, 1.69-1.78, 2.17-2.27, 2.33, 2.65-2.74, 4.28-4.34, 4.52-4.59, 6.55, 7.19-7.30, 7.37, 7.48, 7.53-7.57, 8.18, 8.96.

Example 20-11: (1R,2S)-2-[3-({4-[2-(2,6-Difluorophenyl)ethoxy]-2,6-dimethylbenzoyl}amino)-4-(trifluoromethyl)phenyl]cyclopropanecarboxylic acid HPLC retention time (min): 1.26;

MS(ESI, Pos.): 534 $(M+H)^+$;

$^1$H-NMR ($CDCl_3$): δ1.45-1.56, 1.67-1.79, 2.15-2.26, 2.34, 2.65-2.76, 3.18, 4.16, 6.60, 6.83-6.94, 7.14-7.25, 7.45-7.57, 8.19.

Example 20-12: (1R,2S)-2-[3-({4-[2-(3,5-Difluorophenyl)ethoxy]-2,6-dimethylbenzoyl}amino)-4-(trifluoromethyl)phenyl]cyclopropanecarboxylic acid HPLC retention time (min): 1.27;

MS(ESI, Pos.): 534 $(M+H)^+$;

$^1$H-NMR ($CDCl_3$): δ1.57-1.58, 1.70-1.79, 2.15-2.28, 2.36, 2.68-2.78, 3.07, 4.17, 6.60, 6.65-6.73, 6.78-6.88, 7.17-7.23, 7.50, 7.55, 8.23.

Example 20-13: (1R,2S)-2-[3-{[4-(1H-Indazol-5-ylmethoxy)-2,6-dimethylbenzoyl]amino}-4-(trifluoromethyl)phenyl]cyclopropanecarboxylic acid HPLC retention time (min): 1.09;

MS(ESI, Pos.): 524 $(M+H)^+$;

$^1$H-NMR (DMSO-$d_6$): δ1.35-1.47, 1.51-1.60, 2.32, 2.65-2.74, 5.21, 6.79, 7.31-7.36, 7.40-7.48, 7.54-7.60, 7.65, 7.84, 8.09, 9.95, 12.62-13.37.

Example 20-14: (1R,2S)-2-[3-{[2,6-Dimethyl-4-(1,2,3,4-tetrahydro-1-naphthalenylmethoxy)benzoyl]amino}-4-(trifluoromethyl)phenyl]cyclopropanecarboxylic acid HPLC retention time (min): 1.33;

MS(ESI, Pos.): 538 $(M+H)^+$;

$^1$H-NMR (DMSO-$d_6$): δ1.34-1.46, 1.49-1.58, 1.62-2.02, 2.04-2.20, 2.28-2.35, 2.65-2.80, 3.16-3.28, 3.99-4.10, 4.15-4.22, 6.73, 7.07-7.19, 7.29-7.37, 7.46, 7.61-7.70, 9.94, 12.1.

Example 20-15: (1R,2S)-2-[3-({2,6-Dimethyl-4-[2-(3-pyridinyl)ethoxy]benzoyl}amino)-4-(trifluoromethyl)phenyl]cyclopropanecarboxylic acid HPLC retention time (min): 0.89;

MS(ESI, Pos.)$_{499}$:$(M+H)^+$;

$^1$H-NMR (DMSO-$d_6$): δ1.35-1.46, 1.50-1.58, 2.04-2.20, 2.31, 2.62-2.77, 3.21, 4.29, 6.68, 7.31-7.39, 7.45, 7.66, 7.81, 8.27-8.30, 8.70, 8.80 9.93, 11.48-12.44.

Example 20-16: (1R,2S)-2-[3-({2,6-Dimethyl-4-[2-(4-pyridinyl)ethoxy]benzoyl}amino)-4-(trifluoromethyl)phenyl]cyclopropanecarboxylic acid HPLC retention time (min): 0.88;

MS(ESI, Pos.): 499 $(M+H)^+$;

$^1$H-NMR (DMSO-$d_6$): δ1.38-1.43, 1.50-1.59, 2.07-2.18, 2.31, 2.66-2.75, 3.16-3.19, 4.31, 6.68, 7.34, 7.45, 7.60, 7.66, 8.63, 9.94, 11.70-12.35.

Example 20-17: (1R,2S)-2-[3-({2,6-Dimethyl-4-[2-(2-pyridinyl)ethoxy]benzoyl}amino)-4-(trifluoromethyl)phenyl]cyclopropanecarboxylic acid HPLC retention time (min): 0.90;

MS(ESI, Pos.): 499 $(M+H)^+$;

$^1$H-NMR (DMSO-$d_6$): δ1.34-1.44, 1.49-1.59, 2.05-2.17, 2.31, 2.66-2.79, 3.36, 4.40, 6.67, 7.30-7.38, 7.45, 7.66, 7.73-7.85, 8.09-8.36, 8.73, 9.93, 12.03.

Example 20-18: (1R,2S)-2-[3-({4-[2-(2-Chloro-1H-imidazol-1-yl)ethoxy]-2,6-dimethylbenzoyl}amino)-4-(trifluoromethyl)phenyl]cyclopropanecarboxylic acid HPLC retention time (min): 1.05;

MS(ESI, Pos.): 522 $(M+H)^+$;

$^1$H-NMR (DMSO-$d_6$): δ1.33-1.47, 1.50-1.59, 2.05-2.18, 2.31, 2.67-2.75, 4.25-4.31, 4.33-4.39, 6.66, 6.91-6.96, 7.30-7.37, 7.38-7.41, 7.44-7.48, 7.65, 9.95.

Example 20-19: (1R,2S)-2-[3-({4-[2-(2-Fluorophenyl)ethoxy]-2,6-dimethylbenzoyl}amino)-4-(trifluoromethyl)phenyl]cyclopropanecarboxylic acid HPLC retention time (min): 1.25;

MS(ESI, Pos.): 516 $(M+H)^+$;

$^1$H-NMR (DMSO-$d_6$): δ1.33-1.45, 1.48-1.59, 2.10-2.16, 2.31, 2.63-2.77, 3.08, 4.21, 6.68, 7.12-7.23, 7.25-7.38, 7.39-7.49, 7.65, 9.95, 12.10.

Example 20-20: (1R,2S)-2-[3-({4-[2-(3-Fluorophenyl)ethoxy]-2,6-dimethylbenzoyl}amino)-4-(trifluoromethyl)phenyl]cyclopropanecarboxylic acid HPLC retention time (min): 1.24;

MS(ESI, Pos.): 516 $(M+H)^+$;

$^1$H-NMR (DMSO-$d_6$): δ1.34-1.46, 1.48-1.60, 2.05-2.19, 2.31, 2.64-2.78, 3.07, 4.22, 6.69, 7.02-7.10, 7.15-7.24, 7.30-7.40, 7.45, 7.65, 9.95, 12.10.

Example 20-21: (1R,2S)-2-[3-({4-[2-(4-Fluorophenyl)ethoxy]-2,6-dimethylbenzoyl}amino)-4-(trifluoromethyl)phenyl]cyclopropanecarboxylic acid HPLC retention time (min): 1.23;

MS(ESI, Pos.): 516 $(M+H)^+$;

$^1$H-NMR (DMSO-$d_6$): δ1.38-1.45, 1.50-1.61, 2.08-2.17, 2.31, 2.64-2.73, 3.03, 4.19, 6.68, 7.11-7.19, 7.29-7.42, 7.45, 7.65, 9.94, 12.06.

Example 20-22: (1R,2S)-2-[3-{[2,6-Dimethyl-4-(3,3,3-trifluoropropoxy)benzoyl]amino}-4-(trifluoromethyl)phenyl]cyclopropanecarboxylic acid HPLC retention time (min): 1.17;

MS(ESI, Pos.): 490 $(M+H)^+$;

$^1$H-NMR (DMSO-$d_6$): δ1.38-1.46, 1.50-1.58, 2.07-2.17, 2.33, 2.68-2.74, 2.74-2.85, 4.22, 6.72, 7.34, 7.46, 7.66, 9.98, 12.02.

Example 20-23: (1R,2S)-2-[3-f{[2,6-Dimethyl-4-(3,3,3-trifluoro-2-methylpropoxy)benzoyl]amino}-4-(trifluoromethyl)phenyl]cyclopropanecarboxylic acid HPLC retention time (min): 1.20;

MS(ESI, Pos.): 504 $(M+H)^+$;

$^1$H-NMR (DMSO-$d_6$): δ1.21, 1.36-1.48, 1.50-1.62, 2.07-2.18, 2.33, 2.64-2.74, 2.82-3.02, 4.03-4.19, 6.72, 7.30-7.37, 7.46, 7.66, 9.97, 11.99.

Reference Example 45: Ethyl (1R,2S)-2-[3-{4-[(6-chloropyrazin-2-yl)oxy]-2,6-dimethylbenzamide}-4-(trifluoromethyl)phenyl]cyclopropane-1-carboxylate 2,6-Dichloropyrazine (CAS Number: 4774-14-5, 21 mg) and potassium carbonate (25 mg) were added to a solution of the compound produced in Reference Example 44 (50 mg) in DMF (1 mL), and the resultant solution was stirred at 50° C. for 2 hours. The reaction solution was diluted with MTBE, the resultant solution was washed with water and saturated saline and was then dried over sodium sulfate anhydride, and a dried product was concentrated under a reduced pressure. The resultant residue was used in the subsequent reaction without being purified.

Example 21: (1R,2S)-2-[3-({4-[(6-Chloro-2-pyrazinyl)oxy]-2,6-dimethylbenzoyl}amino)-4-(trifluoromethyl)phenyl]cyclopropanecarboxylic acid

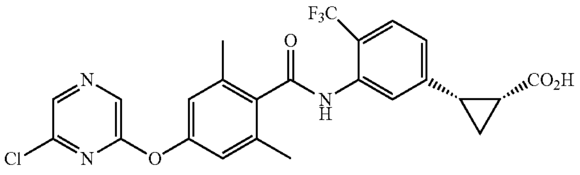 [SMILES: Cc1cc(Oc2cncc(Cl)n2)cc(C)c1C(=O)Nc1cc([C@H]2C[C@H]2C(=O)O)ccc1C(F)(F)F]

Water (0.2 mL) and concentrated sulfuric acid (0.05 mL) were added to a solution of a crude product produced in Reference Example 45 in 1,4-dioxane (0.2 mL), and the resultant solution was stirred at 100° C. for 15 hours. The reaction solution was diluted with ethyl acetate, was then washed with water, and was then dried over sodium sulfate anhydride, and a dried product was concentrated under a reduced pressure. The resultant residue was purified by HPLC. In this manner, the compound of the present invention (30 mg) having the following physical property values was produced.

HPLC retention time (min): 1.16;

MS(ESI, Pos.): 506 $(M+H)^+$;

$^1$H-NMR ($CDCl_3$): δ1.46-1.55, 1.70-1.77, 2.16-2.24, 2.41, 2.66-2.76, 6.89, 7.21, 7.53-7.59, 8.20, 8.31, 8.32.

Examples 21-1 to 21-2

The same procedures as in Reference Example 45→Example 21 were carried out using, in place of 2,6-dichloropyrazine, each of corresponding chloro compounds. In this manner, the compounds of the present invention having the following physical property values were produced.

Example 21-1: (1R,2S)-2-{3-[(2,6-Dimethyl-4-{[6-(trifluoromethyl)-2-pyridinyl]oxy}benzoyl)amino]-4-(trifluoromethyl)phenyl}cyclopropanecarboxylic acid

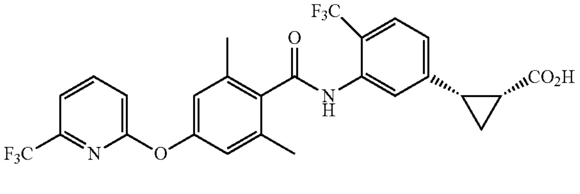 [SMILES: Cc1cc(Oc2cccc(C(F)(F)F)n2)cc(C)c1C(=O)Nc1cc([C@H]2C[C@H]2C(=O)O)ccc1C(F)(F)F]

HPLC retention time (min): 1.21;

MS(ESI, Pos.): 539 $(M+H)^+$;

$^1$H-NMR (DMSO-$d_6$): δ1.37-1.47, 1.52-1.61, 2.09-2.19, 2.37, 2.66-2.80, 6.98, 7.27-7.43, 7.48, 7.68, 8.02-8.27, 10.22, 12.05.

Example 21-2: (1R,2S)-2-[3-{[2,6-Dimethyl-4-(pyrazolo[1,5-a]pyrimidin-5-yloxy)benzoyl]amino}-4-(trifluoromethyl)phenyl]cyclopropanecarboxylic acid

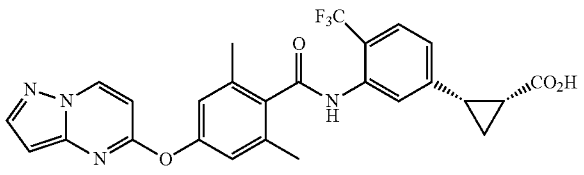 [SMILES: Cc1cc(Oc2ccn3nccc3n2)cc(C)c1C(=O)Nc1cc([C@H]2C[C@H]2C(=O)O)ccc1C(F)(F)F]

HPLC retention time (min): 1.06;

MS(ESI, Pos.): 511 $(M+H)^+$;

$^1$H-NMR (DMSO-$d_6$): δ1.39-1.46, 1.52-1.59, 2.10-2.17, 2.39, 2.69-2.81, 6.38, 6.83, 7.03, 7.36, 7.49, 7.68, 8.08, 9.08, 10.27, 12.16.

Reference Example 46: Ethyl (1R,2S)-2-[3-{2,6-dimethyl-4-[(trifluoromethanesulfonyl)oxy]benzamide}-4-(trifluoromethyl)phenyl]cyclopropane-1-carboxylate 1,1,1-Trifluoro-N-(trifluoromethylsulfonyl)methanesulfonamide (CAS Number: 37595-74-7, 127 mg) and triethylamine (72 mg) were added to a solution of the compound produced in Reference Example 44 (100 mg) in THE (3 mL), and the resultant solution was stirred at room temperature for 88 hours. The reaction solution was diluted with ethyl acetate, was then washed with water, and was then dried over sodium sulfate anhydride, and a dried product was concentrated under a reduced pressure. The resultant residue was purified by silica gel column chromatography (hexane:(ethyl acetate)=97:3→1:1). In this manner, the title compound (120 mg) having the following physical property values was produced.

HPLC retention time (min): 1.14;

MS(ESI, Pos.): 554 $(M+H)^+$.

Reference Example 47: Ethyl (1R,2S)-2-{3-[4-(6-fluoropyridin-3-yl)-2,6-dimethylbenzamide]-4-(trifluoromethyl)phenyl}cyclopropane-1-carboxylate 2-Fluoro-5-(4,4,5,5-tetramethyl-1,3,2-dioxaborolan-2-yl)pyridine (CAS Number: 444120-95-0, 127 mg), a 2M aqueous cesium carbonate solution (0.08 mL) and XPhos Pd G2 (8 mg) were added to a solution of the compound produced in Reference Example 46 (30 mg) in 1,4-dioxane (3 mL), and the resultant solution was stirred at 100° C. for 2.5 hours. The reaction solution was diluted with ethyl acetate, was then washed with water, and was then dried over sodium sulfate anhydride, and a dried product was concentrated under a reduced pressure. The resultant residue was purified by silica gel column chromatography (hexane:(ethyl acetate)=9:1→1:1). In this manner, the title compound having the following physical property values was produced.

HPLC retention time (min): 1.07;

MS(ESI, Pos.): 501 $(M+H)^+$.

Example 22: (1R,2S)-2-[3-{[4-(6-Fluoro-3-pyridinyl)-2,6-dimethylbenzoyl]amino}-4-(trifluoromethyl)phenyl]cyclopropanecarboxylic acid

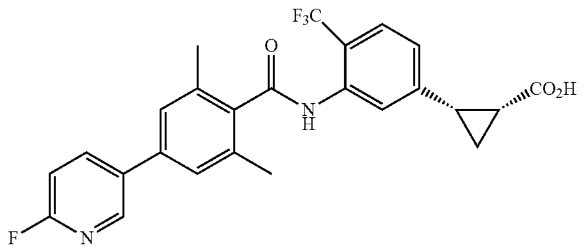 [SMILES: Cc1cc(-c2ccc(F)nc2)cc(C)c1C(=O)Nc1cc([C@H]2C[C@H]2C(=O)O)ccc1C(F)(F)F]

A 5N aqueous sodium hydroxide solution (0.3 mL) was added to a solution of the compound produced in Reference Example 47 in methanol (1 mL), and the resultant solution was stirred at 50° C. for 17 hours. The reaction solution was neutralized with 5N hydrochloric acid, and was then extracted with ethyl acetate. An organic layer was concentrated under a reduced pressure, and was then purified by HPLC. In this manner, the compound of the present invention (12 mg) having the following physical property values was produced.

HPLC retention time (min): 1.13;

MS(ESI, Pos.): 473 $(M+H)^+$;

$^1$H-NMR ($CDCl_3$): δ1.46-1.58, 1.71-1.80, 2.16-2.28, 2.47, 2.66-2.78, 7.01-7.09, 7.18-7.27, 7.52-7.61, 7.94-8.03, 8.21, 8.43.

Reference Example 48: 2-{4-[(4-Methoxybenzyl)oxy]phenyl}ethanol

Potassium carbonate (3 g) and 4-methoxybenzyl chloride (CAS Number: 824-94-2, 2.5 g) were added to a solution of 4-(2-hydroxyethyl)phenol (CAS Number: 501-94-0, 2 g) in DMF (10 mL), and the resultant solution was stirred at 50° C. for 14 hours. Water was added to the reaction solution, and precipitates were filtrated out. The resultant crude product was dissolved in ethyl acetate, and the resultant solution was washed with saturated saline, was then dried over sodium sulfate anhydride, and a dried product was concentrated under a reduced pressure. In this manner, the title compound (3.4 g) having the following physical property values was produced.

$^1$H-NMR ($CDCl_3$): δ2.81, 3.75-3.90, 4.97, 6.85-6.98, 7.11-7.19, 7.33-7.38.

Reference Example 49: (1R,2S)-2-{3-[4-(2-{4-[(4-Methoxyphenyl)methoxy]phenyl}ethoxy)-2,6-dimethylbenzamide]-4-(trifluoromethyl)phenyl}cyclopropane-1-carboxylic acid The compound produced in Reference Example 48 (25 mg) and CMBP (17 mg) were added to a solution of the compound produced in Reference Example 44 (20 mg) in toluene (0.5 mL), and the resultant solution was stirred at 80° C. for 27 hours. The reaction solution was concentrated under a reduced pressure, methanol (0.3 mL), THE (0.3 mL) and a 5N aqueous sodium hydroxide solution (0.05 mL) were added to a residue, and the resultant solution was stirred at 50° C. for 2 hours and further stirred at room temperature for 21 hours. The reaction solution was neutralized with 5N hydrochloric acid, and was then extracted with ethyl acetate. An organic layer was concentrated under a reduced pressure, and the resultant residue was used in the subsequent reaction without being purified.

Example 23: (1R,2S)-2-[3-({4-[2-(4-Hydroxyphenyl)ethoxy]-2,6-dimethylbenzoyl}amino)-4-(trifluoromethyl)phenyl]cyclopropanecarboxylic acid

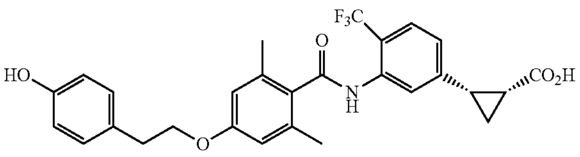 [SMILES: Cc1cc(OCCc2ccc(O)cc2)cc(C)c1C(=O)Nc1cc([C@H]2C[C@H]2C(=O)O)ccc1C(F)(F)F]

A solution of the crude product produced in Reference Example 49 in acetic acid (1 mL) was stirred while heating at 150° C. for 15 minutes using a microwave reaction device. The reaction solution was concentrated under a reduced pressure, and the resultant residue was purified by silica gel column chromatography (Fuji Silysia Chemical Ltd., Chromatorex DIOL60, hexane:(ethyl acetate)=9:1→0:1). In this manner, the compound of the present invention (18 mg) having the following physical property values was produced.

HPLC retention time (min): 1.13;

MS(ESI, Pos.): 514 (M+H);

$^1$H-NMR ($CDCl_3$): δ1.43-1.51, 1.64-1.75, 2.17, 2.34, 2.63-2.72, 3.02, 4.13, 6.59, 6.75-6.82, 7.08-7.20, 7.45-7.49, 7.50-7.55, 8.16-8.24.

Reference Example 50: Ethyl (2E)-3-{3-[2,6-dimethyl-4-(2-phenylethoxy)benzamide]-4-(trifluoromethyl)phenyl}prop-2-enoate Ethyl acrylate (18 mg), DIPEA (24 mg) and tetrakis (triphenylphosphine)palladium(0) (CAS Number: 14221-01-3, 14 mg) were added to a solution of the compound produced in Reference Example 40 (30 mg) in 1,4-dioxane (1 mL), and the resultant solution was stirred at 100° C. overnight. The reaction solution was purified by silica gel column chromatography (hexane:(ethyl acetate)=9:1→0:1), to produce the title compound, and the title compound was used in the subsequent reaction.

Reference Example 51: (2E)-3-{3-[2,6-Dimethyl-4-(2-phenylethoxy)benzamide]-4-(trifluoromethyl) phenyl}prop-2-enoic acid A 2N aqueous sodium hydroxide solution (0.5 mL) was added to a solution of the compound produced in Reference Example 50 in THF/methanol (1 mL), and the resultant solution was stirred at room temperature for 2 hours. The reaction solution was neutralized with 2N hydrochloric acid, and was then extracted with ethyl acetate. An organic layer was washed with saturated saline, and was then dried over sodium sulfate anhydride, and a dried product was concentrated under a reduced pressure. The resultant residue was used as it was in the subsequent reaction without being purified.

Example 24:3-[3-f{[2,6-Dimethyl-4-(2-phenylethoxy)benzoyl]amino}-4-(trifluoromethyl)phenyl] propanoic acid

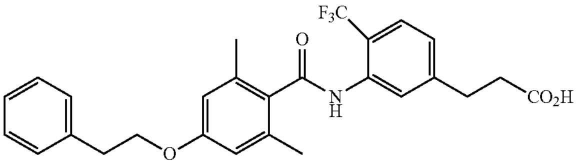 [SMILES: Cc1cc(OCCc2ccccc2)cc(C)c1C(=O)Nc1cc(CCC(=O)O)ccc1C(F)(F)F]

Palladium hydroxide (3 mg) was added to a solution of the residue produced in Reference Example 51 in THE (1 mL), and the resultant solution was stirred at room temperature for 1 hour under a hydrogen atmosphere. The reaction solution was filtrated through Celite (trade name), and was then concentrated under a reduced pressure. The resultant residue was purified by HPLC. In this manner, the compound of the present invention (0.62 mg) having the following physical property values was produced.

HPLC retention time (min): 1.20;

MS(ESI, Pos.): 486 $(M+H)^+$;

$^1$H-NMR (DMSO-$d_6$): δ2.30, 2.56-2.62, 2.92, 3.02, 4.19, 6.66, 7.19-7.25, 7.28-7.34, 7.34-7.37, 7.41, 7.67, 9.92, 12.11-12.32.

Examples 24-1 to 24-2

The same procedures as in Reference Example 50→Reference Example 51→Example 24 were carried out using, in place of ethyl acrylate, ethyl crotonate or ethyl methacrylate. In this manner, the compounds of the present invention having the following physical property values were produced.

Example 24-1: 3-[3-{[2,6-Dimethyl-4-(2-phenylethoxy)benzoyl]amino}-4-(trifluoromethyl)phenyl] butanoic acid

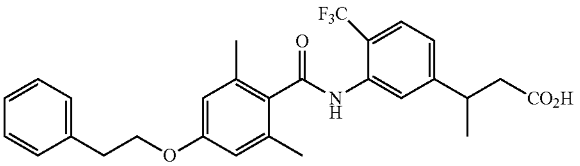 [SMILES: Cc1cc(OCCc2ccccc2)cc(C)c1C(=O)Nc1cc(C(C)CC(=O)O)ccc1C(F)(F)F]

HPLC retention time (min): 1.23;

MS(ESI, Pos.): 500 $(M+H)^+$;

$^1$H-NMR (DMSO-$d_6$): δ1.24, 2.30, 2.55-2.63, 2.96-3.05, 3.20-3.29, 4.19, 6.66, 7.17-7.25, 7.28-7.35, 7.38-7.43, 7.66-7.69, 9.91, 12.06-12.24.

Example 24-2: 3-[3-f{[2,6-Dimethyl-4-(2-phenylethoxy)benzoyl]amino}-4-(trifluoromethyl)phenyl]-2-methylpropanoic acid

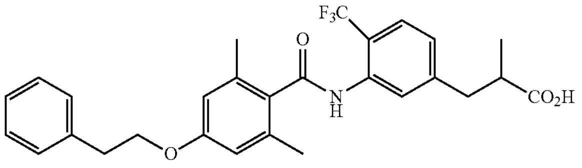 [SMILES: Cc1cc(OCCc2ccccc2)cc(C)c1C(=O)Nc1cc(CC(C)C(=O)O)ccc1C(F)(F)F]

HPLC retention time (min): 1.23;

MS(ESI, Pos.): 500 $(M+H)^+$;

$^1$H-NMR (DMSO-$d_6$): δ1.08, 2.29, 2.64-2.78, 2.94-3.04, 4.15-4.23, 6.66, 7.18-7.25, 7.27-7.36, 7.39, 7.67, 9.92, 12.25.

Reference Example 52: N-[5-Iodo-2-(trifluoromethyl)phenyl]-2,6-dimethyl-4-(2-phenylethoxy)benzamide The same procedure as in Reference Example 43 was carried out using, in place of the compound produced in Reference Example 31, the compound produced in Reference Example 27 and also using, in place of the compound produced in Reference Example 6, 5-iodo-2-(trifluoromethyl)aniline (CAS Number: 1544-89-4). In this manner, the title compound (1.45 g) having the following physical property values was produced.

HPLC retention time (min): 1.25;

MS(ESI, Pos.): 540 $(M+H)^+$.

Reference Example 53: 2-Methyl-2-propanyl[1-(dimethylamino)-1-oxo-3-phenyl-2-propanyl]carbamate 1-Ethyl-3-(3-dimethylaminopropyl)carbodiimide hydrochloride (CAS Number: 25952-53-8, 5.7 g) and DIPEA (10 mL) were added to a solution of 2-({[(2-methyl-2-propanyl)oxy]carbonyl}amino)-3-phenylpropanoic acid (CAS Number: 13734-34-4, 6.6 g), 1-hydroxybenzotriazole (CAS Number: 2592-95-2, 3.4 g) and dimethylamine hydrochloride (CAS Number: 506-59-2, 4.5 g) in dichloromethane (200 mL) under ice cooling, and the resultant solution was stirred at room temperature for 1 hour. The reaction solution was washed with a 10% aqueous citric acid solution and a saturated aqueous sodium bicarbonate solution, and was then dried over sodium sulfate anhydride, and a dried product was concentrated under a reduced pressure. The resultant residue was used in the subsequent reaction without being purified.

Reference Example 54: 2-Amino-N,N-dimethyl-3-phenylpropanamide hydrochloride

The crude product produced in Reference Example 53 was dissolved in a solution of 4N hydrochloric acid in ethyl acetate (25 mL), and the resultant solution was stirred at room temperature for 5 minutes. An additional amount of a solution of 4N hydrochloric acid in ethyl acetate (10 mL) was further added to the solution, and the resultant solution was stirred at room temperature for 3 hours. Precipitates were filtrated out. In this manner, the title compound (1.45 g) having the following physical property values was produced.

HPLC retention time (min): 0.49;

$^1$H-NMR (DMSO-$d_6$): δ2.63, 2.79, 2.88-3.00, 3.00-3.10, 4.50-4.61, 7.14-7.24, 7.27-7.42, 8.24.

Reference Example 55: (2S)—N1,N1-Dimethyl-3-phenyl-1,2-propanediamine

A suspension of the compound produced in Reference Example 54 (3 g) in THE (30 mL) was added dropwise to a suspension of lithium aluminum hydride (0.94 g) in THE (20 mL) under ice cooling, and the resultant solution was stirred at 50° C. for 2 hours. The reaction solution was cooled on ice, purified water (1 mL), a 4N aqueous sodium hydroxide solution (1 mL) and purified water (3 mL) were then added to the reaction solution, and the resultant solution was stirred at room temperature for 30 minutes. Magnesium sulfate anhydride was added to the reaction solution, and the resultant solution was stirred at room temperature for 15 minutes, and the resultant solution was filtrated through Celite (trade name), and was then concentrated under a reduced pressure. In this manner, the title compound (2.2 g) having the following physical property values was produced.

HPLC retention time (min): 0.34;

MS(ESI, Pos.): 179 $(M+H)^+$;

Reference Example 56: N-[(2S)-1-(Dimethylamino)-3-phenyl-2-propanyl]acetamide

Acetyl chloride (1 mL) was added to the compound produced in Reference Example 55 (2.1 g) in dichloromethane (20 mL) under ice cooling, and the resultant solution was stirred at room temperature for 5 minutes, and the reaction solution was concentrated under a reduced pressure. The resultant residue was dissolved in MTBE, the resultant solution was washed with a 5N aqueous sodium hydroxide solution and was then dried over sodium sulfate anhydride, and a dried product was concentrated under a reduced pressure. The resultant residue was slurry-washed with hexane. In this manner, the title compound (1.5 g) having the following physical property values was produced.

HPLC retention time (min): 0.50;

MS(ESI, Pos.): 221 $(M+H)^+$;

$^1$H-NMR ($CDCl_3$): δ1.97, 2.12-2.23, 2.26-2.36, 2.72-2.90, 2.93-3.04, 4.08-4.27, 5.50-5.65, 7.11-7.40.

Example 25: (1R,2S)-2-[3-{[2,6-Dimethyl-4-(2-phenylethoxy)benzoyl]amino}-4-(trifluoromethyl)phenyl]cyclobutanecarboxylic acid

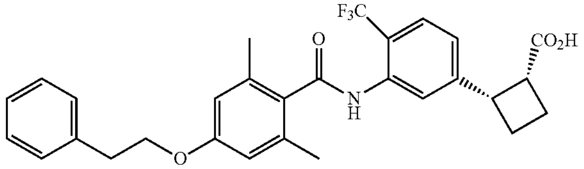 [SMILES: Cc1cc(OCCc2ccccc2)cc(C)c1C(=O)Nc1cc([C@H]2CC[C@H]2C(=O)O)ccc1C(F)(F)F]

Cyclobutanecarboxylic acid (CAS Number: 3721-95-7, 19 mg), silver carbonate (25 mg), sodium carbonate (15 mg), the compound produced in Reference Example 56 (4 mg) and palladium acetate (25 mg) were added to a solution of the compound produced in Reference Example 52 (50 mg) in 1,1,1,3,3,3-hexafluoro-2-propanol (CAS Number: 29463-77-2, 0.5 mL), and the resultant solution was stirred at 85° C. for 20 hours. The reaction solution was purified by silica gel column chromatography (hexane:(ethyl acetate)=97:3→0:1). In this manner, the compound of the present invention (10 mg) having the following physical property values was produced.

HPLC retention time (min): 1.12;

MS(ESI, Pos.): 512 $(M+H)^+$;

$^1$H-NMR ($CDCl_3$): δ2.22-2.48, 2.58-2.74, 3.10, 3.58-3.70, 4.03-4.24, 6.60, 7.18, 7.23-7.39, 7.47, 7.57, 8.14.

Example 26: (1R,2R)-2-[3-{[2,6-Dimethyl-4-(2-phenylethoxy)benzoyl]amino}-4-(trifluoromethyl)phenyl]-1-methylcyclopropanecarboxylic acid

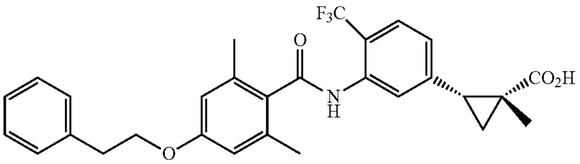 [SMILES: Cc1cc(OCCc2ccccc2)cc(C)c1C(=O)Nc1cc([C@H]2C[C@@]2(C)C(=O)O)ccc1C(F)(F)F]

The same procedure as in Example 25 was carried out using, in place of cyclobutanecarboxylic acid, 1-methylcyclopropane-1-carboxylic acid (CAS Number: 6914-76-7). In this manner, the compound of the present invention having the following physical property values was produced.

HPLC retention time (min): 1.30;

MS(ESI, Pos.): 512 $(M+H)^+$;

$^1$H-NMR ($CDCl_3$): δ1.23-1.30, 1.52, 1.92-2.00, 2.35, 2.41-2.49, 3.10, 4.18, 6.60, 7.12-7.20, 7.20-7.37, 7.44-7.54, 8.13.

Example 27: rel-(1R,2S)-2-(3-{[2,6-Dimethyl-4-(2-phenylethoxy)benzoyl]amino}-4-methylphenyl)cyclopropanecarboxylic acid Racemic Mixture

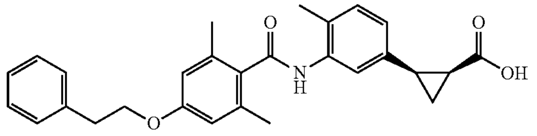

and

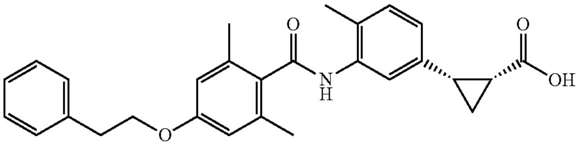

The same procedures as in Reference Example 40→Reference Example 4→Example 1 were carried out using, in place of 5-bromo-2-(trifluoromethyl)aniline, 5-bromo-2-methylaniline (CAS Number: 39478-78-9). In this manner, the compound of the present invention having the following physical property values was produced.

HPLC retention time (min): 2.19 (condition B);

MS(ESI, Pos.): 444 $(M+H)^+$;

$^1$H-NMR (DMSO-$d_6$): δ1.20-1.45, 1.75-2.02, 2.21, 2.31, 3.03, 4.20, 6.68, 6.94-6.99, 7.05-7.11, 7.20-7.37, 9.65.

Reference Example 57: Methyl 4-(benzyloxy)-2-bromobenzoate

Potassium carbonate (4.78 g) and benzyl bromide (2.1 mL) were added to a solution of methyl 2-bromo-4-hydroxybenzoate (CAS Number: 101085-03-4, 4.0 g) in DMF (20 mL), and the resultant solution was stirred at 70° C. for 3 hours. The reaction solution was diluted with water, and was then extracted with ethyl acetate. An organic layer was washed with water and saturated saline, was then dried over sodium sulfate anhydride, and was concentrated under a reduced pressure. The resultant residue was used in the subsequent reaction without being purified.

HPLC retention time (min): 2.38; (condition E)

MS(ESI, Pos.): 321 $(M+H)^+$.

Reference Example 58: Methyl 4-(benzyloxy)-2-isopropenylbenzoate

A solution of the compound produced in Reference Example 57 in ethanol (15 mL) and water (3.6 mL) was degassed, 2-isopropenyl-4,4,5,5-tetramethyl-1,3,2-dioxaborolane (CAS Number: 126726-62-3, 2.64 g), 2,6-di-tert-butyl-4-methylphenol (CAS Number: 128-37-0, 0.58 g), palladium acetate (0.44 g), tricyclohexylphosphine (CAS Number: 2622-14-2, 0.37 g) and potassium phosphate (8.32 g) were added to the solution, and the resultant solution was stirred at 90° C. for 16 hours. The reaction solution was diluted with water, and was then extracted with ethyl acetate. An organic layer was washed with water and saturated saline, was then dried over sodium sulfate anhydride, and a dried product was concentrated under a reduced pressure. The resultant residue was purified by silica gel column chromatography. In this manner, the title compound (3 g) having the following physical property values was produced.

HPLC retention time (min): 2.46; (condition E)

MS(ESI, Pos.): 283 $(M+H)^+$.

Reference Example 59: Methyl 4-(benzyloxy)-2-isopropyl benzoate

Platinum oxide (CAS Number: 1314-15-4, 10 mg) was added to a solution of the compound produced in Reference Example 58 in methanol (2.4 mL), and the resultant solution was stirred at room temperature for 16 hours under a hydrogen atmosphere. The reaction solution was filtrated through Celite, and the filtrate was concentrated under a reduced pressure. The resultant residue was used in the subsequent reaction without being purified.

HPLC retention time (min): 2.56; (condition E)

MS(ESI, Pos.): 285 $(M+H)^+$.

Reference Example 60: 4-(Benzyloxy)-2-isopropylbenzoic acid

Lithium hydroxide hydrate (CAS Number: 1310-66-3, 88 mg) was added to a solution of the compound produced in Reference Example 59 in methanol (0.5 mL), THE (0.5 mL) and water (0.5 mL), and the resultant solution was stirred at 60° C. for 16 hours. The reaction solution was concentrated, was then made acidic with hydrochloric acid, and was then extracted with ethyl acetate. An organic layer was washed with water and saturated saline, was then dried over sodium sulfate anhydride, and a dried product was concentrated under a reduced pressure. The resultant residue was used in the subsequent reaction without being purified.

HPLC retention time (min): 2.20; (condition E)

MS(ESI, Pos.): 271 $(M+H)^+$.

Example 28: (1R,2S)-2-[3-{[4-(Benzyloxy)-2-isopropylbenzoyl]amino}-4-(trifluoromethyl)phenyl]cyclopropanecarboxylic acid

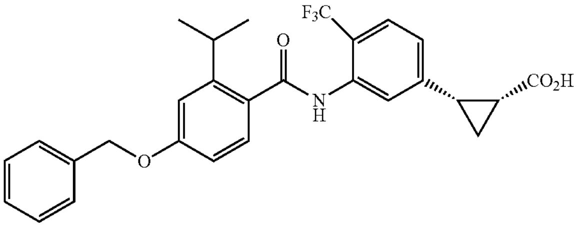 [SMILES: CC(C)c1cc(OCc2ccccc2)ccc1C(=O)Nc1cc([C@H]2C[C@H]2C(=O)O)ccc1C(F)(F)F]

The same procedures as in Reference Example 8→Example 1 were carried out using, in place of the compound produced in Example 3, the compound produced in Reference Example 60. In this manner, the compound of the present invention having the following physical property values was produced.

HPLC retention time (min): 2.36 (condition C);

MS(ESI, Pos.): 498 $(M+H)^+$;

$^1$H-NMR (DMSO-$d_6$): δ1.20, 1.31-1.40, 1.51-1.59, 2.03-2.12, 2.62-2.71, 3.33-3.45, 5.17, 6.93-6.96, 7.01, 7.30-7.51, 7.63, 9.91, 12.02.

Examples 28-1 to 28-2

The same procedures as in Reference Example 57→Reference Example 58→Reference Example 59→Reference Example 60→Reference Example 8→Example 1 were carried out using, in place of benzyl bromide, each of corresponding bromo compounds. In this manner, the compounds of the present invention having the following physical property values were produced.

Example 28-1: (1R,2S)-2-[3-{[2-Isopropyl-4-(2-phenylethoxy)benzoyl]amino}-4-(trifluoromethyl)phenyl]cyclopropanecarboxylic acid

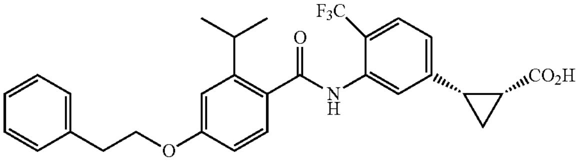 [SMILES: CC(C)c1cc(OCCc2ccccc2)ccc1C(=O)Nc1cc([C@H]2C[C@H]2C(=O)O)ccc1C(F)(F)F]

HPLC retention time (min): 2.42 (condition C);

MS(ESI, Pos.): 512 $(M+H)^+$;

$^1$H-NMR (DMSO-$d_6$): δ1.20, 1.30-1.38, 1.49-1.56, 2.01-2.13, 2.55-2.66, 3.06, 3.33-3.45, 4.25, 6.83-6.94, 7.20-7.27, 7.29-7.45, 7.62, 9.89.

Example 28-2: (1R,2S)-2-[3-{[2-Isopropyl-4-(3-phenylpropoxy)benzoyl]amino}-4-(trifluoromethyl)phenyl]cyclopropanecarboxylic acid

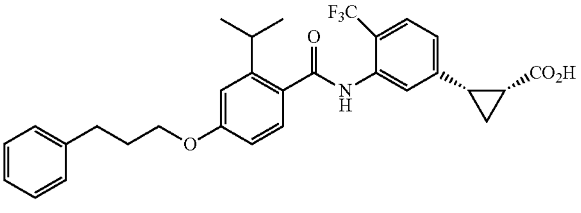 [SMILES: CC(C)c1cc(OCCCc2ccccc2)ccc1C(=O)Nc1cc([C@H]2C[C@H]2C(=O)O)ccc1C(F)(F)F]

HPLC retention time (min): 2.52 (condition C);

MS(ESI, Pos.): 526 $(M+H)^+$;

$^1$H-NMR (DMSO-$d_6$): δ1.19, 1.32-1.41, 1.51-1.59, 1.99-2.14, 2.60-2.72, 2.77, 3.34-3.49, 4.04, 6-83-6.89, 6.93, 7.16-7.46, 7.64, 9.91, 11.83.

Examples 29-1 to 29-3

The same procedures as in Reference Example 57→Reference Example 58→Reference Example 59→Reference Example 60→Reference Example 8→Example 1 were carried out using, in place of methyl 2-bromo-4-hydroxybenzoate, methyl 2-bromo-3-hydroxybenzoate (CAS Number: 1260783-82-1) and also using, benzyl bromide or in place of benzyl bromide, each of corresponding bromo compounds. In this manner, the compounds of the present invention having the following physical property values were produced.

Example 29-1: (1R,2S)-2-[3-{[3-(Benzyloxy)-2-isopropylbenzoyl]amino}-4-(trifluoromethyl)phenyl]cyclopropanecarboxylic acid

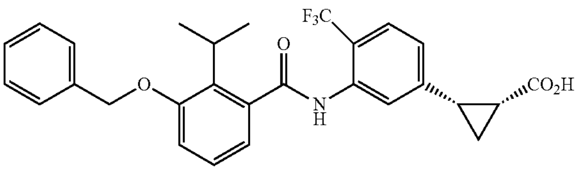 [SMILES: CC(C)c1c(OCc2ccccc2)cccc1C(=O)Nc1cc([C@H]2C[C@H]2C(=O)O)ccc1C(F)(F)F]

HPLC retention time (min): 4.96 (condition D);

MS(ESI, Pos.): 498 $(M+H)^+$;

$^1$H-NMR (DMSO-$d_6$): δ1.17-1.55, 1.91-2.04, 2.40-2.59, 3.11-3.25, 5.18, 6.97, 7.15, 7.21-7.53, 7.59, 10.02.

Example 29-2: (1R,2S)-2-[3-{[2-Isopropyl-3-(2-phenylethoxy)benzoyl]amino}-4-(trifluoromethyl)phenyl]cyclopropanecarboxylic acid

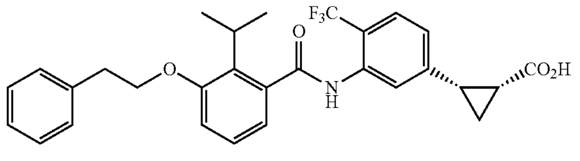 [SMILES: CC(C)c1c(OCCc2ccccc2)cccc1C(=O)Nc1cc([C@H]2C[C@H]2C(=O)O)ccc1C(F)(F)F]

HPLC retention time (min): 2.42 (condition C);

MS(ESI, Pos.): 512 $(M+H)^+$;

$^1$H-NMR (DMSO-$d_6$): δ1.21, 1.25-1.34, 1.45-1.53, 2.00-2.09, 2.51-2.62, 3.07-3.27, 4.26, 6.93, 7.08, 7.19-7.43, 7.60, 8.47, 9.97.

Example 29-3: (1R,2S)-2-[3-{[2-Isopropyl-3-(3-phenyl propoxy)benzoyl]amino}-4-(trifluoromethyl) phenyl]cyclopropanecarboxylic acid

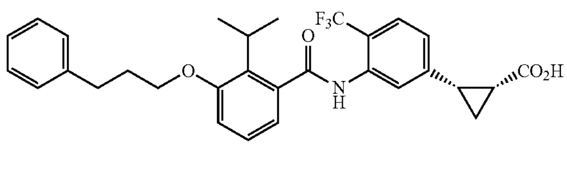 [SMILES: CC(C)c1c(OCCCc2ccccc2)cccc1C(=O)Nc1cc([C@H]2C[C@H]2C(=O)O)ccc1C(F)(F)F]

HPLC retention time (min): 2.52 (condition C);
MS(ESI, Pos.): 526 $(M+H)^+$;
$^1$H-NMR (DMSO-$d_6$): δ1.33-1.42, 1.51-1.62, 2.03-2.15, 2.61-2.87, 3.22-3.30, 4.00, 6.95, 7.03, 7.18-7.36, 7.44, 7.64, 10.02, 11.73.

Reference Example 61: 4-Bromo-2,3,6-trimethylphenol

A solution of bromine (1.6 mL) in dichloromethane (30 mL) was added to a solution of 2,3,6-trimethylphenol (CAS Number: 2416-94-6, 4.0 g) in dichloromethane (60 mL), and the resultant solution was stirred at room temperature for 5 hours. The reaction solution was concentrated under a reduced pressure, a sodium thiosulfate solution was then added to the solution, and the resultant solution was extracted with ethyl acetate. An organic layer was washed with water and saturated saline, was then dried over sodium sulfate anhydride, and a dried product was concentrated under a reduced pressure. In this manner, the title compound (5.9 g) having the following physical property values was produced.
$^1$H-NMR ($CDCl_3$): δ2.19, 2.21, 2.34, 4.56, 7.18.

Reference Example 62: 1-Bromo-2,3,5-trimethyl-4-(2-phenylethoxy)benzene

2-Phenyl ethanol(1.36 g) and triphenylphosphine (4.87 g) were added to a solution of the compound produced in Reference Example 61 (2.0 g) in THE (20 mL). Subsequently, DEAD (3.23 g, a 40% solution in toluene) was added dropwise to the solution, and the resultant solution was stirred at room temperature for 16 hours. Water was added to the reaction solution, and the resultant solution was extracted with ethyl acetate. An organic layer was washed with water and saturated saline, was then dried over sodium sulfate anhydride, and a dried product was concentrated under a reduced pressure. The resultant residue was purified by silica gel column chromatography ((petroleum ether):(ethyl acetate)=9:1). In this manner, the title compound (1.5 g) having the following physical property values was produced.
$^1$H-NMR ($CDCl_3$): δ2.11, 2.14, 2.30, 3.09, 3.89, 7.20-7.22, 7.27-7.32.

Reference Example 63: 2,3,5-Trimethyl-4-(2-phenylethoxy)benzoic acid

A solution of n-butyllithium in hexane (2.5 mol/L, 0.46 mL) was added to a solution of the compound produced in Reference Example 62 (0.3 g) in THE (6 mL) at −78° C., and the resultant solution was stirred at −78° C. for 15 minutes. The reaction solution was purged with a carbon dioxide gas at −78° C. for 5 minutes, and was then stirred at −78° C. for 20 minutes. Hydrochloric acid was added to the reaction solution to terminate the reaction, and the reaction solution was then extracted with ethyl acetate. An organic layer was washed with water and saturated saline, was then dried over sodium sulfate anhydride, and a dried product was concentrated under a reduced pressure. The resultant residue was used in the subsequent reaction without being purified.
HPLC retention time (min): 2.59 (condition F);
MS(ESI, Pos.): 285 $(M+H)^+$.

Example 30: (1R,2S)-2-[4-(Trifluoromethyl)-3-{[2,3,5-trimethyl-4-(2-phenylethoxy)benzoyl]amino}phenyl]cyclopropanecarboxylic acid

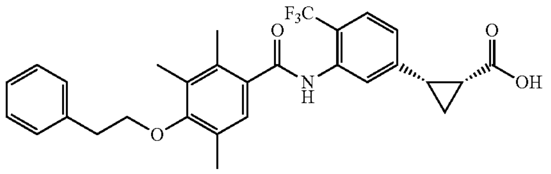 [SMILES: Cc1cc(C(=O)Nc2cc([C@H]3C[C@H]3C(=O)O)ccc2C(F)(F)F)c(C)c(C)c1OCCc1ccccc1]

The same procedures as in Reference Example 8→Example 1 were carried out using, in place of the compound produced in Reference Example 3, the compound produced in Reference Example 66. In this manner, the compound of the present invention having the following physical property values was produced.
HPLC retention time (min): 2.42 (condition C);
MS(ESI, Pos.): 512 $(M+H)^+$;
$^1$H-NMR (DMSO-$d_6$): δ1.31-1.36, 1.50-1.56, 2.04-2.13, 2.23, 2.55-2.66, 3.07, 3.93, 7.12, 7.22-7.26, 7.30-7.39, 7.42, 7.62, 9.90.

Reference Example 64: (1) Methyl 3-isopropyl-1-(3-phenylpropyl)-1H-pyrazol-4-carboxylate, and (2) methyl 5-isopropyl-1-(3-phenylpropyl)-1H-pyrazol-4-carboxylate Potassium carbonate (0.985 g) and 1-bromo-3-phenylpropane (1.42 g) were added to a solution of methyl 3-isopropyl-1H-pyrazole-4-carboxylate (CAS Number: 1186537-97-2, 0.4 g) in DMF (5 mL), and the resultant solution was stirred at 60° C. for 16 hours. The reaction solution was cooled to room temperature, ice-cold water was added to the reaction solution, and the resultant solution was extracted with ethyl acetate. An organic layer was washed with water and saturated saline, was then dried over sodium sulfate anhydride, and a dried product was concentrated under a reduced pressure. The resultant residue was purified by silica gel column chromatography ((petroleum ether):(ethyl acetate)=88:12). In this manner, the title compounds (0.41 g, a mixture) having the following physical property value were produced.
MS(ESI, Pos.): 287 $(M+H)^+$.

Examples 31-1 to 31-2

The same procedures as in Reference Example 27→Example 11 were carried out using, in place of the compound produced in Reference Example 26, the compound produced in Reference Example 64. In this manner, the compounds of the present invention having the following physical property values were produced.

Example 31-1: (1R,2S)-2-[3-({[3-Isopropyl-1-(3-phenylpropyl)-1H-pyrazol-4-yl]carbonyl}amino)-4-(trifluoromethyl)phenyl]cyclopropanecarboxylic acid

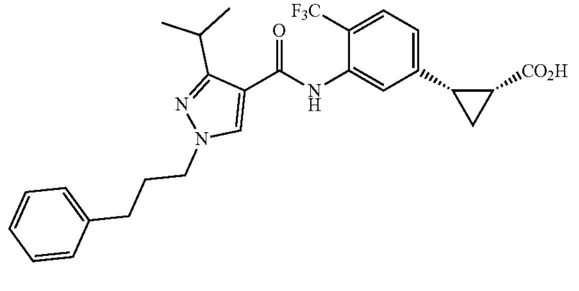 [SMILES: CC(C)c1nn(CCCc2ccccc2)cc1C(=O)Nc1cc([C@H]2C[C@H]2C(=O)O)ccc1C(F)(F)F]

HPLC retention time (min): 2.26 (condition C);
MS(ESI, Pos.): 500 $(M+H)^+$;
$^1$H-NMR (DMSO-$d_6$): δ1.15-1.21, 1.31-1.42, 1.50-1.58, 2.04-2.13, 2.55-2.73, 3.44-3.53, 4.09, 7.16-7.41, 7.62, 8.26, 9.37, 12.00.

Example 31-2: (1R,2S)-2-[3-({[5-Isopropyl-1-(3-phenylpropyl)-1H-pyrazol-4-yl]carbonyl}amino)-4-(trifluoromethyl)phenyl]cyclopropanecarboxylic acid

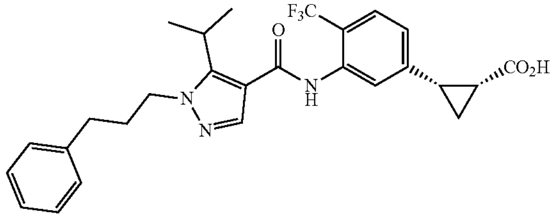 [SMILES: CC(C)c1c(C(=O)Nc2cc([C@H]3C[C@H]3C(=O)O)ccc2C(F)(F)F)cnn1CCCc1ccccc1]

HPLC retention time (min): 2.25 (condition C);
MS(ESI, Pos.): 500 $(M+H)^+$;
$^1$H-NMR (DMSO-$d_6$): δ1.16-1.32, 1.38-1.48, 1.90-2.09, 2.38-2.51, 2.59-2.68, 4.15, 7.15-7.25, 7.26-7.37, 7.56, 7.95, 9.53.

Reference Example 65: Ethyl (1R,2S)-2-[3-({[2,6-dimethyl-4-(2-phenylethoxy)phenyl]carbonothioyl}amino)-4-(trifluoromethyl)phenyl]cyclopropanecarboxylate Phosphorus pentasulfide (CAS Number: 1314-80-3, 42 mg) was added to a solution of the compound produced in Reference Example 42 (50 mg) in benzene (CAS Number: 71-43-2, 2 mL) at 0° C., and the resultant solution was stirred at 60° C. for 16 hours. The reaction solution was cooled to room temperature, ice-cold water was added to the reaction solution, and the resultant solution was extracted with ethyl acetate. An organic layer was washed with water and saturated saline, was then dried over sodium sulfate anhydride, and a dried product was concentrated under a reduced pressure. The resultant residue was used in the subsequent reaction without being purified.

HPLC retention time (min): 2.93 (condition F);
MS(ESI, Pos.): 542 $(M+H)^+$;

Example 32: (1R,2S)-2-[3-({[2,6-Dimethyl-4-(2-phenylethoxy)phenyl]carbonothioyl}amino)-4-(trifluoromethyl)phenyl]cyclopropanecarboxylic acid

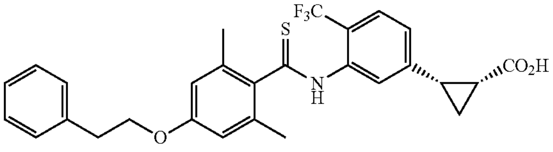 [SMILES: Cc1cc(OCCc2ccccc2)cc(C)c1C(=S)Nc1cc([C@H]2C[C@H]2C(=O)O)ccc1C(F)(F)F]

The same procedure as in Example 18 was carried out using, in place of the compound produced in Reference Example 42, the compound produced in Reference Example 65. In this manner, the compound of the present invention having the following physical property values was produced.

HPLC retention time (min): 2.39 (condition F);
MS(ESI, Pos.): 514 $(M+H)^+$;
$^1$H-NMR (DMSO-d6): δ1.21-1.34, 1.66-1.82, 2.28, 2.32-2.61, 3.01, 4.13, 6.45, 6.81-6.92, 7.05-7.14, 7.19-7.27, 7.29-7.36.

Example 33: (1R,2S)-2-[3-({[4-(2-Cyclopropylethoxy)-2,6-dimethylphenyl]carbonothioyl}amino)-4-(trifluoromethyl)phenyl]cyclopropanecarboxylic acid

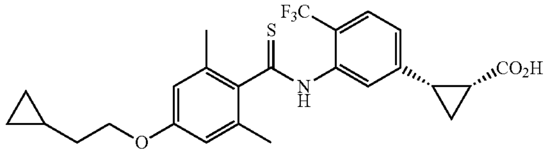 [SMILES: Cc1cc(OCCC2CC2)cc(C)c1C(=S)Nc1cc([C@H]2C[C@H]2C(=O)O)ccc1C(F)(F)F]

The same procedures as in Reference Example 65→Example 18 were carried out using, in place of the compound produced in Reference Example 42, ethyl (1R,2S)-2-[3-{[4-(2-cyclopropylethoxy)-2,6-dimethylbenzoyl]amino}-4-(trifluoromethyl)phenyl]cyclopropanecarboxylate that was an intermediate for Example 20-1. In this manner, the compound of the present invention having the following physical property values was produced.

HPLC retention time (min): 2.36 (condition F);
MS(ESI, Pos.): 478 $(M+H)^+$;
$^1$H-NMR (DMSO-d6): δ0.10-0.15, 0.41-0.47, 0.78-0.89, 1.37-1.44, 1.51-1.56, 1.59-1.66, 2.10-2.15, 2.34, 2.35, 2.67-2.75, 4.03, 6.68, 7.38-7.44, 7.68-7.73, 11.73, 12.02.

Reference Example 66: Ethyl 2-sec-butyl-1H-pyrrole-3-carboxylate

Aqueous ammonia (a 28% aqueous $NH_3$ solution, 3.2 mL) and water (3.2 mL) were added to a mixed solution of ethyl 4-methyl-3-oxohexanoate (CAS Number: 98192-72-4, 1.0 g) and an aqueous 2-chloroacetaldehyde solution (CAS Number: 107-20-0, 50 wt %, 0.815 mL), and the resultant solution was stirred at 70° C. for 20 hours. The reaction mixture was cooled to room temperature, and was then diluted with water and ethyl acetate. An organic layer was washed with water and saturated saline, was then dried over sodium sulfate anhydride, and a dried product was concentrated under a reduced pressure. The resultant residue was purified by silica gel column chromatography (hexane:(ethyl acetate)=9:1). In this manner, the title compound (300 mg) having the following physical property values was produced.

LC-MS m/z 196 $(M+H)^+$;

$^1$H-NMR ($CDCl_3$): δ0.91, 1.28, 1.37, 1.58-1.70, 3.65-3.73, 4.24-4.33, 6.58-6.61, 6.61-6.63, 8.19.

Reference Example 67: Ethyl 2-sec-butyl-1-(3-phenylpropyl)-1H-pyrrole-3-carboxylate Cesium carbonate (0.184 g) was added to a solution of the compound produced in Reference Example 66 (110 mg) and (3-bromopropyl)benzene (123 mg) in DMF (1 mL), and the resultant solution was stirred at 80° C. for 20 hours. The reaction solution was cooled to room temperature, and was then purified by silica gel column chromatography (hexane:(ethyl acetate)=8:2). In this manner, the title compound (98 mg) having the following physical property values was produced.

LC-MS m/z 314 $(M+H)^+$;

$^1$H-NMR ($CDCl_3$): δ0.82, 1.32-1.40, 1.74, 1.88, 2.00-2.12, 2.68, 3.23, 3.84-3.97, 4.25, 6.46, 6.59, 7.16-7.21, 7.21-7.27, 7.31-7.36.

Reference Example 68: 2-sec-Butyl-1-(3-phenylpropyl)-1H-pyrrole-3-carboxylic acid A 10N aqueous NaOH solution (0.1 mL) was added to a solution of the compound produced in Reference Example 67 (126 mg) in THF/methanol (1:1, 1 mL), and the resultant solution was stirred at 80° C. for 20 hours. The reaction solution was cooled to room temperature, and acetic acid (0.2 mL) was added thereto. Subsequently, dichloromethane (5 mL) and water (5 mL) were added to the resultant solution. An organic layer was washed with water and saturated saline, was then dried over sodium sulfate anhydride, and a dried product was concentrated under a reduced pressure. The resultant residue was purified by silica gel column chromatography (hexane:(ethyl acetate)=1:1). In this manner, the title compound (90 mg) having the following physical property values was produced.

LC-MS m/z 286 $(M+H)^+$;

$^1$H-NMR (DMSO-d6): δ0.71, 1.25, 1.63, 1.80, 1.89-2.06, 2.61, 3.20-3.39, 3.93, 6.37, 6.66, 7.18-7.26, 7.31.

Example 34: (1R,2S)-2-[3-({[2-sec-Butyl-1-(3-phenylpropyl)-1H-pyrrol-3-yl]carbonyl}amino)-4-(trifluoromethyl)phenyl]cyclopropanecarboxylic acid

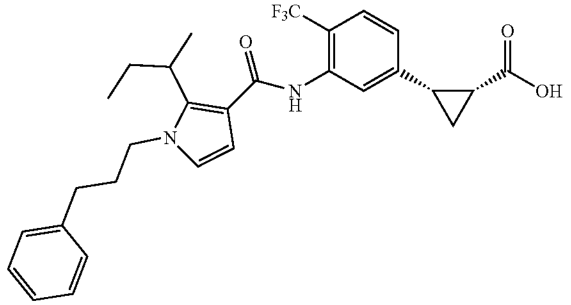 [SMILES: CCC(C)c1c(C(=O)Nc2cc([C@H]3C[C@H]3C(=O)O)ccc2C(F)(F)F)ccn1CCCc1ccccc1]

The same procedures as in Reference Example 8→Example 1 were carried out using, in place of the compound produced in Reference Example 3, the compound produced in Reference Example 68. In this manner, the compound of the present invention having the following physical property values was produced.

LC-MS m/z 513 $(M+H)^+$;

$^1$H-NMR (DMSO-d6): δ0.72, 1.16-1.31, 1.38, 1.47-1.58, 1.58-1.69, 1.78, 1.88-2.03, 2.03-2.20, 2.59-2.75, 3.32, 3.94, 6.54, 6.73, 7.19-7.28, 7.28-7.34, 7.50, 7.60, 8.94.

Examples 34-1 to 34-2

The same procedures as in Reference Example 66→Reference Example 67→Reference Example 68→Reference Example 8→Example 1 were carried out using, in place of ethyl 4-methyl-3-oxohexanoate, each of corresponding compounds. In this manner, the compounds of the present invention having the following physical property values were produced.

Example 34-1: (1R,2S)-2-[3-({[2-Isopropyl-1-(3-phenylpropyl)-1H-pyrrol-3-yl]carbonyl}amino)-4-(trifluoromethyl)phenyl]cyclopropanecarboxylic acid

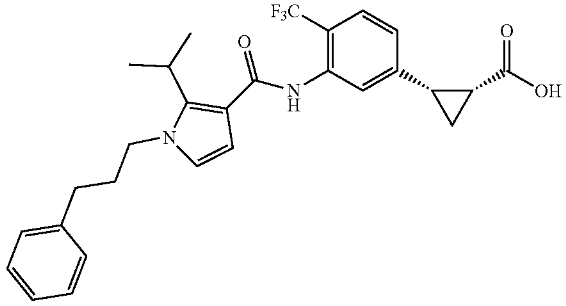 [SMILES: CC(C)c1c(C(=O)Nc2cc([C@H]3C[C@H]3C(=O)O)ccc2C(F)(F)F)ccn1CCCc1ccccc1]

LC-MS m/z 499 $(M+H)^+$;

$^1$H-NMR (DMSO-d6): δ1.27, 1.38, 1.51-1.56, 1.97, 2.07-2.13, 2.58-2.71, 3.35-3.59, 3.95, 6.52, 6.70, 7.18-7.28, 7.28-7.34, 7.51, 7.60, 8.95.

Example 34-2: (1R,2S)-2-[3-({[2-(2-Methyl-2-propanyl)-1-(3-phenylpropyl)-1H-pyrrol-3-yl]carbonyl}amino)-4-(trifluoromethyl)phenyl]cyclopropanecarboxylic acid

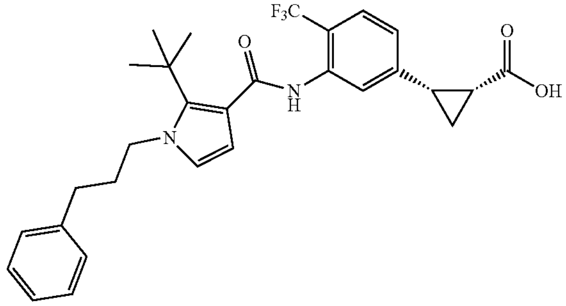 [SMILES: CC(C)(C)c1c(C(=O)Nc2cc([C@H]3C[C@H]3C(=O)O)ccc2C(F)(F)F)ccn1CCCc1ccccc1]

LC-MS m/z 513 $(M+H)^+$;

$^1$H-NMR (DMSO-d6): δ1.30-1.35, 1.38, 1.49, 1.98-2.16, 2.57-2.63, 2.70, 3.99-4.16, 6.09, 6.76, 7.20-7.25, 7.25-7.31, 7.31-7.37, 7.42, 7.60, 9.39.

PHARMACOLOGICAL EXPERIMENT EXAMPLE

Pharmacological Experiment Example 1: Experiment of Measuring $EP_2$ Antagonistic Activity Using Cells Expressing Prostanoid Receptor CHO cells on each of which a human $EP_2$ receptor had been expressed were prepared in accordance with the method by Nishigaki et al, (FEBS Letters, vol. 364, pp. 339-341, 1995) and were then cryopreserved in CELL-BANKER2 (Nippon Zenyaku Kogyo Co., Ltd.) at a concentration of $1.5\times10^7$ cells/mL/vial. The CHO cells thus prepared were used in the experiment. The cells were thawed, and were then suspended in an assay medium (D-PBS containing 1 mmol/L IBMX, 2 μmol/L Diclofenac) at a concentration of $5\times10^5$ cells/mL. $PGE_2$ alone having a final concentration of 10 nmol/L or a solution (10 μL) containing the $PGE_2$ and a test compound was added to the cell suspension (10 μL) to initiate the reaction. After the reaction was performed at room temperature for 1 hour, the amount of cAMP in the cells was quantified in accordance with the method described in cAMP Gs Dynamic kit (CISBIO).

The antagonistic activity ($IC_{50}$ value) of a test compound was calculated as a percentage of suppression of the reaction at 10 nM, which was a concentration at which a submaximal cAMP production activity was observed when $PGE_2$ alone was employed. In this manner, an $IC_{50}$ value was determined.

According to the pharmacological experiment, it was demonstrated that the compounds of the present invention had a potent antagonistic activity against an $EP_2$ receptor. For example, the $IC_{50}$ values of some of the compounds of the present invention are shown in Table 1.

TABLE 1

| Example No. | $EP_2$_$IC_{50}$ (nM) |
|---|---|
| 1 | <0.3 |
| 2 | 1.6 |
| 2-1 | 5.4 |
| 2-2 | 33 |
| 3-1 | 2.1 |
| 3-2 | 77 |
| 4 | 2.6 |
| 5 | 2.5 |
| 6 | <0.3 |
| 7 | 0.3 |
| 8 | 0.4 |
| 10 | 0.3 |
| 11 | 2.2 |
| 12 | 1.0 |
| 13 | 4.7 |
| 15 | <0.3 |
| 18 | 0.9 |
| 19 | 12 |
| 20 | 28 |
| 20-1 | 5.0 |
| 21 | 8.1 |
| 24 | 5.2 |
| 24-1 | 20 |
| 24-2 | 12 |
| 25 | 2.2 |
| 26 | 27 |
| 28 | 4.0 |
| 29-1 | 11 |

TABLE 1-continued

| Example No. | $EP_2$_$IC_{50}$ (nM) |
|---|---|
| 31-1 | 8.9 |
| 31-2 | 1.3 |
| 32 | 13 |
| 34 | <0.3 |

The antagonistic activity against an $EP_2$ receptor of the compound of Example 43 in Patent Document 1 was >10000 nM.

Pharmacological Experiment Example 2: Anti-Tumor Effect in Allogenic Transplantation Model of Mouse Colorectal Cancer Cell Line CT26

The anti-tumor effect of the compound of the present invention was evaluated in an allogenic transplantation model of CT26 that was a mouse colorectal cancer cell line. CT26 was cultured in a RPMI-1640 medium supplemented with 10 vol % of heat-inactivated fetal bovine serum (FBS), 100 units/mL of penicillin and 100 μg/mL of streptomycin in a $CO_2$ incubator. On the day of transplantation, a culture supernatant was removed, CT26 was washed with a phosphate buffered saline (also abbreviated as “PBS”, hereinafter) and was then collected. The collected CT26 was suspended in PBS and was used as cells for transplantation. 300,000 cells for the transplantation were transplanted subcutaneously into female Balb/C mice (Charles River Laboratories Japan) on the right back. Four days after the transplantation, the mice were divided into two groups, i.e., a medium group and a compound A group, each including 10 cases. Each of the medium and compound A (i.e., the compound of the present invention) was administered to the mice repeatedly at a dose amount of 10 mg/kg per single dose once per day on day-4 of the transplantation and twice per day in a period from day-5 and day-25 of the transplantation. With respect to a tumor volume ($mm^3$), a shorter diameter and a longer diameter of a tumor were measured with an electronic caliper, and the tumor volume was calculated in accordance with mathematical formula 1 shown below. In this experiment, a mouse in which an ulcer was formed in a tumor in the administered period was excluded from the evaluation on or after the time point of the formation of the ulcer.

$$\text{Tumor volume}=[(\text{shorter diameter})^2\times(\text{longer diameter})]/2 \qquad \text{[Mathematical formula 1]}$$

As a result, the compound of the present invention had a suppressive effect against the growth of a tumor. For example, when the compound of Example 18 was selected as compound A, the tumor volumes in a compound A-administered group on day-25 of the transplantation were significantly smaller compared with those in a medium-administered group, as shown in FIG. 1.

Pharmacokinetic Experiment 1: Liver Microsomal Stability Test (1) Preparation of Test Substance Solution A solution of a test substance in DMSO (10 mmol/L; 5 μL) was diluted with a 50% aqueous acetonitrile solution (195 μL) to prepare 250 μmol/L of a test substance solution.

(2) Preparation of Standard Sample (Sample Immediately after the Initiation of Reaction)

A 0.1-mol/L phosphate buffered saline (pH 7.4) (245 μL) containing NADPH-Co-Factor (BD-Bioscience) and 1 mg/mL of rat and human liver microsomes was added to a reaction container that had been warmed at 37° C. with a water bath, and the solution was preincubated for 5 minutes. The test substance solution (5 μL) was added to the solution to initiate the reaction (final concentration: 1 μmol/L). Immediately after the initiation of the reaction, an aliquot (20 μL) of the reaction solution was collected, and the solution was added to acetonitrile (containing candesartan as an internal standard substance) (180 μL) to terminate the reaction. The solution in which the reaction had been terminated (i.e., a sample solution immediately after the initiation of the reaction; 20 μL) was agitated together with 50% acetonitrile (180 μL) on a filter plate for protein removal use, the resultant solution was filtrated by suction, and the filtrate was used a standard sample.

(3) Preparation of Reaction Sample (Sample 60 Minutes after the Reaction)

The reaction solution was incubated at 37° C. for 60 minutes, and then an aliquot (20 μL) of the reaction solution was collected and was added to acetonitrile (containing candesartan as an internal standard substance) (180 μL) to terminate the reaction. The solution in which the reaction had been terminated (i.e., a sample solution that had been reacted for 60 minutes; 20 μL) was agitated together with 50% acetonitrile (180 μL) on a filter plate for protein removal use, the resultant solution was filtrated by suction, and the filtrate was used a standard sample.

(4) Evaluation Method

The residual ratio (%) of a test substance was calculated using a peak area obtained by LC-MS/MS, from the amount of the test substance in the standard sample (X) and the amount of the test substance in a reaction sample (Y) in accordance with the following formula.

$$\text{Residual ratio } (\%) = (Y/X) \times 100$$

X: the amount of a test substance in the standard sample (Ratio=(peak area of test substance)/(peak area of internal standard substance))

Y: the amount of a test substance in a reaction sample (Ratio=(peak area of test substance)/(peak area of internal standard substance))

(5) Results

It was demonstrated that the compound of the present invention had high stability against human liver microsomes.

Pharmacokinetic Experiment Example 2: Solubility Measurement Test (1) Preparation of Solution for Calibration Curve A solution for calibration curve was prepared by diluting a solution of a test substance in DMSO (10 mmol/L) with acetonitrile, and then adding acetonitrile containing nicardipine as an internal standard substance to the diluted solution to prepare a solution having a concentration of each of 5, 20 and 100 nmol/L.

(2) Preparation of Sample Solution

A sample solution was prepared by adding a solution of a test substance in DMSO (10 mmol/L; 5 μL) to solution II defined in Japanese Pharmacopoeia (495 μL), then agitating the solution at room temperature for 5 hours, then placing the solution on a filter plate for solubility use, then filtrating the solution by suction, diluting filtrate (10 μL) with acetonitrile, and then adding acetonitrile containing an internal standard substance (nicardipine) to the solution.

(3) Evaluation

Each of the solution for calibration curve and the sample solution (5 μL) was injected into LC-MS (Thermo Scientific; Q Exactive Focus) to perform quantification (range of quantification: 5 to 100 nmol/L). A solubility was calculated by multiplying a quantification value by 1000. When a value equal to or smaller than the quantification range was obtained, the solubility was determined as <5 μmol/L. When a value equal to or more than the quantification range was obtained, the solubility was determined as 100 μmol/L.

(4) Results

It was demonstrated that the compound of the present invention had a satisfactory solubility.

FORMULATION EXAMPLE

Formulation Example

The components shown below were mixed together in the conventional manner and the mixture was compressed into tablets. In this manner, 10,000 tablets each containing 10 mg of the active component per tablet were produced.

(1R,2S)-2-{3-[({1-[(2S)-2-butanyl]-5-(3-phenylpropyl)-1H-pyrrol-2-yl}carbonyl)amino]-4-chlorophenyl}cyclopropanecarboxylic acid: 100 g Carboxymethyl cellulose potassium (disintegrating agent): 20 g Magnesium stearate (lubricant): 10 g Microcrystalline cellulose: 870 g

INDUSTRIAL APPLICABILITY

The compound of the present invention has an antagonistic activity against an $EP_2$ receptor. Therefore, the compound of the present invention is useful for a prevention and/or treatment of a disease associated with the activation of an $EP_2$ receptor.

The invention claimed is:

1. A compound of formula (I-1):

(I-1)

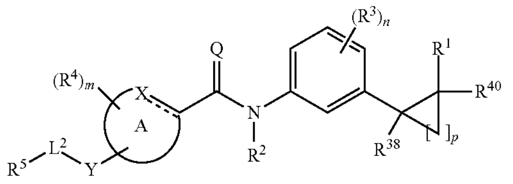

wherein:

$R^{38}$ and $R^{40}$ each independently represent (1) a hydrogen atom, (2) a halogen atom, or (3) a C1-4 alkyl group;

the C1-4 alkyl group in each of $R^{38}$ and $R^{40}$ may be independently substituted by a halogen atom;

$L^2$ represents (1) a bond, (2) a C1-8 alkylene group, (3) a C2-8 alkenylene group, or (4) a C2-8 alkynylene group, wherein one or two carbon atoms in the C1-8 alkylene group, the C2-8 alkenylene group and the C2-8 alkynylene group may be independently replaced by an oxygen atom or a sulfur atom that may be oxidized, and each of the C1-8 alkylene group, the C2-8 alkenylene group and the C2-8 alkynylene group may be substituted by 1 to 8 halogen atoms;

Y represents (1) a bond, (2) an oxygen atom, or (3) a sulfur atom that may be oxidized;

$R^1$ represents (1) $COOR^{10}$;

$R^{10}$ represents (1) a hydrogen atom or (2) a C1-4 alkyl group;

$R^2$ represents (1) a hydrogen atom or (2) a C1-4 alkyl group;

$R^3$ represents (1) a halogen atom, (2) a C1-6 alkyl group, (3) a C2-6 alkenyl group, (4) a C2-6 alkynyl group, (5) a C1-6 alkoxy group, (6) a 3- to 6-membered cyclic group, (7) a (3- to 6-membered cyclic group)-O—, or (8) a (3- to 6-membered cyclic group)-(C1-4 alkylene)-;

each of the groups (2) to (8) in $R^3$ may be substituted by 1 to 9 $R^{16}$s;

when there are a plurality of $R^3$s, the plurality of $R^3$s may be the same as or different from each other;

$R^{16}$ represents (1) a halogen atom, (2) a C1-4 alkyl group, (3) a C1-4 alkoxy group, (4) a C2-6 acyl group, (5) a C3-6 cycloalkyl group, (6) a hydroxyl group, or (7) $—NR^{17}R^{18}$;

when there are a plurality of $R^{16}$s, the plurality of $R^{16}$s may be the same as or different from each other;

$R^{17}$ and $R^{18}$ each independently represent (1) a hydrogen atom or (2) a C1-4 alkyl group;

$R^4$ represents (1) a halogen atom, (2) a C1-6 alkyl group, (3) a C2-6 alkenyl group, (4) a C2-6 alkynyl group, (5) a C1-6 alkoxy group, (6) a 3- to 6-membered cyclic group, (7) (3- to 6-membered cyclic group)-O—, or (8) (3- to 6-membered cyclic group)-(C1-4 alkylene)-;

each of the groups (2) to (8) in $R^4$ may be substituted by 1 to 9 $R^{19}$s;

when there are a plurality of $R^4$s, the plurality of $R^4$s may be the same as or different from each other;

$R^{19}$ represents (1) a halogen atom, (2) a C1-4 alkyl group, (3) a C1-4 alkoxy group, (4) a C2-6 acyl group, (5) a C3-6 cycloalkyl group, (6) a hydroxyl group, or (7) $—NR^{20}R^{21}$;

$R^{20}$ and $R^{21}$ each independently represent (1) a hydrogen atom or (2) a C1-4 alkyl group;

when there are a plurality of $R^{19}$s, the plurality of $R^{19}$s may be the same as or different from each other;

$R^5$ represents (1) a hydrogen atom, (2) a C3-10 carbocyclic ring, or (3) a 3- to 10-membered heterocyclic ring, wherein each of the C3-10 carbocyclic ring and the 3- to 10-membered heterocyclic ring may be substituted by 1 to 5 $R^{22}$s;

when $L^2$ represents a bond, $R^5$ is not a hydrogen atom;

$R^{22}$ represents (1) a C1-6 alkyl group, (2) a C2-6 alkenyl group, (3) a C2-6 alkynyl group, (4) a C3-6 cycloalkyl group, (5) a C1-6 alkoxy group, (6) a C3-6 cycloalkyloxy group, (7) a C2-6 acyl group, (8) a C2-6 acyloxy group, (9) a C1-6 alkylthio group, (10) a C3-6 cycloalkylthio group, (11) a C1-6 alkylsulfinyl group, (12) a C3-6 cycloalkylsulfinyl group, (13) a C1-6 alkylsulfonyl group, (14) a C3-6 cycloalkylsulfonyl group, (15) a C1-6 alkoxycarbonyl group, (16) a 5- to 6-membered cyclic group, (17) (5- to 6-membered cyclic group)-(C1-4 alkylene)-, (18) a (5- to 6-membered cyclic group)-(C1-4 alkylene)-O— group, (19) a (5- to 6-membered cyclic group)-C1-4 acyl group, (20) a halogen atom, (21) a hydroxyl group, (22) a nitro group, (23) a cyano group, (24) $—NR^{23}R^{24}$, (25) $—CONR^{25}R^{26}$ or (26) $—SO_2NR^{27}R^{28}$, $R^{23}$, $R^{24}$, $R^{25}$, $R^{26}$, $R^{27}$ and $R^{28}$ each independently represent (1) a hydrogen atom, (2) a C1-6 alkyl group, (3) a C2-6 acyl group or (4) a C1-6 alkylsulfonyl group;

each of the groups (1) to (19) in $R^{22}$ may be substituted by 1 to 9 $R^{29}$s;

when there are a plurality of $R^{22}$s, the plurality of $R^{22}$s may be the same as or different from each other;

$R^{29}$ represents (1) a C1-4 alkyl group, (2) a C1-4 alkoxy group, (3) a C2-6 acyl group, (4) a C3-6 cycloalkyl group, (5) a hydroxyl group, (6) $—NR^{30}R^{31}$ or (7) a halogen atom;

$R^{30}$ and $R^{31}$ each independently represent (1) a hydrogen atom or (2) a C1-4 alkyl group;

when there are a plurality of $R^{29}$s, the plurality of $R^{29}$s may be the same as or different from each other;

X represents (1) $CR^6$ or (2) $NR^7$;

$R^6$ represents (1) a halogen atom, (2) a C1-6 alkyl group, (3) a C2-6 alkenyl group, (4) a C2-6 alkynyl group, (5) a C1-6 alkoxy group, (6) a 3- to 6-membered cyclic group, (7) (3- to 6-membered cyclic group)-O—, or (8) (3- to 6-membered cyclic group)-(C1-4 alkylene)-;

each of the groups (2) to (8) in $R^6$ may be substituted by 1 to 9 $R^{32}$s;

$R^{32}$ represents (1) a halogen atom, (2) a C1-4 alkyl group, (3) a C1-4 alkoxy group, (4) a C2-6 acyl group, (5) a C3-6 cycloalkyl group, (6) a hydroxyl group, or (7) $—NR^{33}R^{34}$;

$R^{33}$ and $R^{34}$ each independently represent (1) a hydrogen atom or (2) a C1-4 alkyl group;

when there are a plurality of $R^{32}$s, the plurality of $R^{32}$s may be the same as or different from each other;

$R^7$ represents (1) a C1-6 alkyl group, (2) a C2-6 alkenyl group, (3) a C2-6 alkynyl group, (4) a 3- to 6-membered cyclic group, or (5) (3- to 6-membered cyclic group)-(C1-4 alkylene)-;

$R^7$ may be substituted by 1 to 9 $R^{35}$s;

$R^{35}$ represents (1) a halogen atom, (2) a C1-4 alkyl group, (3) a C1-4 alkoxy group, (4) a C2-6 acyl group, (5) a C3-6 cycloalkyl group, (6) a hydroxyl group, or (7) $—NR^{36}R^{37}$, $R^{36}$ and $R^{37}$ each independently represent (1) a hydrogen atom or (2) a C1-4 alkyl group;

when there are a plurality of $R^{35}$s, the plurality of $R^{35}$s may be the same as or different from each other;

the ring A represents (1) a benzene ring, or (2) a 5- to 6-membered nitrogen-containing aromatic heterocyclic ring;

the symbol in the ring A represents a single bond or a double bond;

n represents an integer of 1 to 4;

m represents an integer of 0 to 3; and p represents an integer of 1 to 4, or a pharmaceutically acceptable salt thereof.

2. The compound according to claim 1, or a pharmaceutically acceptable salt thereof, wherein the compound is a compound of formula (I-C):

(I-C)

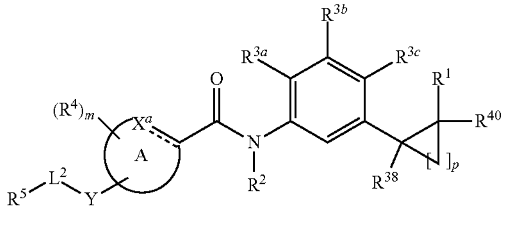

wherein:

$X^a$ represents $CR^{6a}$ or $NR^{7a}$;

$R^{6a}$ represents (1) a halogen atom, (2) a C1-6 alkyl group, (3) a C2-6 alkenyl group, (4) a C2-6 alkynyl group, (5) a C1-6 alkoxy group, (6) (3- to 6-membered cyclic group)-O—, or (7) (3- to 6-membered cyclic group)-(C1-4 alkylene)-;

each of the groups (2) to (7) in $R^{6a}$ may be substituted by 1 to 9 $R^{32}$s;

$R^{7a}$ represents (1) a C1-6 alkyl group, (2) a C2-6 alkenyl group, (3) a C2-6 alkynyl group, (4) a 3- to 6-membered cyclic group, or (5) (3- to 6-membered cyclic group)-(C1-4 alkylene)-;

$R^{7a}$ may be substituted by 1 to 9 $R^{35}$s;

$R^{3a}$, $R^{3b}$ and $R^{3c}$ each independently represent (1) a hydrogen atom, (2) a halogen atom, (3) a C1-6 alkyl group, (4) a C2-6 alkenyl group, (5) a C2-6 alkynyl group, (6) a C1-6 alkoxy group, (7) a 3- to 6-membered cyclic group, (8) (3- to 6-membered cyclic group)-O—, or (9) (3- to 6-membered cyclic group)-(C1-4 alkylene)-;

each of the groups (3) to (9) in $R^{3a}$, $R^{3b}$ and $R^{3c}$ may be substituted by 1 to 9 $R^{16}$s;

wherein at least one of $R^{3a}$, $R^{3b}$ and $R^{3c}$ represents a substituent other than a hydrogen atom;

p represents an integer of 1 to 4; and the same symbols as those recited in claim 1 have the same meanings as those recited in claim 1.

3. The compound according to claim 1, or a pharmaceutically acceptable salt thereof, wherein the ring A is a benzene ring or a 5-membered nitrogen-containing aromatic heterocyclic ring.

4. The compound according to claim 1, or a pharmaceutically acceptable salt thereof, wherein the ring A is a pyrrole ring and Y is a bond.

5. The compound according to claim 1, or a pharmaceutically acceptable salt thereof, wherein the ring A is a benzene ring and Y is an oxygen atom.

6. The compound according to claim 1, or a pharmaceutically acceptable salt thereof, wherein the compound is selected from:

(1) rel-(1R,2S)-2-{3-([1-sec-butyl-5-(3-phenylpropyl)-1H-pyrrole-2-carbonyl]amino)-4-(trifluoromethyl)phenyl}cyclopropanecarboxylic acid;

(2) rel-(1R,2S)-2-{3-[({1-[(2S)-2-butanyl]-5-(3-phenylpropyl)-1H-pyrrol-2-yl}carbonyl)amino]-4-(trifluoromethyl)phenyl}cyclopropanecarboxylic acid;

(3) rel-(1R,2S)-2-{3-[({1-[(2S)-2-butanyl]-5-(3-phenylpropyl)-1H-pyrrol-2-yl}carbonyl)amino]-5-methylphenyl}cyclopropanecarboxylic acid;

(4) rel-(1R,2R)-2-{3-[({1-[(2S)-2-butanyl]-5-(3-phenylpropyl)-1H-pyrrol-2-yl}carbonyl)amino]-5-methylphenyl}cyclopropanecarboxylic acid;

(5) rel-(1R,2S)-2-{5-[({1-[(2S)-2-butanyl]-5-(3-phenylpropyl)-1H-pyrrol-2-yl}carbonyl)amino]-2-(trifluoromethyl)phenyl}cyclopropanecarboxylic acid;

(6) rel-(1R,2R)-2-{5-[({1-[(2S)-2-butanyl]-5-(3-phenylpropyl)-1H-pyrrol-2-yl}carbonyl)amino]-2-(trifluoromethyl)phenyl}cyclopropanecarboxylic acid;

(7) (1S,2R)-2-[3-({[1-isopropyl-5-(3-phenylpropyl)-1H-pyrrol-2-yl]carbonyl}amino)-4-(trifluoromethyl)phenyl]cyclopropanecarboxylic acid;

(8) (1R,2R)-2-[3-({[1-isopropyl-5-(3-phenylpropyl)-1H-pyrrol-2-yl]carbonyl}amino)-4-(trifluoromethyl)phenyl]cyclopropanecarboxylic acid;

(9) (1R,2S)-2-{3-[({1-[(2S)-2-butanyl]-5-(3-phenylpropyl)-1H-pyrrol-2-yl}carbonyl)amino]-4-methoxyphenyl}cyclopropanecarboxylic acid;

(10) (1S,2R)-2-{3-[({1-[(2S)-2-butanyl]-5-(3-phenylpropyl)-1H-pyrrol-2-yl}carbonyl)amino]-4-(trifluoromethyl)phenyl}cyclopropanecarboxylic acid;

(11) (1R,2S)-2-{3-[({1-[(2S)-2-butanyl]-5-(3-phenylpropyl)-1H-pyrrol-2-yl}carbonyl)amino]-4-(trifluoromethyl)phenyl}cyclopropanecarboxylic acid;

(12) (1R,2S)-2-{3-[({1-[(2S)-2-butanyl]-5-(3-phenylpropyl)-1H-pyrrol-2-yl}carbonyl)amino]-4-chlorophenyl}cyclopropanecarboxylic acid;

(13) (1R,2S)-2-{3-[({5-[2-(benzyloxy)ethyl]-1-[(2S)-2-butanyl]-1H-pyrrol-2-yl}carbonyl)amino]-4-(trifluoromethyl)phenyl}cyclopropanecarboxylic acid;

(14) rel-(1R,2S)-2-[3-{[(1-[(2S)-2-butanyl]-5-{2-[(2-fluoro-4-pyridinyl)oxy]ethyl}-1H-pyrrol-2-yl)carbonyl]amino}-4-(trifluoromethyl)phenyl]cyclopropanecarboxylic acid;

(15) (1R,2S)-2-[3-{[(1-[(2S)-2-butanyl]-5-{2-[(2-chloro-6-fluoro-4-pyridinyl)oxy]ethyl}-1H-pyrrol-2-yl)carbonyl]amino}-4-(trifluoromethyl)phenyl]cyclopropanecarboxylic acid;

(16) (1R,2S)-2-{3-[({1-[(2S)-2-butanyl]-5-[2-(2-chloro-3,5-difluorophenoxy)ethyl]-1H-pyrrol-2-yl}carbonyl)amino]-4-(trifluoromethyl)phenyl}cyclopropanecarboxylic acid;

(17) (1R,2S)-2-{3-[({1-[(2S)-2-butanyl]-5-[2-(2,4-difluorophenoxy)ethyl]-1H-pyrrol-2-yl}carbonyl)amino]-4-(trifluoromethyl)phenyl}cyclopropanecarboxylic acid;

(18) (1R,2S)-2-[3-{[(1-[(2S)-2-butanyl]-5-{2-[(1-methyl-1H-pyrazol-4-yl)oxy]ethyl}-1H-pyrrol-2-yl)carbonyl]amino}-4-(trifluoromethyl)phenyl]cyclopropanecarboxylic acid;

(19) rel-(1R,2S)-2-[3-{[2,6-dimethyl-4-(2-phenylethoxy)benzoyl]amino}-4-(trifluoromethyl)phenyl]cyclopropanecarboxylic acid;

(20) (1R,2S)-2-[3-{[2,6-dimethyl-4-(3-phenylpropyl)benzoyl]amino}-4-(trifluoromethyl)phenyl]cyclopropanecarboxylic acid;

(21) (1R,2S)-2-[3-({4-[2-(2,4-difluorophenyl)ethoxy]-2,6-dimethylbenzoyl}amino)-4-(trifluoromethyl)phenyl]cyclopropanecarboxylic acid;

(22) rel-(1R,2S)-2-(2,3-dichloro-5-{[2,6-dimethyl-4-(2-phenylethoxy)benzoyl]amino}-4-fluorophenyl)cyclopropanecarboxylic acid;

(23) rel-(1R,2R)-2-(2,3-dichloro-5-{[2,6-dimethyl-4-(2-phenylethoxy)benzoyl]amino}-4-fluorophenyl)cyclopropanecarboxylic acid;

(24) (1R,2S)-2-[2-chloro-5-{[2,6-dimethyl-4-(2-phenylethoxy)benzoyl]amino}-4-(trifluoromethyl)phenyl]cyclopropanecarboxylic acid;

(25) (1R,2S)-2-(4-chloro-3-{[2,6-dimethyl-4-(2-phenylethoxy)benzoyl]amino}phenyl)cyclopropanecarboxylic acid;

(26) rel-(1R,2S)-2-(2,3-dichloro-5-{[2,6-dimethyl-4-(2-phenylethoxy)benzoyl]amino}phenyl)cyclopropanecarboxylic acid;

(27) rel-(1R,2R)-2-(2,3-dichloro-5-{[2,6-dimethyl-4-(2-phenylethoxy)benzoyl]amino}phenyl)cyclopropanecarboxylic acid;

(28) (1R,2S)-2-[3-{[2,6-dimethyl-4-(2-phenylethoxy)benzoyl]amino}-4-(trifluoromethyl)phenyl]cyclopropanecarboxylic acid;

(29) (1S,2R)-2-[3-{[2,6-dimethyl-4-(2-phenylethoxy)benzoyl]amino}-4-(trifluoromethyl)phenyl]cyclopropanecarboxylic acid;

(30) (1R,2S)-2-[3-({2,6-dimethyl-4-[2-(1-methyl-1H-pyrazol-4-yl)ethoxy]benzoyl}amino)-4-(trifluoromethyl)phenyl]cyclopropanecarboxylic acid;
(31) (1R,2S)-2-[3-{[4-(2-cyclopropylethoxy)-2,6-dimethylbenzoyl]amino}-4-(trifluoromethyl)phenyl]cyclopropanecarboxylic acid;
(32) (1R,2S)-2-{3-[(2,6-dimethyl-4-propoxybenzoyl)amino]-4-(trifluoromethyl)phenyl}cyclopropanecarboxylic acid;
(33) (1R,2S)-2-[3-{[4-(hexyloxy)-2,6-dimethylbenzoyl]amino}-4-(trifluoromethyl)phenyl]cyclopropanecarboxylic acid;
(34) (1R,2S)-2-[3-{[4-(benzyloxy)-2,6-dimethylbenzoyl]amino}-4-(trifluoromethyl)phenyl]cyclopropanecarboxylic acid;
(35) (1R,2S)-2-[3-{[4-(2-methoxyethoxy)-2,6-dimethylbenzoyl]amino}-4-(trifluoromethyl)phenyl]cyclopropanecarboxylic acid;
(36) (1R,2S)-2-[3-({2,6-dimethyl-4-[2-(tetrahydro-2H-pyran-2-yl)ethoxy]benzoyl}amino)-4-(trifluoromethyl)phenyl]cyclopropanecarboxylic acid;
(37) (1R,2S)-2-[3-({4-[2-(2-furyl)ethoxy]-2,6-dimethylbenzoyl}amino)-4-(trifluoromethyl)phenyl]cyclopropanecarboxylic acid;
(38) (1R,2S)-2-[3-({4-[2-(2-chlorophenyl)ethoxy]-2,6-dimethylbenzoyl}amino)-4-(trifluoromethyl)phenyl]cyclopropanecarboxylic acid;
(39) (1R,2S)-2-[3-({4-[2-(3-chlorophenyl)ethoxy]-2,6-dimethylbenzoyl}amino)-4-(trifluoromethyl)phenyl]cyclopropanecarboxylic acid;
(40) (1R,2S)-2-[3-({4-[2-(1H-imidazol-1-yl)ethoxy]-2,6-dimethylbenzoyl}amino)-4-(trifluoromethyl)phenyl]cyclopropanecarboxylic acid;
(41) (1R,2S)-2-[3-({4-[2-(2,6-difluorophenyl)ethoxy]-2,6-dimethylbenzoyl}amino)-4-(trifluoromethyl)phenyl]cyclopropanecarboxylic acid;
(42) (1R,2S)-2-[3-({4-[2-(3,5-difluorophenyl)ethoxy]-2,6-dimethylbenzoyl}amino)-4-(trifluoromethyl)phenyl]cyclopropanecarboxylic acid;
(43) (1R,2S)-2-[3-({4-[(6-chloro-2-pyrazinyl) oxy]-2,6-dimethylbenzoyl}amino)-4-(trifluoromethyl)phenyl]cyclopropanecarboxylic acid;
(44) (1R,2S)-2-[3-{[4-(6-fluoro-3-pyridinyl)-2,6-dimethylbenzoyl]amino}-4-(trifluoromethyl)phenyl]cyclopropanecarboxylic acid;
(45) (1R,2S)-2-[3-({4-[2-(4-hydroxyphenyl)ethoxy]-2,6-dimethylbenzoyl}amino)-4-(trifluoromethyl)phenyl]cyclopropanecarboxylic acid;
(46) 3-[3-{[2,6-dimethyl-4-(2-phenylethoxy)benzoyl]amino}-4-(trifluoromethyl)phenyl] propanoic acid;
(47) 3-[3-{[2,6-dimethyl-4-(2-phenylethoxy)benzoyl]amino}-4-(trifluoromethyl)phenyl] butanoic acid;
(48) 3-[3-{[2,6-dimethyl-4-(2-phenylethoxy)benzoyl]amino}-4-(trifluoromethyl)phenyl]-2-methylpropanoic acid;
(49) (1R,2S)-2-[3-{[2,6-dimethyl-4-(2-phenylethoxy)benzoyl]amino}-4-(trifluoromethyl)phenyl]cyclobutanecarboxylic acid; or
(50) (1R,2R)-2-[3-{[2,6-dimethyl-4-(2-phenylethoxy)benzoyl]amino}-4-(trifluoromethyl)phenyl]-1-methylcyclopropanecarboxylic acid.

7. The compound according to claim 1, or a pharmaceutically acceptable salt thereof, wherein the compound is selected from:
(1) (1R,2S)-2-[3-{[2-methyl-4-(2-phenylethoxy)benzoyl]amino}-4-(trifluoromethyl)phenyl]cyclopropanecarboxylic acid;
(2) (1R,2S)-2-[3-{[2-chloro-4-(2-phenylethoxy)benzoyl]amino}-4-(trifluoromethyl)phenyl]cyclopropanecarboxylic acid;
(3) (1R,2S)-2-[3-{[4-(2-phenylethoxy)-2-(trifluoromethyl)benzoyl]amino}-4-(trifluoromethyl)phenyl]cyclopropanecarboxylic acid;
(4) (1R,2S)-2-[3-{[4-(1H-indazol-5-ylmethoxy)-2,6-dimethylbenzoyl]amino}-4-(trifluoromethyl)phenyl]cyclopropanecarboxylic acid;
(5) (1R,2S)-2-[3-{[2,6-dimethyl-4-(1,2,3,4-tetrahydro-1-naphthalenylmethoxy)benzoyl]amino}-4-(trifluoromethyl)phenyl]cyclopropanecarboxylic acid;
(6) (1R,2S)-2-[3-({2,6-dimethyl-4-[2-(3-pyridinyl)ethoxy]benzoyl}amino)-4-(trifluoromethyl)phenyl]cyclopropanecarboxylic acid;
(7) (1R,2S)-2-[3-({2,6-dimethyl-4-[2-(4-pyridinyl)ethoxy]benzoyl}amino)-4-(trifluoromethyl)phenyl]cyclopropanecarboxylic acid;
(8) (1R,2S)-2-[3-({2,6-dimethyl-4-[2-(2-pyridinyl)ethoxy]benzoyl}amino)-4-(trifluoromethyl)phenyl]cyclopropanecarboxylic acid;
(9) (1R,2S)-2-[3-({4-[2-(2-chloro-1H-imidazol-1-yl)ethoxy]-2,6-dimethylbenzoyl}amino)-4-(trifluoromethyl)phenyl]cyclopropanecarboxylic acid;
(10) (1R,2S)-2-[3-({4-[2-(2-fluorophenyl)ethoxy]-2,6-dimethylbenzoyl}amino)-4-(trifluoromethyl)phenyl]cyclopropanecarboxylic acid;
(11) (1R,2S)-2-[3-({4-[2-(3-fluorophenyl)ethoxy]-2,6-dimethylbenzoyl}amino)-4-(trifluoromethyl)phenyl]cyclopropanecarboxylic acid;
(12) (1R,2S)-2-[3-({4-[2-(4-fluorophenyl)ethoxy]-2,6-dimethylbenzoyl}amino)-4-(trifluoromethyl)phenyl]cyclopropanecarboxylic acid;
(13) (1R,2S)-2-[3-{[2,6-dimethyl-4-(3,3,3-trifluoropropoxy)benzoyl]amino}-4-(trifluoromethyl)phenyl]cyclopropanecarboxylic acid;
(14) (1R,2S)-2-[3-{[2,6-dimethyl-4-(3,3,3-trifluoro-2-methylpropoxy)benzoyl]amino}-4-(trifluoromethyl)phenyl]cyclopropanecarboxylic acid;
(15) (1R,2S)-2-{3-[(2,6-dimethyl-4-{[6-(trifluoromethyl)-2-pyridinyl]oxy}benzoyl)amino]-4-(trifluoromethyl)phenyl}cyclopropanecarboxylic acid;
(16) (1R,2S)-2-[3-{[2,6-dimethyl-4-(pyrazolo[1,5-a]pyrimidin-5-yloxy)benzoyl]amino}-4-(trifluoromethyl)phenyl]cyclopropanecarboxylic acid;
(17) rel-(1R,2S)-2-(3-{[2,6-dimethyl-4-(2-phenylethoxy)benzoyl]amino}-4-methylphenyl)cyclopropanecarboxylic acid;
(18) (1R,2S)-2-[3-{[4-(benzyloxy)-2-isopropylbenzoyl]amino}-4-(trifluoromethyl)phenyl]cyclopropanecarboxylic acid;
(19) (1R,2S)-2-[3-{[2-isopropyl-4-(2-phenylethoxy)benzoyl]amino}-4-(trifluoromethyl)phenyl]cyclopropanecarboxylic acid;
(20) (1R,2S)-2-[3-{[2-isopropyl-4-(3-phenylpropoxy)benzoyl]amino}-4-(trifluoromethyl)phenyl]cyclopropanecarboxylic acid;
(21) (1R,2S)-2-[3-{[3-(benzyloxy)-2-isopropylbenzoyl]amino}-4-(trifluoromethyl)phenyl]cyclopropanecarboxylic acid;
(22) (1R,2S)-2-[3-{[2-isopropyl-3-(2-phenylethoxy)benzoyl]amino}-4-(trifluoromethyl)phenyl]cyclopropanecarboxylic acid;
(23) (1R,2S)-2-[3-{[2-isopropyl-3-(3-phenylpropoxy)benzoyl]amino}-4-(trifluoromethyl)phenyl]cyclopropanecarboxylic acid;

(24) (1R,2S)-2-[4-(trifluoromethyl)-3-{[2,3,5-trimethyl-4-(2-phenylethoxy)benzoyl]amino}phenyl]cyclopropanecarboxylic acid;

(25) (1R,2S)-2-[3-({[3-isopropyl-1-(3-phenylpropyl)-1H-pyrazol-4-yl]carbonyl}amino)-4-(trifluoromethyl)phenyl]cyclopropanecarboxylic acid;

(26) (1R,2S)-2-[3-({[5-isopropyl-1-(3-phenylpropyl)-1H-pyrazol-4-yl]carbonyl}amino)-4-(trifluoromethyl)phenyl]cyclopropanecarboxylic acid;

(27) (1R,2S)-2-[3-({[2,6-dimethyl-4-(2-phenylethoxy)phenyl]carbonothioyl}amino)-4-(trifluoromethyl)phenyl]cyclopropanecarboxylic acid;

(28) (1R,2S)-2-[3-({[4-(2-cyclopropylethoxy)-2,6-dimethylphenyl]carbonothioyl}amino)-4-(trifluoromethyl)phenyl]cyclopropanecarboxylic acid;

(29) (1R,2S)-2-[3-({[2-sec-butyl-1-(3-phenylpropyl)-1H-pyrrol-3-yl]carbonyl}amino)-4-(trifluoromethyl)phenyl]cyclopropanecarboxylic acid;

(30) (1R,2S)-2-[3-({[2-isopropyl-1-(3-phenylpropyl)-1H-pyrrol-3-yl]carbonyl}amino)-4-(trifluoromethyl)phenyl]cyclopropanecarboxylic acid; or

(31) (1R,2S)-2-[3-({[2-(2-methyl-2-propanyl)-1-(3-phenylpropyl)-1H-pyrrol-3-yl]carbonyl}amino)-4-(trifluoromethyl)phenyl]cyclopropanecarboxylic acid.

8. A pharmaceutical composition comprising the compound according to claim 1 or a pharmaceutically acceptable salt thereof as an active ingredient, and a pharmaceutically acceptable carrier.

9. The pharmaceutical composition according to claim 8, wherein the pharmaceutical composition is an $EP_2$ receptor antagonist.

10. A treatment regimen, comprising the pharmaceutical composition according to claim 8, and at least one component selected from an alkylating agent, an antimetabolic agent, an anticancer antibiotic, a plant-derived preparation, a hormonal agent, a platinum compound, a topoisomerase inhibitor, a kinase inhibitor, an anti-CD20 antibody, an anti-human epidermal growth factor receptor (HER2) antibody, an anti-epidermal growth factor receptor (EGFR) antibody, an anti-vascular endothelial growth factor (VEGF) antibody, a proteasome inhibitor, a histone deacetylase (HDAC) inhibitor and an immunomodulatory drug.

11. A method for treating colorectal cancer in a patient in need thereof, the method comprising administering the compound according to claim 1, or a pharmaceutically acceptable salt thereof to the patient.

12. A compound or a pharmaceutically acceptable salt thereof, wherein the compound is (1R,2S)-2-[3-{[2,6-dimethyl-4-(2-phenylethoxy)benzoyl]amino}-4-(trifluoromethyl)phenyl]cyclopropanecarboxylic acid.

13. A compound of the following structure:

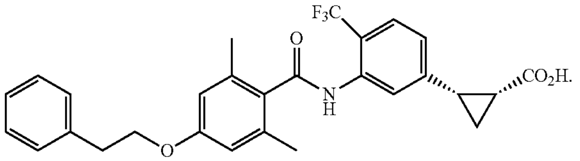 [SMILES: Cc1cc(OCCc2ccccc2)cc(C)c1C(=O)Nc1cc([C@H]2C[C@H]2C(=O)O)ccc1C(F)(F)F]

14. A pharmaceutically acceptable salt of the compound of the following structure:

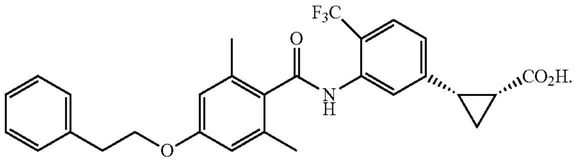 [SMILES: Cc1cc(OCCc2ccccc2)cc(C)c1C(=O)Nc1cc([C@H]2C[C@H]2C(=O)O)ccc1C(F)(F)F]

* * * * *